US008252940B2

(12) United States Patent
Felise et al.

(10) Patent No.: US 8,252,940 B2
(45) Date of Patent: Aug. 28, 2012

(54) 5-SUBSTITUTED-2-IMINO-THIAZOLIDINONE COMPOUNDS AND THEIR USE AS INHIBITORS OF BACTERIAL INFECTION

(75) Inventors: Heather B. Felise, Lynnwood, WA (US); Samuel I. Miller, Seattle, WA (US); Toni Kline, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 12/856,986

(22) Filed: Aug. 16, 2010

(65) Prior Publication Data

US 2011/0039849 A1 Feb. 17, 2011

Related U.S. Application Data

(63) Continuation of application No. PCT/US2009/034134, filed on Feb. 13, 2009.

(60) Provisional application No. 61/028,777, filed on Feb. 14, 2008.

(51) Int. Cl.
*C07D 417/06* (2006.01)
*C07D 277/04* (2006.01)
*A61K 31/445* (2006.01)
*A61K 31/427* (2006.01)

(52) U.S. Cl. .................... 548/184; 546/209; 546/269.7; 514/326; 514/369

(58) Field of Classification Search ........................ None
See application file for complete search history.

(56) References Cited

U.S. PATENT DOCUMENTS 6,136,542 A 10/2000 Demers et al.

FOREIGN PATENT DOCUMENTS

DE 2614798 A1 10/1976
GB 1473752 A 5/1977

OTHER PUBLICATIONS

Zervosen et al. Antimicrobial Agents and Chemotherapy (2004), pp. 961-969.*

Felise et al. Cell Host & Microbe 4, pp. 325-336 (2008).*

Kline et al. J. Med. Chem. 51, pp. 7065-7074 (2008).*

Ghosh P (2004) Process of protein transport by the type III secretion system, Microbiol Mol Biol Rev 68: 771-795.*

Mota et al, The bacterial injection kit: Type III secretion systems, Annals of Medicine (Basingstoke, United Kingdom) (2005), 37(4), 234-249.*

International Preliminary Report on Patentability mailed Aug. 26, 2010, issued in corresponding International Application No. PCT/US2009/034134, filed Feb. 13, 2009, 7 pages.

Akerblom, E.B., "Synthesis and Structure-Activity Relationships of a Series of Antibacterially Active 5-(5-Nitro-2-furfurylidene)thiazolones, 5-(5-Nitro-2-furylpropenylidene)thiazolones, and 6-(5-Nitro-2-furyl)-4H-1,3-thiazinones," Journal of Medicinal Chemistry 17(6):609-615, 1974.

International Search Report and Written Opinion, mailed Nov. 20, 2009, issued in corresponding International Application No. PCT/US2009/034134, filed Feb. 13, 2009.

Kauppi, A.M., et al., "Targeting Bacterial Virulence: Inhibitors of Type III Secretion in Yersinia," Chemistry & Biology 10(3):241-249, Mar. 2003.

Schlumberger, M.C., et al., "Real-Time Imaging of Type III Secretion: Salmonella SipA Injection Into Host Cells," PNAS (Proceedings of the National Academy of Sciences of the United States of America) 102(35):12548-12553, Aug. 2005.

Zhang, S., et al., "The Salmonella enterica Serotype Typhimurium Effector Proteins SipA, SopA, SopB, SopD, and SopE2 Act in Concert to Induce Diarrhea in Calves," Infection and Immunity 70(7):3843-3855, Jul. 2002.

* cited by examiner

*Primary Examiner* — Kamal Saeed
*Assistant Examiner* — Nyeemah A Grazier
(74) *Attorney, Agent, or Firm* — Christensen O'Connor Johnson Kindness PLLC

(57) ABSTRACT

A method for inhibiting Gram-negative bacterial pathogenesis, a method of screening for compounds that inhibit type III secretion in Gram-negative bacteria, and compounds that inhibit type III secretion in Gram-negative bacteria.

7 Claims, 5 Drawing Sheets a.

b.

5-SUBSTITUTED-2-IMINO-THIAZOLIDINONE COMPOUNDS AND THEIR USE AS INHIBITORS OF BACTERIAL INFECTION

CROSS-REFERENCES TO RELATED APPLICATIONS

This application is a continuation of International Application No. PCT/US2009/034134, filed Feb. 13, 2009, which claim the benefit of U.S. Provisional Application No. 61/028,777, filed Feb. 14, 2008. Each application is incorporated herein by reference in its entirety.

STATEMENT OF GOVERNMENT LICENSE RIGHTS

This invention was made with Government support under Contract No. U54 A105714, awarded by the National Institutes of Health, National Institute of Allergy and Infectious Diseases, Contract No. 5ROI A130479-13, awarded by the National Institutes of Health, and Contract No. 5ROI A1048683-04, awarded by the National Institutes of Health. The Government has certain rights in the invention.

FIELD OF THE INVENTION

The present invention relates to 5-substituted 2-iminothiazolidinone compounds as inhibitors of type III secretion in Gram-negative bacteria and a method of screening for compounds that inhibit type III secretion in Gram-negative bacteria.

BACKGROUND OF THE INVENTION

In the twentieth century the treatment of infectious diseases was revolutionized by the development of antibiotics. However, due to their widespread use resistance to antibiotics is increasing on a global scale, such that adequate therapies are lacking for both previously controlled and emerging bacterial diseases. Moreover, the molecular targets and mechanisms of action of most newly developed antibiotics are similar to current ones, reducing their efficacy in the face of resistance. The effective treatment of infectious diseases in the face of increasing antibiotic resistance requires the development of pharmaceuticals that act upon novel conserved targets.

Bacterial virulence properties are viable targets for the development of novel therapeutic agents because such agents would not kill bacteria themselves but block disease. Because these agents would not inhibit general bacterial growth as part of their mechanism of action, this strategy could decrease the likelihood for selection of resistance and reduce side effects by sparing commensal organisms. However, many pathogenic mechanisms are microbial specific, necessitating more rapid pathogen identification than currently is in clinical practice to be useful. Furthermore, a restricted spectrum of activity would decrease the economic incentive necessary for their development.

In the case of many self-limiting enteric infections, the use of traditional antibiotics may prolong colonization and increase toxin release and, therefore, antibiotic treatment would not be recommended. Furthermore, compounds that target virulence properties may be particularly relevant for biodefense in which organisms resistant to traditional antibiotics may be generated by genetic engineering. Engineering organisms resistant to anti-virulence agents may not be as straightforward, as organisms resistant to antibiotics can be generated by selection for bacterial growth, but such a selection would not exist for reconstitution of bacterial virulence properties. In addition, for purposes of biodefense, there is a need for therapeutic agents with a broad spectrum of activity, because single treatments for single infectious agents present problems in terms of production, diagnosis, storage, and distribution.

Gram-negative bacterial virulence secretion systems are essential for a wide array of animal and plant infectious diseases. Two prominent examples of Gram-negative bacterial virulence associated secretion systems, termed type II secretion (T2S) and type III secretion (T3S), are responsible for the pathogenesis of many infectious diseases including plague, gastroenteritis, Gram-negative pneumonia, dysentery, enteric fever, tularemia, trachoma, endometritis, and a variety of plant diseases. T2S is also known as the terminal component of the General Secretory Pathway (GSP), because it is a two step process where substrates are secreted across the bacterial inner membrane by the GSP, also known as sec-dependent secretion and subsequently transported across the outer membrane. T2S systems secrete a variety of mammalian toxins as well as proteins, which degrade host cell components, such as proteins, lipids and sugars of the extracellular matrix. Interestingly, a number of the genes required for T2S are homologous to those required for type IV pilus (T4P) assembly on the cell surface of some bacteria. T4P are required for twitching motility, a flagella independent form of bacterial translocation, which plays a role in host colonization and biofilm formation in organisms, such as enteropathogenic *E. coli* (EPEC), *Pseudomonas aeruginosa, Vibrio cholera* and *Neisseria gonorrhea*. T3S systems are complex multi protein organelles that assemble in the bacterial membrane of more than 25 Gram-negative animal and plant pathogens to deliver multiple virulence proteins directly from the bacterial cytosol into host cells. These secreted proteins influence host cell physiology by altering a variety of antibacterial functions with resultant disease.

Unfortunately, many of the components of Gram-negative bacterial secretion systems are not well conserved among the various systems and would not make ideal drug targets, but one component the secretin, has a broadly conserved structure despite diverse amino acid sequence. The secretin protein associates into large and highly stable oligomeric complexes of 12-14 subunits in the outer membrane, which functions as an export channel for substrate secretion. In T3S systems these proteins form the outer membrane component of the needle complex (NC); a multi protein complex that is the transmembrane component of the complex T3S apparatus. Secretins are membrane spanning proteins that are synthesized in the bacterial cytoplasm and exported to the periplasm by the sec-dependent pathway. In many systems the secretin has a dedicated lipoprotein that appears to function to promote insertion and polymerization of the ring in the outer membrane. Secretin proteins have two major domains, which are approximately equal in length. The C terminal domain is well conserved and believed to anchor the protein in the membrane by 10 14 potentially transmembrane amphipathic β strains characteristic of other outer membrane proteins. In contrast, the N terminal domain is much less conserved and believed to facilitate recognition of substrates and confer secretion specificity. Finally, there is occasionally a third domain present downstream from the C terminal domain, which interacts with the lipoprotein to facilitate localization to the outer membrane.

There exists a need for inhibitors of type III secretion in Gram-negative bacteria. The present invention fulfills this need, and provides further related advantages.

SUMMARY OF THE INVENTION

In one aspect, the invention provides a recombinant construct for use in screening potential compounds of interest. The recombinant construct includes:

(a) a first nucleotide sequence encoding a secretion signal for a type III secretion system, wherein the first nucleotide sequence is derived from a first bacterial species; and (b) a second nucleotide sequence encoding a reporter protein secreted by a type III secretion system operably joined to the first nucleotide sequence, wherein the second nucleotide sequence is derived from a second bacterial species that is different from the first bacterial species.

In one embodiment, the recombinant construct encodes a fusion protein having a secretion signal operably joined to a reporter protein. In one embodiment of the construct, the secretion signal is a polypeptide fragment of a naturally occurring protein secreted by the type III secretion system. In a preferred embodiment of the construct, the secretion signal is a polypeptide fragment of SipA. The polypeptide fragment of SipA comprises SEQ ID NO:1. In one embodiment of the construct, the polypeptide fragment of SipA is encoded by a nucleotide sequence comprising SEQ ID NO:2.

In one embodiment of the construct, the reporter protein is a naturally occurring protein secreted by a Gram-negative bacterial cell. In a preferred embodiment, the reporter protein is a polypeptide fragment of YplA. The polypeptide fragment of YplA comprises SEQ ID NO:3. In one embodiment of the construct, the polypeptide fragment of YplA is encoded by a nucleotide sequence comprising SEQ ID NO:4.

In one aspect, the invention provides a host cell containing a recombinant construct as described above, the host cell and the first nucleotide sequence derived from the first bacterial species and the second nucleotide sequence derived from a different bacterial species than the first bacterial species.

In another aspect, the invention provides a bacterial cell, including:

(a) a first recombinant expression construct comprising a first nucleotide sequence from a first bacterial species encoding a secretion signal for a type III secretion system and a second nucleotide sequence from a second bacterial species encoding a reporter protein secreted by a type III secretion system;

(b) a second recombinant expression construct having a transcriptional regulator of type III secretion system gene expression; and (c) a chromosomal mutation to reduce or eliminate the expression of a flagella structural gene.

In one embodiment of the bacterial cell, the first nucleotide sequence is expressed from its native promoter.

In one embodiment of the bacterial cell, the first bacterial species is selected from the group consisting of *Shigella, Salmonella, Yersinia, Escherichia, Pseudomonas, Xanthomonas, Ralstonia*, and *Erwinia*. In a preferred embodiment, the first bacterial species is *Salmonella.*

In one embodiment of the bacterial cell, the first recombinant expression construct further comprises a nucleotide sequence encoding a fusion protein comprising a secretion signal linked by an in-frame gene fusion to a reporter protein.

In a preferred embodiment of the bacterial cell, the secretion signal is a polypeptide fragment of SipA. In another preferred embodiment of the bacterial cell, the reporter protein is a polypeptide fragment of YplA.

In one embodiment of the bacterial cell, the transcriptional regulator of type III secretion system gene expression is encoded by a hilA gene. In another embodiment of the bacterial cell, the transcriptional regulator is expressed from its native promoter and is operably linked to an inducible promoter.

In one embodiment of the bacterial cell, the chromosomal mutation to reduce or eliminate the expression of a flagella structural gene affects a transcriptional regulator of flagellar gene expression. In a preferred embodiment, the chromosomal mutation is a transposon insertion in the gene.

In one aspect, the present invention provides a method of screening for a compound that inhibits type III secretion in Gram-negative bacteria, comprising:

(a) contacting a candidate compound with a Gram-negative bacterial cell comprising a first recombinant expression construct comprising a nucleotide sequence encoding a reporter protein operably coupled to a signal sequence for secretion by a type III secretion system; and (b) detecting the presence or activity of the reporter protein in culture supernates, wherein detecting the presence or activity of the reporter protein indicates whether the sample compound inhibits the type III system secretion.

In one embodiment of the screening method, the Gram-negative bacterial cell is selected from the group consisting of *Shigella, Salmonella, Yersinia, Escherichia, Pseudomonas, Xanthomonas, Ralstonia*, and *Erwinia*. In a preferred embodiment, the Gram-negative bacterial cell is *Salmonella.*

In one embodiment of the screening method, the signal sequence is SipA. In another embodiment of the screening method, the reporter protein is YplA.

In one embodiment of the screening method, detecting the presence or activity of the reporter protein includes measuring the intensity of a fluorogenic phospholipase substrate. The fluorogenic phospholipase substrate is located outside the bacterial cell. In a preferred embodiment, the fluorogenic phospholipase substrate is PED6.

In one embodiment of the screening method, the Gram-negative bacterial cell includes a second recombinant expression construct having a transcriptional regulator of type III secretion system gene expression. The transcriptional regulator is expressed from its native promoter and is operably linked to an inducible promoter.

In one embodiment of the screening method, the transcriptional regulator is encoded by a hilA gene, wherein type III secretion system gene expression is increased by increasing expression of the hilA gene. In a preferred embodiment, the type III secretion system gene expression is increased by providing about 30 copies of the hilA gene in a bacterial cell.

In one embodiment of the screening method, the Gram-negative bacterial cell contains a flagella structural gene that is inactivated.

In one embodiment of the screening method, the screening method further comprises:

(c) conducting at least one additional screen to determine whether the sample compound is a specific inhibitor of type III secretion; and (d) identifying a sample compound that is a specific inhibitor of type III secretion.

In one embodiment of the screening method, the at least one additional screen is useful for identifying compounds that inhibit transcription.

In another embodiment of the screening method, the at least one additional screen comprises measuring transcription of a type III secretion gene in the presence of a candidate compound.

In one embodiment of the screening method, the at least one additional screen is useful for identifying compounds that inhibit protein translation, inhibit sec-dependent secretion, or inhibit bacterial growth. In a preferred embodiment, the at least one additional screen comprises measuring expression of a type III secretion system structural gene in the presence of a candidate compound.

Yet another aspect of the invention provides a recombinant expression construct, including:

(a) a first nucleotide sequence encoding a *Salmonella enterica* serovar *Typhimurium* type III secretion signal; and (b) a second nucleotide sequence encoding a *Yersinia enterocolitica* phospholipase A2 protein that is operably linked to the first nucleotide sequence.

In one embodiment of the construct, expression of the construct within a Gram-negative bacterial host cell produces a fusion protein that is capable of being secreted by a type III secretion system.

In a preferred embodiment, the host cell is *Salmonella enterica* serovar *Typhimurium.*

Another aspect of the invention provides a modified Gram-negative bacterial cell, comprising:

(a) a *Salmonella enterica* serovar *Typhimurium* cell that secretes a phospholipase A2 reporter construct, the reporter construct comprising a first nucleotide sequence encoding a *Salmonella typhimurium* type III secretion signal and a second nucleotide sequence encoding a *Yersinia enterocolitica* phospholipase A2 polypeptide;

(b) a bacterial plasmid containing at least one nucleotide sequence encoding a hilA gene, wherein expression of the hilA gene increases secretion by a type III secretion system; and (c) a modified flagella structural gene that inhibits assembly of a flagellar secretion system.

In one embodiment of the modified Gram-negative bacterial cell, the reporter construct is secreted by the type III secretion system.

In another embodiment of the modified Gram-negative bacterial cell, the secretion signal is SipA.

In another aspect, the invention provides compounds that are inhibitors of type III secretion in Gram-negative bacteria.

In a further aspect, the invention provides a method for treating a type III secretion-mediated condition, comprising administering a type III secretion inhibitor compound of the invention.

In another aspect, the invention provides a method for inhibiting Gram-negative bacterial pathogenesis. In the method, Gram-negative bacterial pathogenesis is inhibited by administering an effective amount of a thiazolidinone compound to a subject in need thereof. The thiazolidinone compound is a 4-thiazolidinone, preferably a 5-arylidene-2-imino-4-thiazolidinone compound.

In one embodiment, the method for inhibiting Gram-negative bacterial pathogenesis comprises administering an effective amount of a compound to a subject in need thereof, the compound having the formula:

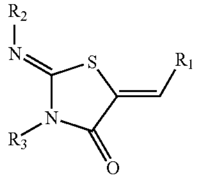

wherein, $R_1$ is selected from:

(a) substituted and unsubstituted aryl, (b) substituted and unsubstituted heteroaryl, (c) substituted and unsubstituted alkyl, and (d) substituted and unsubstituted cycloalkyl;

$R_2$ is substituted or unsubstituted aryl; and $R_3$ is selected from:

(a) hydrogen, (b) substituted or unsubstituted alkyl, (c) substituted or unsubstituted cycloalkyl, (d) substituted or unsubstituted aryl, (e) substituted or unsubstituted heteroaryl, (f) $—CH(R_4)—W—Y$, wherein W is selected from (i) Q-$CH(R_5)$, wherein $R_4$ and $R_5$ are independently selected from natural and non-natural amino acid side chains, and Q is selected from $—C(=O)NH—$, $—C(=O)O—$, $—SO_2NH—$, and $—P(O)(OR_8)NH—$, wherein $R_8$ is selected from hydrogen and substituted or unsubstituted alkyl, or (ii) $C(=O)NR_6CH(R_7)$, wherein $R_6$ and $R_7$ taken together with the carbon and the nitrogen atoms to which they are attached form a 5- to 7-membered ring that optionally includes one or more heteroatoms, and wherein Y is selected from $—C(=O)NH_2$, $—C(=O)OH$, $—SO_2NH_2$, and $—P(O)(OR_8)NH_2$, wherein $R_8$ is selected from hydrogen and substituted or unsubstituted alkyl, and (g) $—(CH_2)_nN(R_9)X(CH_2)_mR_{10}$, wherein n is an integer from 1 to 8, m is an integer from 1 to 8, X is selected from $C(=O)$, $N(C=O)OH$, $N(C=NH)NH$, and $CH_2$, $R_9$ is hydrogen or substituted or unsubstituted alkyl, and $R_{10}$ is heterocyclyl.

In another embodiment, the method for inhibiting Gram-negative bacterial pathogenesis comprises administering an effective amount of a compound to a subject in need thereof, the compound having the formula:

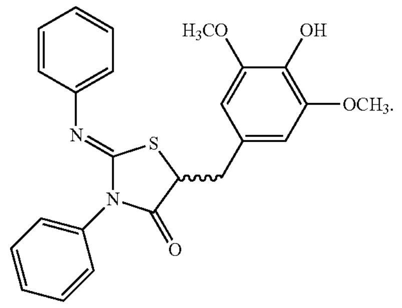

In another aspect of the invention, compounds that inhibit Gram-negative bacterial pathogenesis are provided.

In one embodiment, the compounds have formula (I):

(I)

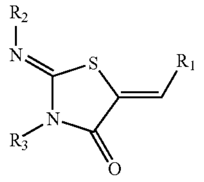

wherein, $R_1$ is selected from:

(a) substituted and unsubstituted aryl, (b) substituted and unsubstituted heteroaryl, (c) substituted and unsubstituted alkyl, and (d) substituted and unsubstituted cycloalkyl;

$R_2$ is substituted or unsubstituted aryl; and $R_3$ is selected from:

(a) —CH($R_4$)—W—Y, wherein W is selected from (i) Q-CH($R_5$), wherein $R_4$ and $R_5$ are independently selected from natural and non-natural amino acid side chains, and Q is selected from —C(═O)NH—, —C(═O)O—, —$SO_2$NH—, and —P(O)($OR_8$)NH—, wherein $R_8$ is selected from hydrogen and substituted or unsubstituted alkyl, and (ii) C(═O)$NR_6$CH($R_7$), wherein $R_6$ and $R_7$ taken together with the carbon and the nitrogen atoms to which they are attached form a 5- to 7-membered ring that optionally includes one or more heteroatoms, and wherein Y is selected from —C(═O)$NH_2$, —C(═O)OH, —$SO_2NH_2$, and —P(O)($OR_8$)$NH_2$, wherein $R_8$ is selected from hydrogen and substituted or unsubstituted alkyl, and (b) substituted or unsubstituted C1-C10 alkyl, with the proviso that when $R_3$ is C1-C3 alkyl, $R_3$ further includes a heteroatom selected from O, N, and S.

In another embodiment, the compounds that inhibit Gram-negative bacterial pathogenesis have formula (II):

(II)

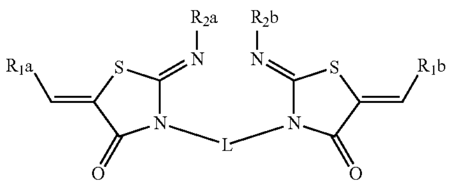

wherein, $R_{1a}$ and $R_{1b}$ are independently selected from:

(a) substituted and unsubstituted aryl, (b) substituted and unsubstituted heteroaryl, (c) substituted and unsubstituted alkyl, and (d) substituted and unsubstituted cycloalkyl;

$R_{2a}$ and $R_{2b}$ are independently is selected from:

(a) hydrogen, (b) substituted or unsubstituted aryl, and (c) substituted and unsubstituted heteroaryl; and L is a linker moiety having at least six atoms.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
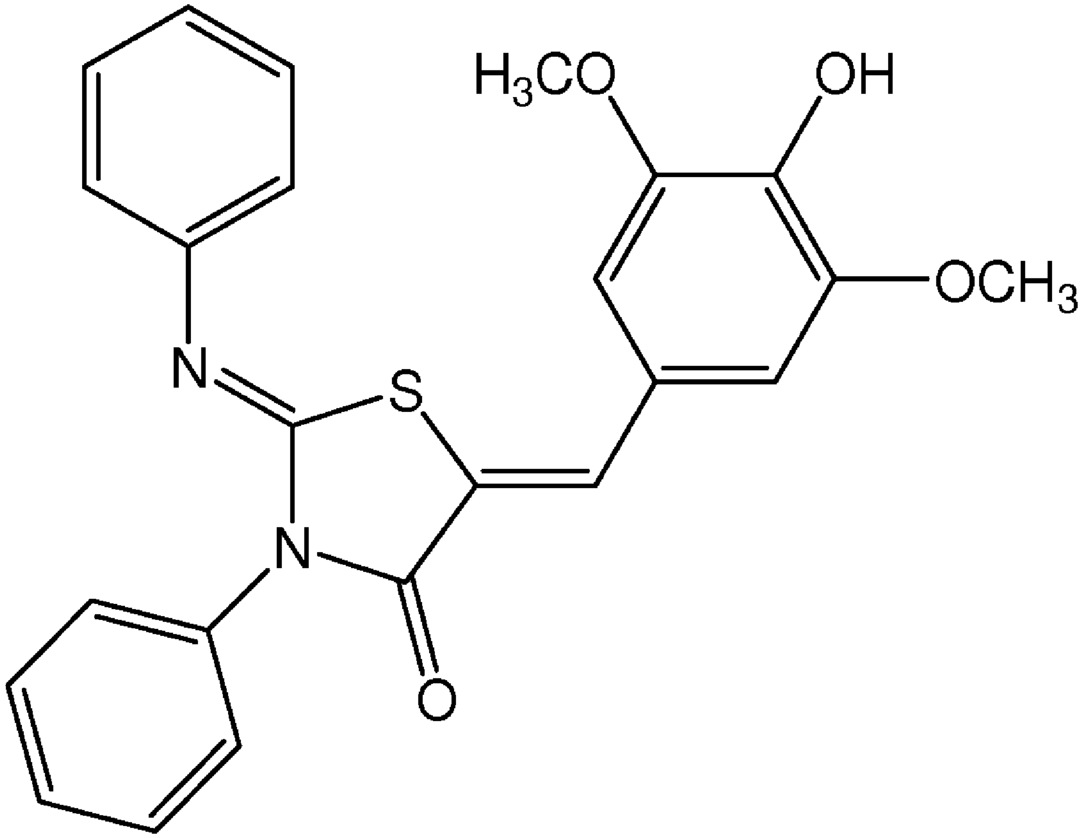
FIG. 1 is the chemical structure of Compound 1, a representative compound of the invention.

The present invention provides a method for inhibiting Gram-negative bacterial pathogenesis, a method of screening for compounds that inhibit type III secretion in Gram-negative bacteria, and compounds that inhibit type III secretion in Gram-negative bacteria.

The method for inhibiting Gram-negative bacterial pathogenesis is useful for blocking type II and type III secretion as well as virulence functions of a wide array of animal and plant bacterial pathogens. The screening method is useful for identifying compounds that target the type III secretion system, and for the development of related therapeutic agents with a broad spectrum of activity that could be used to prevent and treat bacterial diseases.

Secretion systems are utilized by bacterial pathogens to assemble surface structures to promote adherence and deliver protein "toxins" to host cells. A family of small molecules, termed thiazolidinones, is identified that inhibits bacterial secretion systems, including T2S and T3S, in a wide array of animal and plant pathogens, but does not affect bacterial growth. Moreover, these compounds can inhibit cytotoxicity of macrophages by *S. typhimurium*, as well as the pathology of the plant pathogen *P. syringae*. Finally, these compounds appear to target the secretin protein of these systems and block either the assembly or stability of the oligomeric complex in the outer membrane.

As T2 and T3 bacterial secretion systems have a single conserved component, Compound 1 (see FIG. 1) appears to be mediating its broad spectrum of activity by targeting the secretin protein. Secretins are membrane-spanning proteins that are synthesized in the bacterial cytoplasm and subsequently exported to the periplasm by the sec-dependent pathway. In addition, they have been shown to have a broadly conserved structure and associate into an oligomeric complex in the bacterial outer membrane. This structure is highly stable and functions as an export channel for substrate secretion across this barrier, by either of these secretion systems.

Identification of inhibitors of T3S. To screen biological and chemical small molecule libraries for inhibitors of secretin function, a whole cell High-Throughput Screen (HTS) for inhibitors of T3S was used. T3S systems, which are evolutionarily related to flagella, are complex multi protein organelles that assemble in the bacterial membrane to deliver virulence proteins directly from the bacterial cytosol into host cells. These secreted proteins influence host cell physiology by altering a variety of antibacterial functions, facilitating infection. Historically, a disadvantage of cell based inhibitor screens is that the targets are not immediately apparent. *Salmonella enterica* serovar *Typhimurium* was chosen as a test organism, because a number of rapid secondary assays were available for this organism to establish the specificity of inhibitors from whole cell assays for secretin function. For the HTS, a novel strain of *S. typhimurium* that secretes a recombinant phospholipase A2 reporter construct in a T3S dependent manner was designed and constructed.

Recombinant Construct. In one aspect, the invention provides a recombinant construct for use in screening potential compounds of interest. The recombinant construct includes:

(a) a first nucleotide sequence encoding a secretion signal for a type III secretion system, the first nucleotide sequence derived from a first bacterial species; and (b) a second nucleotide sequence encoding a reporter protein secreted by a type III secretion system, the second nucleotide sequence is derived from a second bacterial species that is different from the first bacterial species.

In one embodiment, the recombinant construct is a fusion protein comprising a secretion signal that is operably joined to a reporter protein. The secretion signal is a polypeptide fragment of a naturally occurring protein secreted by the type III secretion system. As used herein, the term polypeptide fragment refers to either a full-length or truncated peptide or polypeptide.

In one embodiment of the construct, the secretion signal is a polypeptide fragment of SipA. SipA, also referred to in the literature as SspA, is a *S. typhimurium* T3S substrate. In a preferred embodiment, the polypeptide fragment of SipA is represented by the amino acid sequence in SEQ ID NO:1.

In one embodiment of the construct, the polypeptide fragment of SipA can be encoded by the nucleotide sequence in SEQ ID NO:2.

The reporter protein is a naturally occurring protein secreted by a Gram-negative bacterial cell. In one embodiment of the construct, the reporter protein is a polypeptide fragment if YplA, a *Yersinia enterocolitica* T3S secreted substrate. In a preferred embodiment, YplA is represented by the amino acid sequence in SEQ ID NO:3.

In this embodiment of the construct, the first 59 amino acids have been removed from YplA, because they have been shown to contain the signal sequence for its secretion by the *Y. enterocolitica* Ysa T3S system, but are not required for its enzymatic activity. The polypeptide fragment of YplA can be encoded by the nucleotide sequence in SEQ ID NO:4.

In this embodiment, the first 177 nucleotides have been removed from YplA because they encode the *Y. enterocolitica* type III secretion signal.

In one aspect, the invention provides a host cell containing a recombinant construct as described above. The host cell and the first nucleotide sequence are derived from a first bacterial species, and the second nucleotide sequence is derived from a different bacterial species than the first bacterial species.

In one aspect, the invention provides a recombinant expression construct including:

(a) a first nucleotide sequence encoding a *Salmonella enterica* serovar *Typhimurium* type III secretion signal; and (b) a second nucleotide sequence encoding a *Yersinia enterocolitica* phospholipase A2 protein that is operably linked to the first nucleotide sequence.

In one embodiment, expression of the construct within a Gram-negative bacterial host cell produces a fusion protein that is capable of being secreted by a type III secretion system. In a preferred embodiment, the host cell is *Salmonella enterica* serovar *Typhimurium.*

Bacterial Strain. In one aspect, the invention provides a bacterial cell that includes:

(a) a first recombinant expression construct having a first nucleotide sequence from a first bacterial species encoding a secretion signal for a type III secretion system and a second nucleotide sequence from a second bacterial species encoding a reporter protein secreted by a type III secretion system;

(b) a second recombinant expression construct having a transcriptional regulator of type III secretion system gene expression; and (c) a chromosomal mutation to reduce or eliminate the expression of a flagella structural gene.

In one embodiment of the bacterial cell, the first bacterial species is selected from the group consisting of *Shigella, Salmonella, Yersinia, Escherichia, Pseudomonas, Xanthomonas, Ralstonia*, and *Erwinia*. In a preferred embodiment, the first bacterial species is *Salmonella.*

In one embodiment of the bacterial cell, the first recombinant expression construct has a nucleotide sequence encoding a fusion protein that includes a secretion signal linked by an in-frame gene fusion to a reporter protein. In one embodiment of the bacterial cell, the secretion signal for a type III secretion system is a polypeptide fragment of SipA. SipA, also referred to in the literature as SspA, is a *S. typhimurium* T3S substrate.

In one embodiment of the bacterial cell, the reporter protein is a polypeptide fragment of YplA. YplA is a T3S secreted substrate from *Y. enterocolitica*. Preferably, the first 59 amino acids have been removed from YplA, because they have been shown to contain the signal sequence for its secretion by the *Y. enterocolitica* Ysa T3S system, but are not required for its enzymatic activity.

The second recombinant expression construct has a transcriptional regulator of type III secretion system gene expression. The transcriptional regulator is expressed from its native promoter and is operably linked to an inducible promoter. In one embodiment of the bacterial cell, the transcriptional regulator is encoded by a hilA gene, thereby providing additional copies of the hilA gene within the bacterial cell. In one embodiment, the bacterial cell contains around 30 copies of the hilA gene.

In one embodiment of the bacterial cell, the chromosomal mutation affects a transcriptional regulator of flagellar gene expression. The chromosomal mutation reduces or eliminates the expression of a flagella structural gene. In a preferred embodiment, the chromosomal mutation is a transposon insertion in the flhC gene.

In one aspect, the invention provides a modified Gram-negative bacterial cell that includes:

(a) a *Salmonella enterica* serovar *Typhimurium* cell that secretes a phospholipase A2 reporter construct, the reporter construct comprising a first nucleotide sequence encoding a *Salmonella typhimurium* type III secretion signal and a second nucleotide sequence encoding a *Yersinia enterocolitica* phospholipase A2 polypeptide;

(b) a bacterial plasmid containing at least one nucleotide sequence encoding a hilA gene, wherein expression of the hilA gene increases secretion by a type III secretion system; and (c) a modified flagella structural gene that inhibits assembly of a flagellar secretion system.

In one embodiment of the modified Gram-negative bacterial cell, the reporter construct is secreted by the type III secretion system. In another embodiment, the secretion signal is SipA.

Screening Method. In one aspect, the present invention provides a method of screening for a compound that inhibits type III secretion in Gram-negative bacteria. The screening method includes:

(a) contacting a candidate compound with a Gram-negative bacterial cell comprising a first recombinant expression construct comprising a nucleotide sequence encoding a reporter protein operably coupled to a signal sequence for secretion by a type III secretion system; and (b) detecting the presence or activity of the reporter protein in culture supernates, wherein detecting the presence or activity of the reporter protein indicates whether the sample compound inhibits the type III system secretion.

In the above methods, the Gram-negative bacterial cell is selected from the group consisting of *Shigella, Salmonella, Yersinia, Escherichia, Pseudomonas, Xanthomonas, Ralstonia*, and *Erwinia*. In a preferred embodiment of the screening method, the Gram-negative bacterial cell is *Salmonella*.

In the above methods, the signal sequence is SipA. In another embodiment of the screening method, the reporter protein is YplA.

The screening method includes detecting the presence or activity of the reporter protein in culture supernates. In one embodiment of the method, detecting the presence or activity of the reporter protein comprises measuring the intensity of a fluorogenic phospholipase substrate, wherein the fluorogenic phospholipase substrate is located outside the bacterial cell. In a preferred embodiment, the fluorogenic phospholipase substrate is PED6.

Phospholipase activity is frequently used as a reporter in High-Throughput (HT) assays because of the availability of phospholipase substrates with a cleavage product that is fluorescent. The assay was based on cleavage, by the phospholipase A2 reporter construct, of the substrate PED6: N-((6-(2,4-dinitro-phenyl)amino)-hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine. Such cleavage results in an increase in absorbance readily measured using a fluorometer. When PED6 is added directly to a culture of the engineered *Salmonella* strain, fluorescence is proportional to the amount of phospholipase reporter secreted by the T3S system.

In the above screening method, the Gram-negative bacterial cell further comprises a second recombinant expression construct having a transcriptional regulator of type III secretion system gene expression, wherein the transcriptional regulator is expressed from its native promoter and is operably linked to an inducible promoter. In a preferred embodiment, the transcriptional regulator is encoded by a hilA gene. Type III secretion system gene expression is increased by increasing expression of the hilA gene. Type III secretion system gene expression is increased by providing about 30 copies of the hilA gene in a bacterial cell.

In the above methods, the Gram-negative bacterial cell contains a flagella structural gene that is inactivated.

Using this HTS, 92,000 small molecules from both natural and synthetic compound libraries were screened for compounds that resulted in a reduction in fluorescence (z scores>3.0), signifying a reduction in T3S similar to a genetic T3S mutant (National Screening Laboratory for the Regional Centers of Excellence in Biodefense and Emerging Infectious Disease, Boston, Mass.). This screen yielded 89 putative T3S inhibitors that had at most a modest effect on bacterial growth. Of these, 57 were judged to lack novelty or potential for drug development, and 32 were further studied. Because inhibition of a variety of general bacterial processes not specific to T3S would have been positive in the HTS, including gene transcription, protein translation, sec-dependent secretion, and disulfide bond isomerization, secondary assays were performed to define screening positives specific for T3S.

Secondary screens can be used to identify non-specific inhibitors of cellular processes. In one aspect, the invention provides the method of screening described above, and further including:

(c) conducting at least one additional screen to determine whether the sample compound is a specific inhibitor of type III secretion; and (d) identifying a sample compound that is a specific inhibitor of type III secretion.

In one embodiment of the screening method, the additional screen is useful for identifying compounds that inhibit transcription. In another embodiment, the additional screen involves measuring transcription of a type III secretion gene in the presence of a candidate compound. For example, to identify non-specific inhibitors of transcription, expression of the flagellar regulatory gene (flhC) was measured using a transcriptional fusion to the lacZ gene. More than one additional screen may be performed.

In one embodiment of the screening method, the additional screen is useful for identifying compounds that inhibit protein translation, inhibit sec-dependent secretion, or inhibit bacterial growth. In another embodiment, the additional screen comprises measuring expression of a type III secretion system structural gene in the presence of a candidate compound.

For example, to eliminate compounds inhibiting bacterial translation, sec-dependent secretion, or disulfide bond isomerization, alkaline phosphatase activity of a PrgH'-'PhoA protein fusion was measured in the presence of the various compounds. PrgH is an essential inner membrane component of the T3S apparatus secreted by the sec-dependent pathway, and alkaline phosphatase activity requires disulfide bond formation; thus, inhibition of fusion protein expression and/or its localization would result in decreased alkaline phosphatase activity. While many of the identified compounds reduced β-Galactosidase activity and/or alkaline phosphatase activity, cultures grown in the presence of five of the 32 compounds assayed had 80-100% of the activity observed for cells grown in the absence of compound on repeated measurement. Thus, these five compounds lacked a general effect on bacterial transcription, translation, sec-dependent secretion, and bacterial growth.

The subject compounds could still have had a specific transcriptional effect on T3S gene expression. Therefore, the effect of these compounds on transcription of three different T3S genes that encode a transcriptional regulator, a structural component, and a secreted substrate (the invF, prgH, and sipA genes, respectively) was measured by using transcriptional reporter fusions to lacZ. β-Galactosidase activity was measured in the presence and absence of the compounds. A greater than 90% reduction in β-Galactosidase activity was observed for one or more of these fusions when cultures were grown in the presence of compound for four of these compounds, suggesting that these compounds specifically inhibited T3S transcription. In contrast, activity was similar in cultures grown in either the presence or absence of a thiazolidinone (Compound 1, as shown in FIG. 1), suggesting that this compound of the 92,000 screened might specifically target the assembly or structure of the *S. typhimurium* T3S.

Inhibition of *S. typhimurium* T3S. To demonstrate specific inhibition of T3S by the thiazolidinone, the culture supernatants of *S. typhimurium* was examined for T3S secreted substrates when grown in the presence of compound using Coomassie Blue-stained protein gels (FIG. 2A) and Western blots for the T3S proteins, SipA, B, and C (FIG. 2B).

Figure 2A:
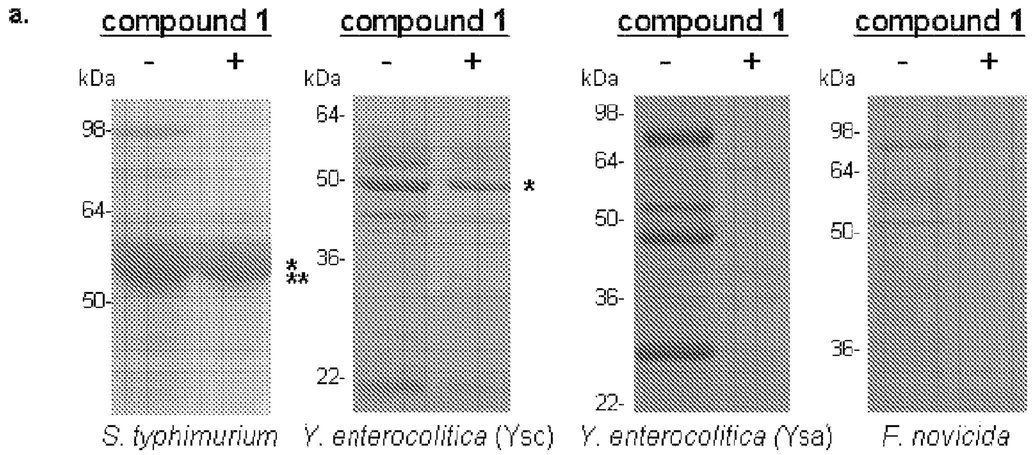
FIG. 2A is an image of SDS-PAGE gels of T3S secreted substances present in the culture supernatants of *S. typhimurium, Y. enterocolitica* (YSC), *Y. enterocolitica* (YSA), and *F. novicida;*

FIG. 2A is an image of SDS-PAGE gels of T3 secreted substances present in the culture supernatants of *S. typhimurium, Y. enterocolitica* (YSC), *Y. enterocolitica* (YSA), and *F. novicida*. Referring to FIG. 2A, bacterial cultures were grown in the presence (+) or absence (−) of 380 μM of Compound 1. Secreted proteins were TCA precipitated and separated by 12.5% SDS-PAGE and stained with Coomassie Blue. The flagellin proteins from *S. typhimurium* and *Y. enterocolitica* are marked (*), as well as the associated flagellar cap protein from *S. typhimurium* (**).

Figure 2B:
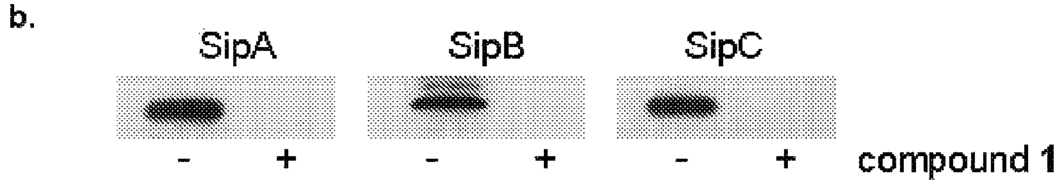
FIG. 2B is an image of a Western blot showing secreted proteins from *S. typhimurium* in the presence (+) and absence (−) of Compound 1.

FIG. 2B is an image of a Western blot showing secreted proteins SipA, B, and C, from *S. typhimurium* in the presence (+) and absence (−) of Compound 1. A marked decrease in the amount of the T3 secreted proteins was observed when bacterial cultures were grown in the presence of the thiazolidinone (Compound 1). To clearly rule out a complex T3S-dependent transcriptional effect, secretion of two T3S substrates, SipA and SspH1, were expressed from the T3S-independent lac promoter and their secretion examined by Western blot. Neither of these proteins was secreted from bacteria grown in the presence of the thiazolidinone.

Structure activity relationships established a chemotype that inhibits T3S. Thiazolidinones are a structural class associated with a variety of biological effects, that include antibacterial, antiviral, cardiotonic, and anti-inflammatory activities. The fact that the diverse and specific activities have been demonstrated for individual compounds from this family, which has a pluripotent common scaffold, suggests that the substituents are responsible for target selectivity. Using commercially available compounds, a preliminary structure activity relationship (SAR) study of thiazolidinone analogs was performed. Specifically, 45 compounds structurally related to Compound 1 were tested for inhibition of *S. typhimurium* SipA secretion by Western blot. The results showed that 40 of the 45 related compounds tested had some inhibitory activity on T3S, while the remaining compounds were unable to inhibit T3S. Table 1 shows the effect of nine thiazolidinone analogs on type III secretion in *S. typhimurium*.

TABLE 1

The effect of nine thiazolidinone analogs on type III secretion in *S. typhimurium*.

| Compound | Structure | % Secretion |
| --- | --- | --- |
| 1 | 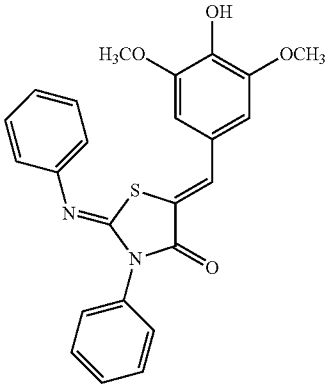 | 0 ± 0 |
| 2 | 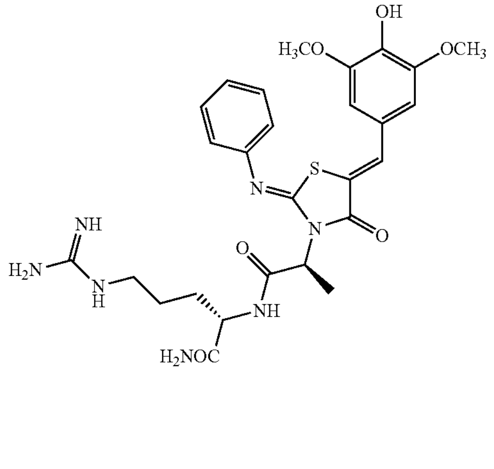 | 0 ± 0 |

TABLE 1-continued
| The effect of nine thiazolidinone analogs on type III secretion in *S. typhimurium*. | | |
|---|---|---|
| Compound | Structure | % Secretion |
| 3 | 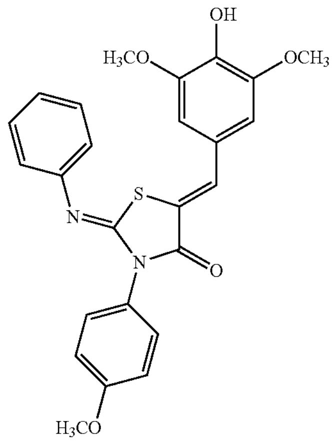 | 0 ± 0 |
| 4 | 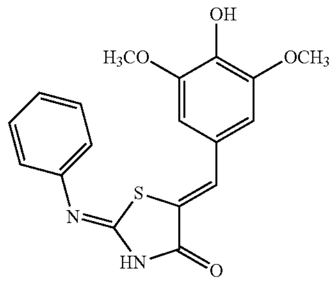 | 9 ± 6 |
| 5 | 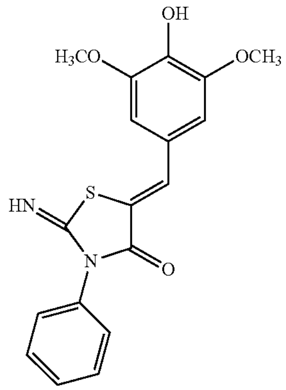 | 81.2 ± 0 |
| 6 | 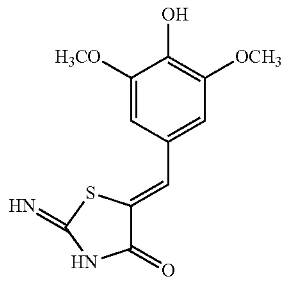 | 64 ± 4 |

TABLE 1-continued

The effect of nine thiazolidinone analogs on type III secretion in *S. typhimurium*.

| Compound | Structure | % Secretion |
|---|---|---|
| 7 | 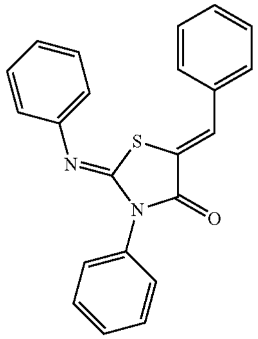 | 90 ± 2 |
| 8 | 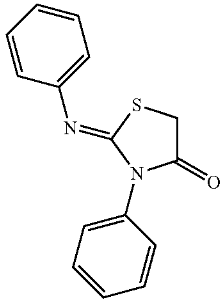 | 62 ± 3 |
| 9 | 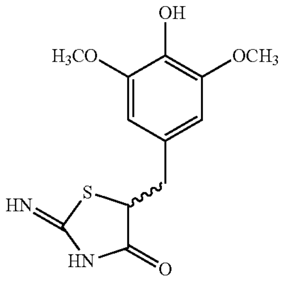 | 72 ± 0 |

In view of these data, the following conclusions can be drawn. First, these results are consistent with requirements for the imino nitrogen and the aryl group for inhibition of T3S (Compounds 5 and 6). Second, the 5-substituent likely must be a styryl group and reduction (Compounds 7 and 9) or removal (Compound 8) of this group significantly abrogates activity. Finally, the amido nitrogen is fairly permissive (Compounds 2, 3 and 4) and, thus, allows for the future evolution of increasingly active thiazolidinone analogs from this nitrogen.

To verify that there is a bona fide biological mechanism for inhibition of T3S by thiazolidinones, a dose-dependent curve was performed with Compound 1. Specifically, protein secretion by *S. typhimurium* was analyzed in the presence of 3.8 μM, 38 μM, and 380 μM of Compound 1. Secreted proteins were TCA precipitated, separated by SDS-PAGE and Western blotted with anti-SipA antibody.

Figure 2C:
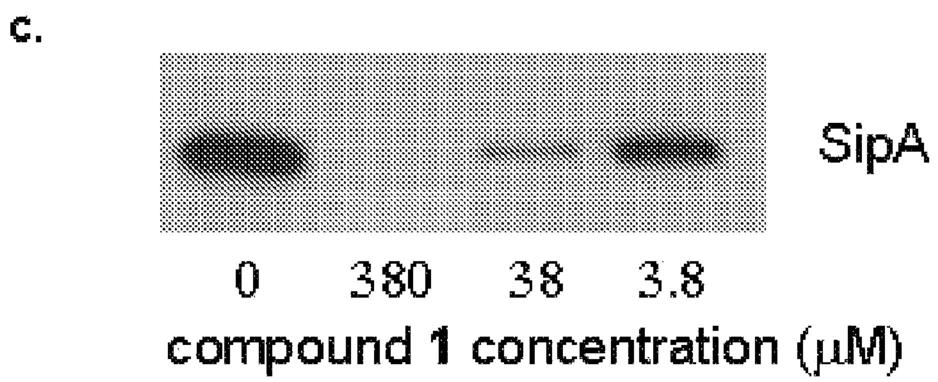
FIG. 2C is an image of a Western blot showing inhibition of SipA protein secretion in the presence of varying concentrations of Compound 1.

FIG. 2C is an image of a Western blot showing inhibition of SipA protein secretion in the presence of varying concentrations of Compound 1. Referring to FIG. 2C, the concentration of Compound 1 is, from left to right, 0 (lane 1); 380 μM (lane 2); 38 μM (lane 3); and 3.8 μM (lane 4). Inhibition of *S. typhimurium* protein secretion was greatest at 380 μM and diminished incrementally with decreasing concentration of compound. These data suggest that this compound specifically targets the T3S system in *S. typhimurium*. As complete inhibition of known T3S substrates was observed at 380 uM, this concentration was used in further experiments.

Because it was possible the poor solubility of Compound 1 contributes to its requirement for high micromolar concentration for full activity (380 μM), dose-dependent curves were performed for Compound 2 (Table 1, above), predicted to be much more soluble than Compound 1, with a predicted logP value of 1.66 as compared to a log P value of 4.87. Again, secreted proteins from *S. typhimurium* grown in the presence or absence of compound were TCA precipitated, separated by SDS-PAGE, and Western blotted with anti-SipA antibody.

Figure 2D:
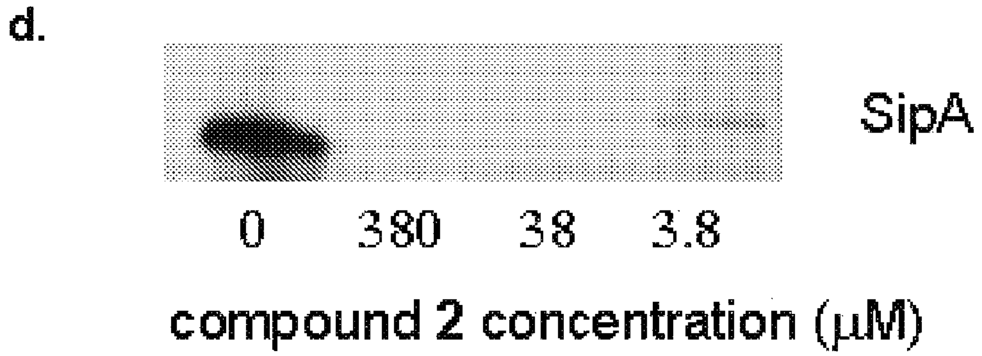
FIG. 2D is an image of a Western blot showing inhibition of SipA protein secretion in the presence of varying concentrations of Compound 2.

FIG. 2D is an image of a Western blot showing inhibition of SipA protein secretion in the presence of varying concentrations of Compound 2. Referring to FIG. 2D, the concentration of Compound 2 is, from left to right, 0 (lane 1); 380 μM (lane 2); 38 μM (lane 3); and 3.8 μM (lane 4). In contrast to Compound 1, the analog inhibited 100% of the detectable secreted SipA at 38 μM and minimal SipA was detected in the supernate at 3.8 μM (FIG. 2D). These data indicate that thiazolidinone compounds of higher activity can be generated and that hydrophobicity is not essential for activity.

Broad spectrum inhibitors of T3S systems. Phylogenetic analyses of conserved T3S systems indicate that these structures have evolved into different families typified by the Ysc system of *Yersinia* spp., the Inv/Spa system of *S. typhimurium* and *Shigella flexneri*, and the Esc system of enterohemorrhagic *E. coli* (EHEC) and the Hrp/Hrc system characteristic of plant pathogens such as *Pseudomonas syringae*. To examine the potential inhibitory effect of the compound on other classes of T3S systems, the secretion profiles for the T3S systems of *Yersinia enterocolitica* grown in the presence of the thiazolidinone were analyzed. The plasmid-encoded Ysc T3S system of *Yersinia pestis, Y. enterocolitica*, and *Yersinia pseudotuberculosis* represents a well characterized T3S system that delivers a set of bacterial effector proteins, termed Yops (Yersinia outer proteins) into the lumen of the target host cell resulting in inhibition of the innate immune response. In contrast, the chromosomally encoded Ysa T3S system of *Y. enterocolitica* secretes a set of proteins termed Ysps (*Yersinia* secreted proteins). Although translocation of these proteins into host cells has not been clearly demonstrated, it is believed to contribute to the gastrointestinal stage of infection. Both Yop and the Ysp proteins were absent in supernatants from *Y. enterocolitica* cultures grown in the presence of the thiazolidinone (FIG. 2A), indicating that these *Yersinia* T3S systems were also inhibited by thiazolidinones.

Inhibition of T3S needle complex assembly, without altering secretin protein levels or membrane localization. The highly conserved structure of the T3S apparatus includes a membrane-spanning complex associated with an extracellular needle, termed the needle complex (NC). The *S. typhimurium* secretin protein is required to form the NC. If thiazolidinones inhibited secretin insertion or polymerization in the outer membrane, and/or altered the stability of this protein, exposure of the bacteria to Compound 1 should reduce the amount of NC formed. Therefore, we isolated purified NCs from *S. typhimurium* cells grown in the presence and absence of Compound 1. The predominant NC proteins are InvG (the secretin protein), as well as PrgH and PrgK, which form a ring in the inner membrane. Post CsC1-gradients of NCs were separated by SDS-PAGE and analyzed by Western blot. An overall reduction in NC proteins was observed when cells were grown in the presence of Compound 1 (FIG. 3A), indicating that it inhibited formation and/or destabilized NCs. To further substantiate inhibition of NC formation or stability, electron micrographs (EMs) of negatively stained osmotically shocked *S. typhimurium* cells grown in the presence of Compound 1 were examined for the existence of needle structures. A marked reduction in NC number was observed on the surface of cells grown in the presence of compound.

Figure 3A:
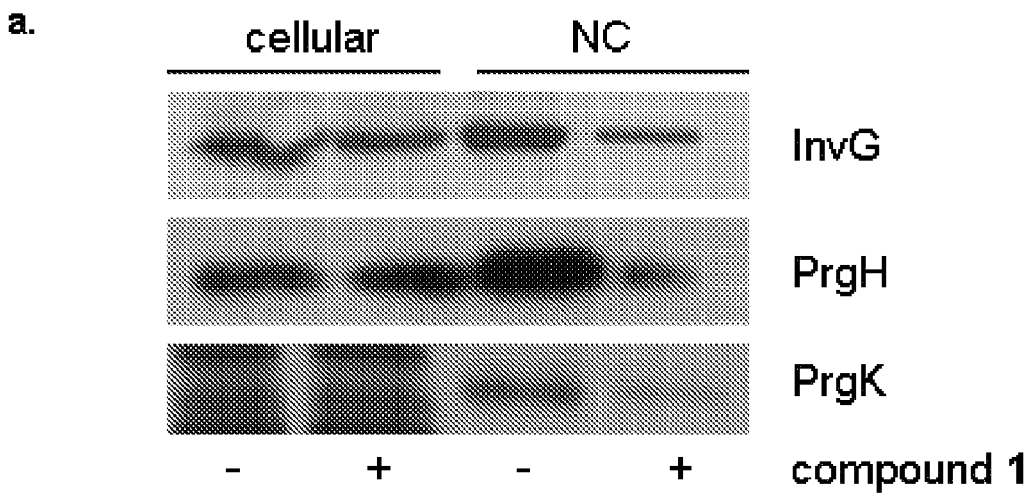
FIG. 3A is an image of a Western blot showing type III secretion needle complex proteins isolated from *S. typhimurium* grown in the presence (+) or absence (−) of 380 μM of Compound 1.
Figure 3B:
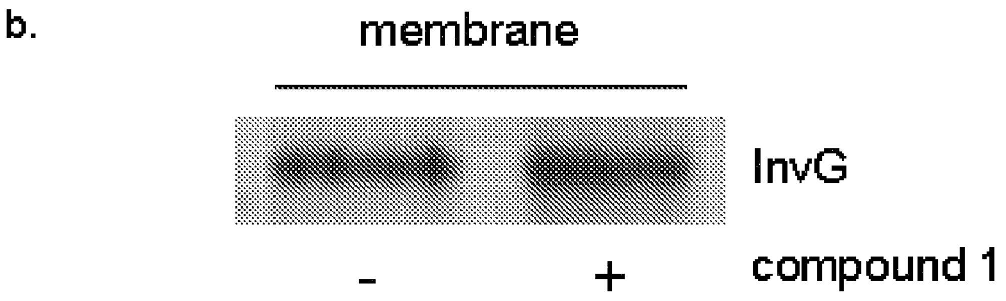
FIG. 3B is an image of a Western blot showing membrane fractions of *S. typhimurium* grown in the presence (+) or absence (−) of 380 μM of Compound 1.

To test whether the decrease in NCs resulted from a reduction in either cellular levels of NC proteins or localization of these proteins to the membrane, cells grown in the presence and absence of Compound 1 were assayed for the abundance and localization of the secretin protein InvG. FIG. 3A is an image of a Western blot of type III secretion NC proteins isolated from *S. typhimurium* grown in the presence (+) or absence (−) of 380 μM of Compound 1. FIG. 3B is an image of a Western blot of membrane fractions of *S. typhimurium* grown in the presence (+) or absence (−) of 380 μM of Compound 1. In the presence of Compound 1, InvG cellular levels and bacterial membrane localization were unaltered (FIGS. 3A and 3B). Similarly, protein levels and localization of the other NC proteins PrgH and PrgK were unchanged. These data indicate that Compound 1 either inhibits NC formation and/or its stability. Given that stable and equal amounts of InvG, PrgH, and PrgK are present in the membrane and the marked stability of the NC to a variety of harsh conditions, such as high pH, these data favor a model in which NC assembly is inhibited. These data indicate that the NC is the target of Compound 1 and its effect is most likely mediated by inhibition of assembly of this multi-protein polymeric complex.

Overall, it appears that thiazolidinones are either inhibiting the assembly of this oligomeric structure or destabilizing the assembled structure. Because this structure is highly stable, it is more likely that Compound 1 is inhibiting the assembly of the secretin complex. For example, these small molecules could act by inhibiting protein-protein interactions that catalyze and/or mediate secretin oligomerization. In many systems the secretin has a dedicated lipoprotein that appears to function to promote insertion and polymerization of the ring in the outer membrane. As these proteins are not highly conserved and have not been identified for all secretion systems, including the Ysa T3S system of *Y. enterocolitica* analyzed in this work, it is more likely that thiazolidinones are targeting the secretin protein itself rather than this accessory molecule.

Inhibition of the secretin utilizing T4P systems, but not the flagellar T3S system that is secretin-independent. T3S systems are evolutionarily related to the flagellar-specific T3S system. Interestingly, while a core of eight conserved proteins assemble the foundation of T3S apparatus, as well as the flagellar system, the flagellar system does not utilize a secretin protein. Therefore, if our compound targets secretins, it should not affect the flagellar system. To determine the effect of the thiazolidinone on flagellar function, motility was measured in its presence. A motility assay of *S. typhimurium* in the presence (+) or absence (−) of 380 μM of Compound 1 was conducted. *S. typhimurium* motility was unaffected by Compound 1. In addition, secretion of flagellin, the predominant substrate of this system, was unaltered (FIG. 2A).

In contrast, twitching motility in *Pseudomonas aeruginosa* is a flagellum-independent form of bacterial motility and is mediated by T4P, which require a secretin protein for assembly. The secretin is the only shared component with T3S systems and, therefore, if our compound is indeed targeting secretins, it should also inhibit T4P assembly. A twitching assay of *P. aeruginosa* in the presence (+) or absence (−) of 380 μM of Compound 1 was conducted. Growth media was removed, and the bacteria were stained with crystal violet. *P. aeruginosa* twitching motility was significantly reduced in motility plates containing the compound. These data suggest that thiazolidinones block the assembly and/or stability of diverse secretin complexes.

Inhibition of T2S of *Francisella* and *Pseudomonas* species. Recently, *Francisella novicida*, a subspecies of *F. tularensis*, the causative agent of the zoonotic disease tularemia, was demonstrated to secrete a number of virulence factors through an uncharacterized novel secretion system related to T4P secretion systems, which share a number of structural components with T2S systems. *Francisella* secretion was shown to require a protein with amino acid similarity to secretins. To further examine the ubiquitous nature of thiazolidinone inhibition, secretion of virulence proteins by *F. novicida* when grown in the presence of Compound 1 was analyzed using Coomassie Blue-stained protein gels (FIG. 2A). Compound 1 inhibited secretion of the known *Francisella* virulence proteins, further indicating that the thiazolidinone targets the assembly and/or stability of diverse secretin complexes in the bacterial membrane.

Bacterial T2S systems transport many substrates from the periplasm across the outer membrane, including a variety of mammalian toxins, as well as other proteins that degrade host cell components, such as proteins, lipids, and sugars of the extracellular matrix. For example, an important virulence factor of the opportunistic pathogen *P. aeruginosa* is the T2 secreted extracellular enzyme elastase, which is required for the ability of this organism to produce corneal ulcers, skin infections, and pneumonia. As with T3S and T4P assembly, secretins are essential for T2S.

To determine if the thiazolidinone inhibits the T2-dependent secretion of elastase, elastase activity in culture supernates was measured from bacteria grown in the presence and absence of Compound 1. An elastolytic activity assay for 18 hour cultured supernatants of *P. aeruginosa* grown in the absence (PAO1) or presence of 380 μM Compound 1 (PAO1-C) was conducted. Elastolytic activity was determined using elastin Congo red as a substrate. As a negative control elastase activity was determined for the culture supernate of *P. aeruginosa* T2S mutant (pilD). The $OD_{495}$ of the samples was as follows. PAO1: 1.881; PAO1-C: 0.437; and pilD: 0.098. A dramatic reduction in supernatant elastolytic activity was observed when bacteria were grown in the presence of Compound 1, indicating that Compound 1 inhibits T2S, as well as T3S and T4P assembly, most likely by acting upon the secretin.

Protection of macrophages against *S. typhimurium* induced T3-dependent cytotoxicity. Although it was shown that thiazolidinones inhibited in vitro T3S, inhibition of T3 translocation into eukaryotic cells was also examined. To determine whether Compound 1 blocked T3 translocation of virulence determinants into host cells and, thus, inhibits microbial virulence function, cytotoxicity of bone marrow macrophages by *S. typhimurium* was measured in the presence of Compound 1. The enteric pathogens *Salmonella* and *Shigella* stimulate caspase-1 mediated cell death as a result of T3S-mediated translocation. Bacteria were added at a multiplicity of 40, and *S. typhimurium* cytotoxicity to macrophages was measured by monitoring the release of lactate dehydrogenase, a stable cytosolic enzyme that is released upon macrophage lysis. Assays were performed in quadruplicate.

Figure 4A:
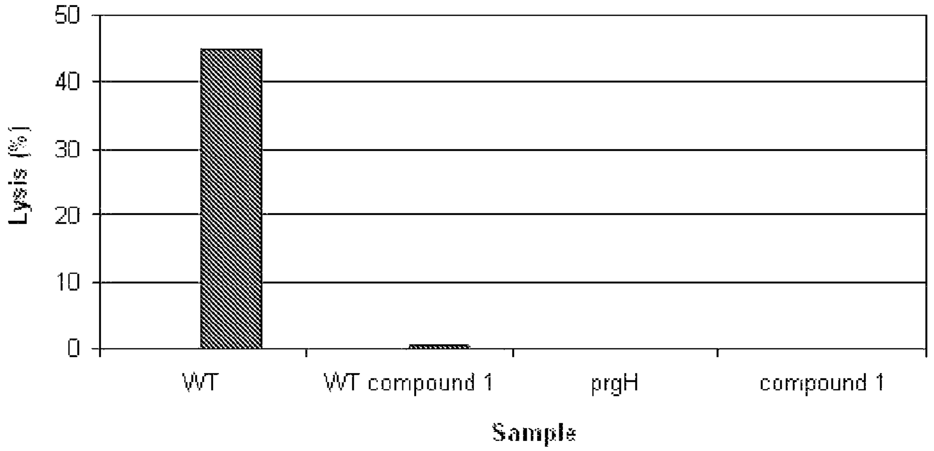
FIG. 4A is a graph showing percent lysis of variously infected bone marrow macrophages.

FIG. 4A is a graph showing lysis of bone marrow macrophages. Referring to FIG. 4A, bacteria were grown in the absence or presence of Compound 1 under T3S-inducing conditions and added to macrophages. See FIG. 4A, columns labeled WT and WT Compound 1, respectively. A significant decrease in caspase-1 dependent cell death of macrophages, 40% to 0.5%, was observed for bacteria grown in the presence of Compound 1, consistent with the protection of mammalian cells from bacterial virulence in a tissue culture model of infection. In addition, Compound 1 was added directly to macrophages at a concentration equal to the sample with bacteria and Compound 1. See FIG. 4A, column labeled "Compound 1." Macrophages exposed to Compound 1 did not lyse suggesting that Compound 1 is not cytotoxic to mammalian cells. As a negative control a prgH mutant, an essential structural component of the T3S apparatus, was added to macrophages. See FIG. 4A, column labeled "prgH-."Cytotoxicity of macrophages was not observed with the *S. typhimurium* T3S genetic mutant.

Inhibition of T3S-dependent pathogenesis of the plant pathogen, *Pseudomonas syringae* pv tomato DC3000 for tobacco. The bacterial plant pathogen *Pseudomonas syringae* pv tomato DC3000 requires T3S of virulence determinants to cause disease. The hypersensitivity response (HR) elicited by *P. syringae* in non-host tobacco plants depends upon a functional T3S system, representing an established virulence model for this pathogen. To determine the effect of Compound 1 on *P. syringae* pathogenesis for plants, overlapping infiltrations of *P. syringae* and Compound 1 were performed. *P. syringae* was inoculated on non-host tobacco plants and monitored for HR. Bacterial inoculations partially overlapped inoculations of either 380 μM of Compound 1 or the solvent DMSO. HR was measured by tissue collapse of plants cells in the overlapping region.

Figure 4B:
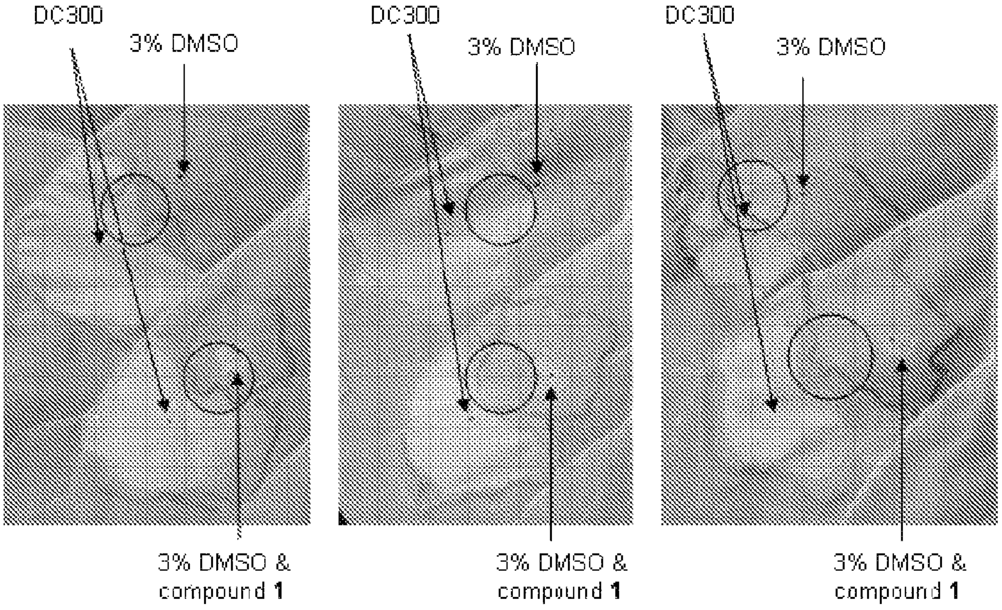
FIG. 4B is a set of images depicting tobacco plants following inoculation with *P. syringae.*

FIG. 4B shows three separate experiments with the regions of overlap circled. Referring to FIG. 4B, *P. syringae* exhibited a reduced ability to elicit HR in the presence of compound compared with solvent alone. Therefore, these compounds, which blocked disease in an important model of plant pathogenesis, may have utility in preventing disease of plants. Overall, these results indicate that the thiazolidinone family of compounds can inhibit a wide variety of T2S and T3S systems and can block the delivery of many virulence proteins, likely preventing disease in diverse types of bacterial infections.

Table 2 provides the sequence name, sequence description, and SEQ ID NO for the above-referenced SEQ ID NOS. 1-4.

TABLE 2

Sequence information for SEQ ID NOS. 1-4.

| Sequence Name | Sequence Description | SEQ ID NO: |
|---|---|---|
| SipA polypeptide sequence | *S. typhimurium* T3S substrate | 1 |
| SipA nucleotide sequence | *S. typhimurium* T3S substrate | 2 |
| YplA polypeptide sequence | *Y. enterocolitica* T3S substrate | 3 |
| YplA nucleotide sequence | *Y. enterocolitica* T3S substrate | 4 |

In another aspect, the invention provides a method for inhibiting Gram-negative bacterial pathogenesis. In the method, Gram-negative bacterial pathogenesis is inhibited by administering an effective amount of a thiazolidinone compound to a subject in need thereof. The thiazolidinone compound is a 4-thiazolidinone, preferably a 5-arylidene-2-imino-4-thiazolidinone compound.

In one embodiment, the method for inhibiting Gram-negative bacterial pathogenesis comprises administering an effective amount of a compound to a subject in need thereof, the compound having the formula:

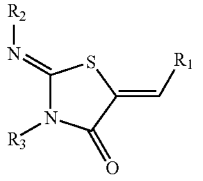

wherein, $R_1$ is selected from:

(a) substituted and unsubstituted aryl, (b) substituted and unsubstituted heteroaryl, (c) substituted and unsubstituted alkyl, and (d) substituted and unsubstituted cycloalkyl;

$R_2$ is substituted or unsubstituted aryl; and $R_3$ is selected from:

(a) hydrogen, (b) substituted or unsubstituted alkyl, (c) substituted or unsubstituted cycloalkyl, (d) substituted or unsubstituted aryl, (e) substituted or unsubstituted heteroaryl, (f) —CH($R_4$)—W—Y, wherein W is selected from (i) Q-CH($R_5$), wherein $R_4$ and $R_5$ are independently selected from natural and non-natural amino acid side chains, and Q is selected from —C(=O)NH—, —C(=O)O—, —$SO_2$NH—, and —P(O)($OR_8$)NH—, wherein $R_8$ is selected from hydrogen and substituted or unsubstituted alkyl, or (ii) $C(=O)NR_6CH(R_7)$, wherein $R_6$ and $R_7$ taken together with the carbon and the nitrogen atoms to which they are attached form a 5- to 7-membered ring that optionally includes one or more heteroatoms, and wherein Y is selected from $—C(=O)NH_2$, $—C(=O)OH$, $—SO_2NH_2$, and $—P(O)(OR_8)NH_2$, wherein $R_8$ is selected from hydrogen and substituted or unsubstituted alkyl, and (g) $—(CH_2)_nN(R_9)X(CH_2)_mR_{10}$, wherein n is an integer from 1 to 8, m is an integer from 1 to 8, X is selected from $C(=O)$, $N(C=O)OH$, $N(C=NH)NH$, and $CH_2$, $R_9$ is hydrogen or substituted or unsubstituted alkyl, and $R_{10}$ is heterocyclyl.

In one embodiment, $R_1$ is selected from phenyl and substituted phenyl. In one embodiment, $R_1$ is phenyl substituted at one or more of positions 3, 4, and 5 positions with one or more of $—OR_{11}$, $—NR_{11}R_{12}$, $—SR_{11}$, and halogen, wherein $R_{11}$ and $R_{12}$ are independently selected from:

(a) hydrogen, (b) substituted and unsubstituted alkyl, (c) substituted and unsubstituted cycloalkyl, (d) substituted and unsubstituted aryl, (e) substituted and unsubstituted heteroaryl, and (f) $—C(=O)R_{13}$, wherein $R_{13}$ is selected from hydrogen, substituted and unsubstituted alkyl, and substituted and unsubstituted aryl.

In one embodiment, $R_1$ is 4-hydroxy-3,5-dimethoxyphenyl. In one embodiment, $R_1$ is morpholinocarbamoylphenyl.

In one embodiment, $R_2$ is selected from phenyl and substituted phenyl.

In one embodiment, $R_3$ is phenyl or substituted phenyl. In one embodiment, $R_3$ is aminoalkyl. In one embodiment, $R_3$ is $—CH(R_4)\text{-}Q\text{-}CH(R_5)—Y$, and Q is $—C(=O)NH—$ and Y is $—C(=O)NH_2$.

In another embodiment, the method for inhibiting Gram-negative bacterial pathogenesis comprises administering an effective amount of a compound to a subject in need thereof, the compound having the formula:

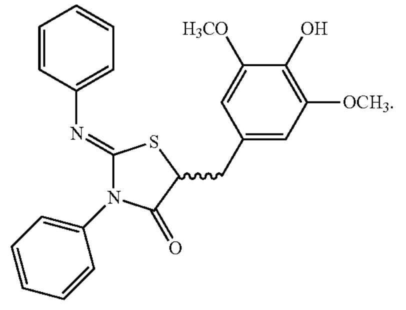

In another aspect of the invention, compounds that inhibit Gram-negative bacterial pathogenesis are provided. The preparation and properties of representative compounds of the invention are described in Example 6.

In one embodiment, the compounds have formula (I):

(I)

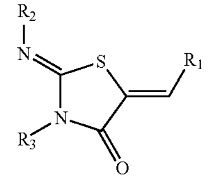

wherein, $R_1$ is selected from:

(a) substituted and unsubstituted aryl, (b) substituted and unsubstituted heteroaryl, (c) substituted and unsubstituted alkyl, and (d) substituted and unsubstituted cycloalkyl;

$R_2$ is substituted or unsubstituted aryl; and $R_3$ is selected from:

(a) $—CH(R_4)—W—Y$, wherein W is selected from (i) $Q\text{-}CH(R_5)$, wherein $R_4$ and $R_5$ are independently selected from natural and non-natural amino acid side chains, and Q is selected from $—C(=O)NH—$, $—C(=O)O—$, $—SO_2NH—$, and $—P(O)(OR_8)NH—$, wherein $R_8$ is selected from hydrogen and substituted or unsubstituted alkyl, and (ii) $C(=O)NR_6CH(R_7)$, wherein $R_6$ and $R_7$ taken together with the carbon and the nitrogen atoms to which they are attached form a 5- to 7-membered ring that optionally includes one or more heteroatoms, and wherein Y is selected from $—C(=O)NH_2$, $—C(=O)OH$, $—SO_2NH_2$, and $—P(O)(OR_8)NH_2$, wherein $R_8$ is selected from hydrogen and substituted or unsubstituted alkyl, and (b) substituted or unsubstituted C1-C10 alkyl, with the proviso that when $R_3$ is C1-C3 alkyl, $R_3$ further includes a heteroatom selected from O, N, and S.

In one embodiment, $R_3$ is aminoalkyl. In one embodiment, $R_3$ is $—CH(R_4)\text{-}Q\text{-}CH(R_5)—Y$, and Q is $—C(=O)NH—$, and Y is $—C(=O)NH_2$.

In another embodiment, the compounds that inhibit Gram-negative bacterial pathogenesis have formula (II):

(II)

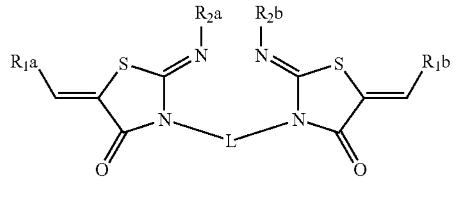

wherein, $R_{1a}$ and $R_{1b}$ are independently selected from:

(a) substituted and unsubstituted aryl, (b) substituted and unsubstituted heteroaryl, (c) substituted and unsubstituted alkyl, and (d) substituted and unsubstituted cycloalkyl;

$R_{2a}$ and $R_{2b}$ are independently is selected from:

(a) hydrogen, (b) substituted or unsubstituted aryl, and (c) substituted and unsubstituted heteroaryl; and L is a linker moiety having at least six atoms.

In one embodiment, $R_{1a}$ is 3,5-dimethoxy-4-hydroxyphenyl. In one embodiment, $R_{1b}$ is 3,5-dimethoxy-4-hydroxyphenyl. In another embodiment, $R_{1a}$ is 3,5-dimethoxy-4-hydroxyphenyl and $R_{1b}$ is 3,5-dimethoxy-4-hydroxyphenyl.

In one embodiment, $R_{2a}$ is phenyl. In one embodiment, $R_{2b}$ is phenyl. In another embodiment, $R_{2a}$ is phenyl and $R_{2b}$ is phenyl.

In one embodiment, L includes an amide linkage. In one embodiment, L is $-(CH_2)_n-C(=O)NH-(CH_2)_m-$, wherein n is an integer from 1 to 3 and m is an integer from 2 to 6.

The following definitions are provided.

"Alkyl" refers to alkyl groups that do not contain heteroatoms. The phrase includes primary alkyl groups, secondary alkyl groups, and tertiary alkyl groups. Therefore, the phrase includes straight chain alkyl groups such as methyl, ethyl, propyl, butyl, pentyl, hexyl, heptyl, octyl, nonyl, decyl, undecyl, dodecyl and the like, and branched chain isomers of straight chain alkyl groups. In addition, the phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Preferred alkyl groups include straight and branched chain alkyl groups and cyclic alkyl groups having 1 to 12 carbon atoms. "Alkylene" refers to the same residues as noted herein for "alkyl," but having two points of attachment, (i.e., being divalent).

"Alkenyl" refers to straight chain, branched, or cyclic radicals having one or more carbon-carbon double bonds and from 2 to about 20 carbon atoms. Preferred alkenyl groups include straight chain and branched alkenyl groups and cyclic alkenyl groups having 2 to 12 carbon atoms. "Alkenylene" refers to the same residues noted herein for "alkenyl," but having two points of attachment (i.e. divalent).

"Alkynyl" refers to straight chain, branched, or cyclic radicals having one or more carbon-carbon triple bonds and from 2 to about 20 carbon atoms. Preferred alkynyl groups include straight chain and branched alkynyl groups having 2 to 12 carbon atoms. "Alkynylene" refers to the same residues noted herein for "alkynyl," but having two points of attachment (i.e. divalent).

"Aryl" refers to monocyclic and polycyclic aromatic groups having from 3 to 14 backbone carbon and all ring atoms in the aromatic ring are carbon.

"Heteroaryl" refers herein to monocyclic and polycyclic aromatic groups having from 1 to 4 heteroatoms as ring atoms in an aromatic ring with the remainder of the ring atoms being carbon atoms.

"Substituted" refers to a group as defined above in which one or more bonds to a carbon(s) or hydrogen(s) are replaced by a bond to non-hydrogen and non-carbon atoms such as, but not limited to, a halogen atom, such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted groups also include groups in which one or more bonds to a carbon(s) or hydrogen(s) atom is replaced by a higher-order bond, such as a double- or triple-bond, to a heteroatom such as oxygen in oxo, carbonyl, carboxyl, and ester groups; nitrogen in groups such as imines, oximes, hydrazones, and nitriles. Substituted groups further include groups in which one or more bonds to a carbon(s) or hydrogen(s) atoms is replaced by a bond to an aryl, heteroaryl, heterocyclyl, or cycloalkyl group.

In another aspect, the invention provides compositions for inhibiting Gram-negative bacterial pathogenesis. The composition of the invention includes one or more compounds of the invention (e.g., a compound having formula (I) or (II)).

In one embodiment, the compounds of the invention may be formulated into a composition that additionally comprises suitable pharmaceutically acceptable carriers, including excipients and other compounds that facilitate administration to a mammalian subject. Further details on techniques for formulation and administration may be found in the latest edition of "Remington's Pharmaceutical Sciences" (Mack Publishing Co, Easton, Pa.).

Compositions for oral administration may be formulated using pharmaceutically acceptable carriers well known in the art, in dosages suitable for oral administration. Such carriers enable the compositions containing compounds of the invention to be formulated as tablets, pills, dragees, capsules, liquids, gels, syrups, slurries, suspensions, etc., suitable for ingestion by a subject. Compositions for oral use may be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins, such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Compositions for oral administration may be formulated, for example, as push-fit capsules made of gelatin, as well as soft, sealed capsules made of gelatin and a coating such as glycerol or sorbitol. Push-fit capsules may contain the compounds of the invention mixed with filler or binders such as lactose or starches, lubricants such as talc or magnesium stearate, and, optionally, stabilizers. In soft capsules, the compounds of the invention may be dissolved or suspended in suitable liquids, such as fatty oils, liquid paraffin, or liquid polyethylene glycol with or without stabilizers.

Compositions for parenteral administration include aqueous solutions of one or more compounds of the invention. For injection, the compounds may be formulated in aqueous solutions, such as in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of the compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents, which increase the solubility of the compounds to allow for the preparation of highly concentrated solutions.

For topical or nasal administration, penetrants appropriate to the particular barrier to be permeated are typically used in the formulation. Examples of these are 2-pyrrolidone, N-methyl-2-pyrrolidone, dimethylacetamide, dimethyl-formamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. For topical administration, the composition may be in the form of a transdermal ointment or patch for systemic delivery of the compound and may be prepared in a conventional manner (see, e.g., Barry, Dermatological Formulations (Drugs and the Pharmaceutical Sciences-Dekker); Harrys Cosmeticology (Leonard Hill Books).

For rectal administration, the compositions may be administered in the form of suppositories or retention enemas. Such compositions may be prepared by mixing the compounds of the invention with a suitable non-irritating excipient that is solid at ordinary temperatures but liquid at the rectal temperature and will therefore melt in the rectum to release the drug. Suitable excipients include, but are not limited to, cocoa butter and polyethylene glycols.

The amounts of each of these various types of additives will be readily apparent to those skilled in the art, optimal amounts being the same as in other, known formulations designed for the same type of administration. Stratum corneum penetration enhancers, for example, will typically be included at levels within the range of about 0.1% to about 15%.

Compositions containing the compounds of the invention may be manufactured in a manner similar to that known in the art (e.g., by means of conventional mixing, dissolving, granulating, dragee-making, levigating, emulsifying, encapsulating, entrapping or lyophilizing processes). The compositions may also be modified to provide appropriate release characteristics, e.g., sustained release or targeted release, by conventional means (e.g., coating).

Compositions containing the compounds may be provided as a salt and can be formed with many acids, including but not limited to hydrochloric, sulfuric, acetic, lactic, tartaric, malic, and succinic. Salts tend to be more soluble in aqueous or other protonic solvents than are the corresponding free base forms.

After compositions formulated to contain the compounds of the invention and an acceptable carrier have been prepared, they can be placed in an appropriate container and labeled for use.

These administration methods are applicable to any animal subject, such as a human subject. For example, a subject in need of compositions comprising a compound of the invention may be a patient. Accordingly, the invention provides methods for inhibiting Gram-negative bacterial pathogenesis by administering to a human or animal subject in need thereof an effective amount of a compound of invention.

Effective amounts of the compound will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration.

The amount of the compound of the invention actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the compounds of the invention may be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $LD_{50}$ to $ED_{50}$. Compounds that exhibit large therapeutic indices are particularly suitable in the practice of the methods of the invention. The data obtained from cell culture assays and animal studies may be used in formulating a range of dosage for use in humans or other mammals. The dosage of such conjugates lies preferably within a range of circulating concentrations that include the $ED_{50}$ with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The compounds of the invention may be administered alone, or in combination with one or more additional therapeutically active agents.

The following examples are provided for the purposes of illustrating, not limiting, the invention.

EXAMPLES

Example 1

Strain Construction and Bacterial Growth Conditions

*Salmonella, Yersinia*, and *Pseudomonas* strains were grown in Luria Bertani (LB) medium, while *Francisella* was grown in Tryptic Soy Broth supplemented with 0.1% cysteine and 0.2% glucose. Motility media was made as described in Maloy, S. R., et al., *Genetic Analysis of Pathogenic Bacteria: A Laboratory Manual*, Cold Spring Harbor Laboratory Press (1996); and Semmler, A. B. T., et al., *Microbiology* 145 (1999). For cytotoxicity assays, *Salmonella* strains were grown overnight and diluted 1:40 (v/v) and were grown for 3 hours to induce T3S gene expression. For all experiments, unless indicated otherwise, Compound 1 was used at a concentration of 380 μM. Bacterial strains were constructed using P22HT int transduction and the λ RED system.

Example 2

Screening

To perform the screening, 30 μl of LB with bacteria (diluted 1:100 from an overnight culture) were aliquoted into 384-well black bottom plates, approximately 1 μl of compounds were arrayed into wells (approximate concentrations of 5 mg/ml in DMSO), and plates were incubated overnight at 37° C. The next day, 30 μl of PLA buffer (10 mM Tris HCl pH8.0, 100 mM NaCl, 10 mM $CaCl_2$) with PED6 was aliquoted to each well and plates were incubated at room temperature RT for 4 hours. Fluorescence was read at 515 nm. Screening was performed at the National Screening Laboratory for the Regional Centers of Excellence in Biodefense and Emerging Infectious Disease (Boston, Mass.).

Example 3

Enzymatic Assays

β-Galactosidase and alkaline phosphatase assays were performed following the protocols as described in Maloy, S. R., et al., *Genetic Analysis of Pathogenic Bacteria: A Laboratory Manual*, Cold Spring Harbor Laboratory Press (1996). These experiments were performed in triplicate and the averages of three independent experiments were recorded as percent wild-type. Elastase assays were performed as described in McIver, K. S., et al., *Microbiology* 150, 3969-3977 (2004); and Ohman, D. E., et al., *J. Bacteriol.* 184, 1324-1334 (1980).

Example 4

Protein Chemistry

Secreted proteins were prepared, as previously described, for *S. typhimurium* (Kimbrough, T. G., and Miller, S. I., *Proc. Natl. Acad. Sci.* 97, 11008-11013 (2000), *Y. enterocolitica* (Young, B. M., and Young, G. M., *J. Bacteriol.* 184, 1324-1334 (2002), and *F. novicida* (Hager, A. J., et al., *Mol. Microbiol.* 62, 227-237 (2006). T3S needle complexes were isolated from *S. typhimurium*, as described in Kimbrough, T. G., and Miller, S. I., *Proc. Natl. Acad. Sci.* 97, 11008-11013 (2000). SDS/PAGE and Western blot techniques were performed as described in Pegues, D. A., et al., *Mol. Microbiol.* 17, 169-181 (1995).

Example 5

Virulence Studies

For cytotoxicity assays, bone marrow macrophages (BMMs) were plated and infected the following day. *S. typhimurium* was added at a multiplicity of infection (MOI) of 40, were diluted in 100 μl media, and added to BMMs. Infections were allowed to proceed for 30-minutes at 37° C. in an atmosphere of 5% $CO_2$. Lactate dehydrogenase (LDH) activity was measured on 50 μl of supernate using the CytoTox 96 assay (Promega). Each sample was done in quadruplicate and the average values shown. The results are also representative of two independent experiments. For the HR assays, a blunt end syringe was used to inject approximately 100 μl of solvent (3% DMSO, 10 mM $MgCl_2$) or 166.67 μg/ml Compound 1 in solvent into three week old *Nicotiana tabacum* cv. *Xanthi* leaves and the infiltrated area was marked. Subsequently, approximately 100 μl of $1\times10^7$ CFU/ml of DC3000 in 10 mM $MgCl_2$ was injected into the leaves, such that the infiltration zone overlapped with the previous inoculation. Leaves were photographed at 24 hours post-injection. Inoculations were performed on multiple leaves from different plants and results presented are representative of these experiments.

Example 6

The Preparation and Properties of Representative T3S Inhibitors

In this example, the preparation and properties of representative T3S inhibitors of the invention are described.

General Methods. All reactions were run under an atmosphere of dry nitrogen. Reagents and solvents were obtained in the highest available purity and used without further purification unless indicated. $^1$H NMR spectra were obtained on a 300 MHz (Bruker AV300 or AV301) or 500 MHz (Bruker AV500 or Varian) instrument. $^{13}$C NMR spectra were obtained on a 500 MHz Bruker AV500. Low resolution mass spectra were obtained on a Bruker Esquire LC ion trap. Accurate mass determinations were run on a Bruker APEX Qe 47 Fourier transformed ion cyclotron resonance mass spectrometer (Bruker Daltronics, Billerica, MAJ) equipped with a capillary flow injection system and operated in the positive ion ESI mode. Normal phase silica gel purifications were done using a Biotage SP4 instrument using the cartridges supplied by Biotage. RP-HPLC was done on a Varian instrument equipped with a diode array ultraviolet detector. For preparative reverse phase chromatography a 10×250 mm C18 5 m column at a flow rate of 4.6 mL/min was used; for analytical reverse phase chromatography a 4.6×250 C18 5 m column at a flow rate of 1 mL/min was used. Ultraviolet detection was at 215 and either 260 or 360 nm. Unless otherwise specified, buffer A was 0.05% TFA in $H_2O$, buffer B was 0.05% TFA in acetonitrile. Thin layer chromatography was done using 0.2 mm polygram SIL G/UV plates (Alltech, Deerfield, Ill.) or Si250F (J. T Baker, Phillipsburg, N.J.) plates, developed using mobile phases of varying compositions of ethyl acetate/hexane, MeOH/$CH_2Cl_2$, or MeOH/$CHCl_3$, and visualized by UV light supplemented by vanillin, ninhydrin, and other solution stains where appropriate.

Synthetic Methods: Schemes I-III. Synthetic methods for thiazolidinones are well described in the literature. The syntheses of the aminohexyl and aminomethylphenyl analogs is shown in Scheme I.

Scheme I.

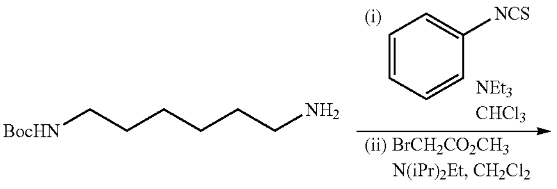

-continued

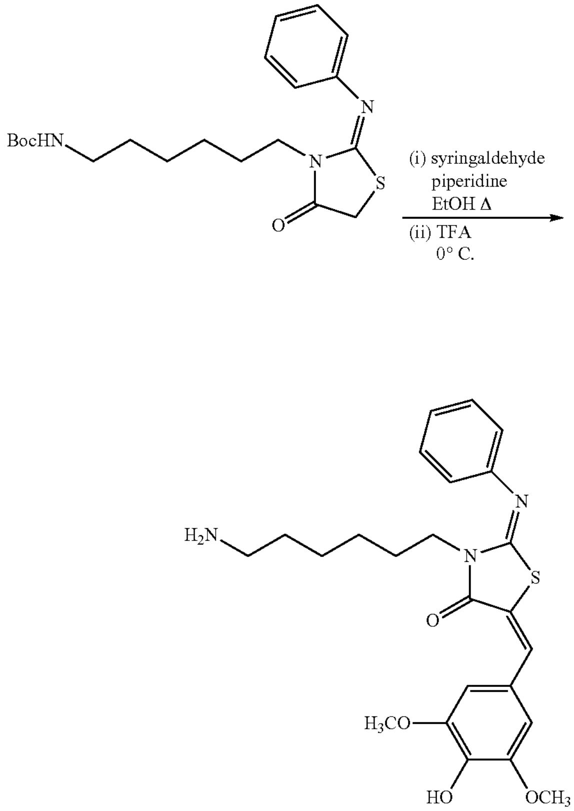

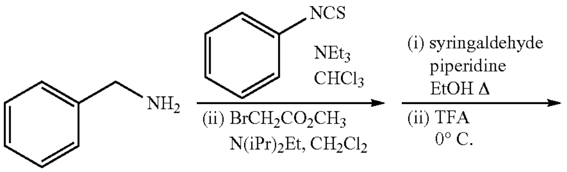

-continued

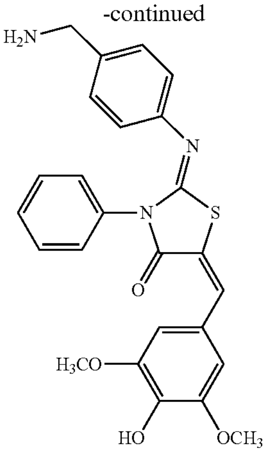

and

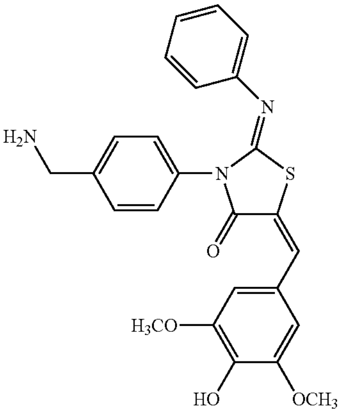

The general method of Scheme I was used to generated the compounds in Tables 3 and 4.

Short peptides are an expeditious way to survey functional groups, stereochemistry, and molecular shape. In Scheme II, one synthetic method used to generate N3-dipeptide examples of the 2-imino-5-arylidene thiazolidinones (Table 5) is illustrated.

Scheme II.

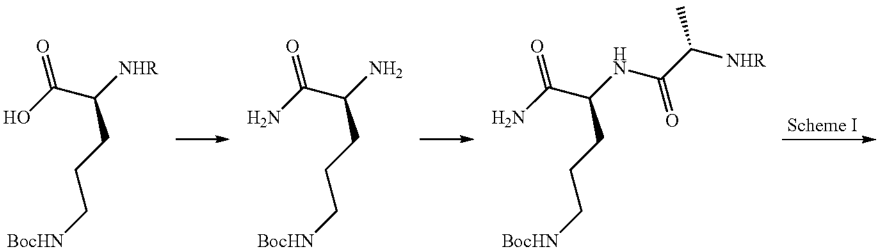

R = Cbz
R = H

-continued
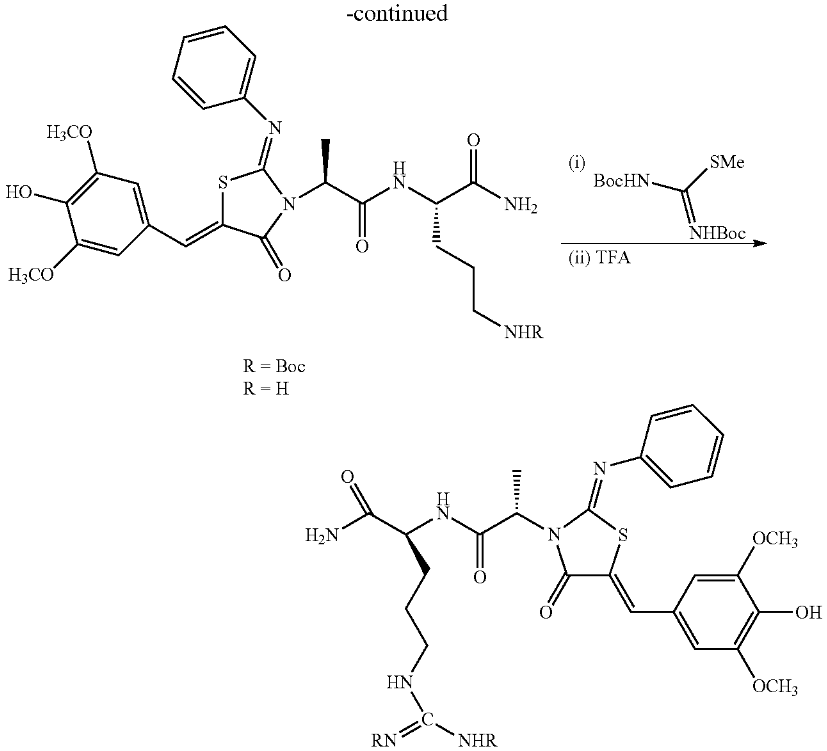
R = Boc
R = H
R = Boc
R = H
Alternatively, as shown in Scheme III, a solid phase route to the N3-dipeptide 2-imino-5-arylidene thiazolidinones shown in Table 5 is demonstrated. Yields and purities were comparable to those obtained in solution chemistry.
Scheme III.
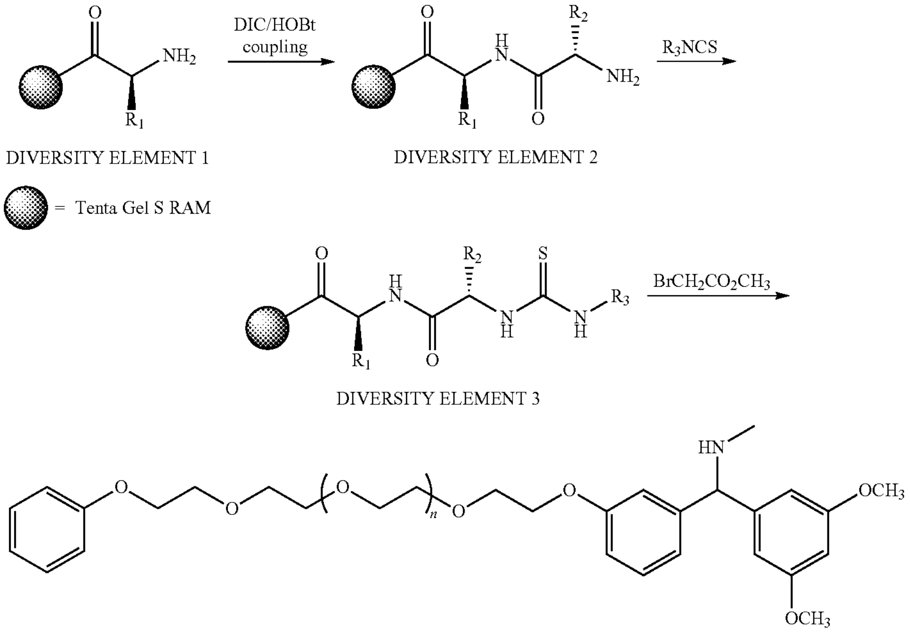
DIVERSITY ELEMENT 1
DIVERSITY ELEMENT 2
= Tenta Gel S RAM
DIVERSITY ELEMENT 3
DIVERSITY ELEMENT 4

-continued

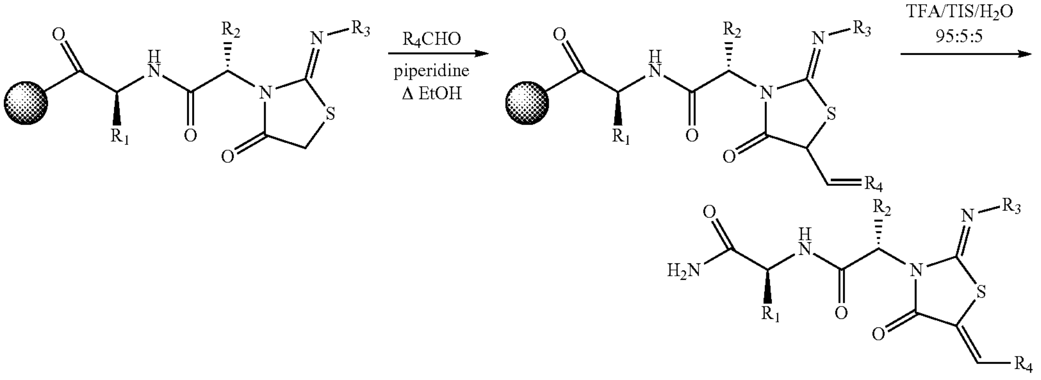

Properties of Representative T3S Inhibitors

All compounds were evaluated as T3S inhibitors in an engineered *Salmonella enterica* serovar *Typhimurium* strain as described herein. The results (Tables 3-5) demonstrate the preferred, tolerated, and deleterious functional groups for $R_1$, $R_2$, and $R_3$.

TABLE 3

A synthetic diversity set to evaluate modifications of $R_1$ and $R_3$. The percent inhibition of SipA secretion, as determined by Western blot, is shown in the right columns. In parentheses are the concentrations in μM at which that percent inhibition was achieved.

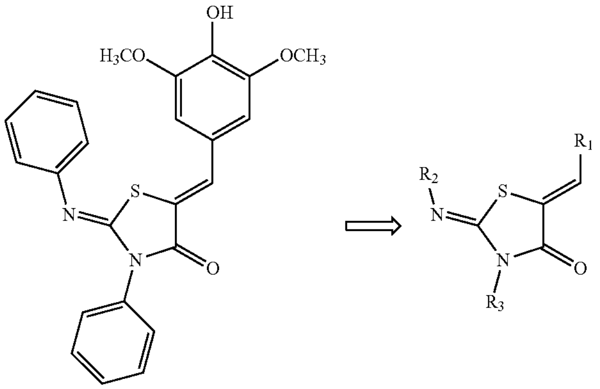

TTSS29
90% at 390 μM
35% at 39 μM

| | $R_1$ | $R_2$ | $R_3$ | % inhibition |
|---|---|---|---|---|
| 41 | 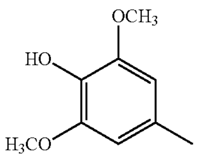 | Ph | 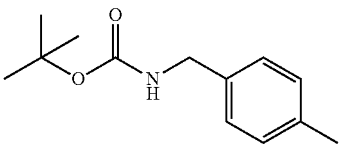 | 100 (330)[a] |
| 47 | | | 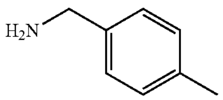 | 100 (330)<br>35 (33)<br>8 (3.3) |
| 45 | | | 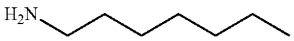 | 95 (330)<br>42 (33)<br>12 (3.3) |
| 57 | | | 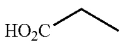 | 100 (330)<br>51 (3.3) |

TABLE 3-continued

A synthetic diversity set to evaluate modifications of $R_1$ and $R_3$. The percent inhibition of SipA secretion, as determined by Western blot, is shown in the right columns. In parentheses are the concentrations in μM at which that percent inhibition was achieved.

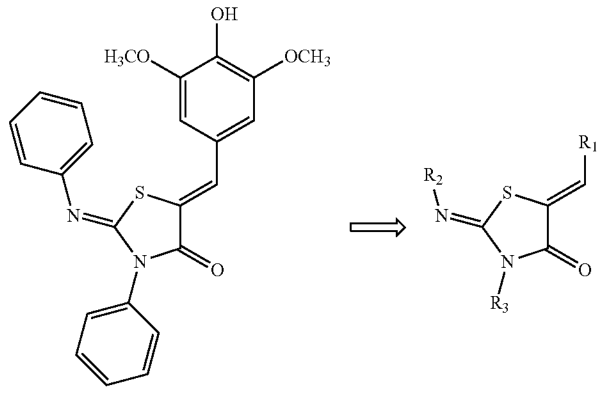

TTSS29
90% at 390 μM
35% at 39 μM

| | $R_1$ | $R_2$ | $R_3$ | % inhibition |
|---|---|---|---|---|
| 60 | | | 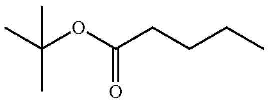 | 90 (330)<br>35 (3.3) |
| 61 | | | 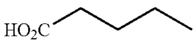 | 74 (330)<br>70 (3.3) |
| 64 | 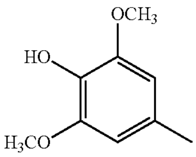 | Ph | 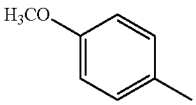 | 100 (330)<br>3 (33) |
| 66 | 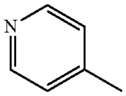 | | | 76 (330)<br>13 (33)<br>9 (3.3) |
| 67 | 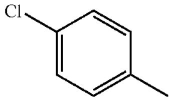 | | | 68 (330)<br>6 (33) |
| 75 | 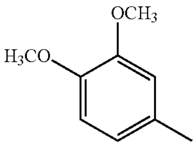 | | | 98 (330)<br>30 (33)<br>1 (3.3) |
| 73 | 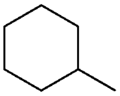 | | | 55 (330)<br>5 (33) |
| 81 | 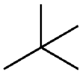 | | | 70 (330)<br>13 (33)<br>2 (3.3) |

[a]inactive at lower concentrations

TABLE 4
A synthetic diversity set to evaluate modifications of $R_1$ and $R_2$. The percent inhibition of SipA secretion, as determined by Western blot, is shown in the right columns.
In parentheses are the concentrations in μM at which that percent inhibition was achieved.
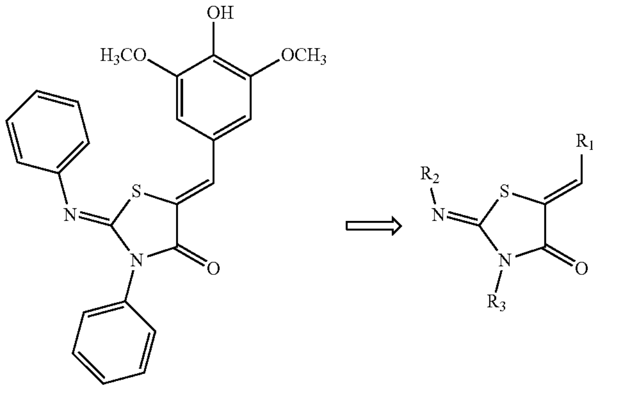
TTSS29
90% at 390 μM
35% at 39 μM
| | $R_1$ | $R_2$ | $R_3$ | % inhibition |
|---|---|---|---|---|
| 83 | 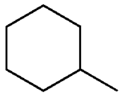 | Ph | Ph | 61 (330)[a] |
| 76 | 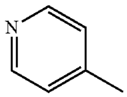 | | | 54 (330)[a] |
| 77 | 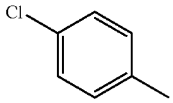 | | | 50 (330)[a] |
| 79 | 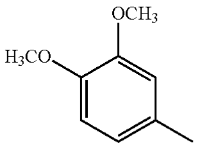 | | | 72 (330)[a] |
| 46 | | 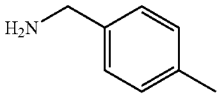 | | 85 (330)<br>16 (33)<br>7 (3.3) |
| 63 | | 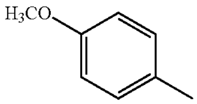 | | |
| 72 | 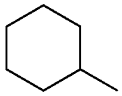 | 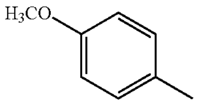 | Ph | 64 (330)<br>30 (33)<br>10 (3.3) |
| 65 | 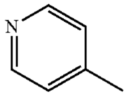 | | | 73 (330)<br>19 (33) |
| 67 | 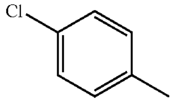 | | | 68 (330)<br>6 (33) |

TABLE 4-continued

A synthetic diversity set to evaluate modifications of $R_1$ and $R_2$. The percent inhibition of SipA secretion, as determined by Western blot, is shown in the right columns.
In parentheses are the concentrations in μM at which that percent inhibition was achieved.

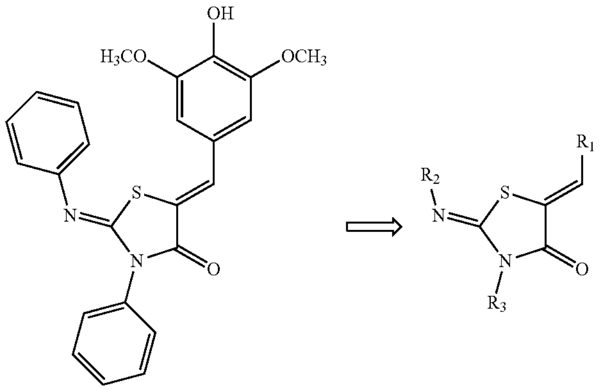

TTSS29
90% at 390 μM
35% at 39 μM

| | $R_1$ | $R_2$ | $R_3$ | % inhibition |
|---|---|---|---|---|
| 74 | 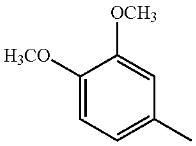 | | | 82 (330)[a] |
| 70 | 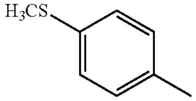 | | | 97 (330)<br>16 (33)<br>4 (3.3) |
| 80 | 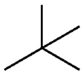 | | | 42 (330)<br>17 (33)<br>12 (3.3) |

[a]inactive at lower concentrations

TABLE 5

Dipeptides presented from N3. The percent inhibition of SipA secretion, as determined by Western blot, is shown in the right column. In parentheses are the concentrations in μM at which that percent inhibition was achieved.

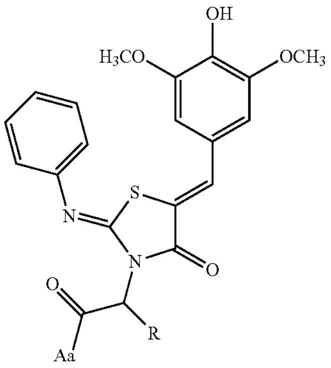

| | R (chirality) | Aa | % inhibition |
|---|---|---|---|
| 49 | $CH_3$ (S) | AlaCONH$_2$ | 94 (330)<br>26 (33) |

TABLE 5-continued

Dipeptides presented from N3. The percent inhibition of SipA secretion, as determined by Western blot, is shown in the right column. In parentheses are the concentrations in μM at which that percent inhibition was achieved.

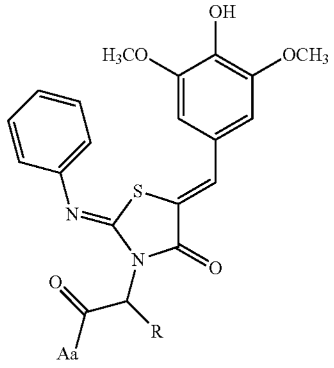

| | R (chirality) | Aa | % inhibition |
|---|---|---|---|
| 69 | $CH(CH_3)_2$ (isomer B) | $TyrCONH_2$ | 97 (330)<br>32 (33) |
| 50 | $CH_3$ (S) | $TyrCONH_2$ | 90 (330)[a] |
| 51 | $CH_3$ (R, S) | $TrpCONH_2$ | 100 (330)[a] |
| 52 | $CH_3$ (R) | $TrpCONH_2$ | 100 (330)[a] |
| 54 | $CH_3$ (S) | $OrnCONH_2$ | 94 (330)[a] |
| 84 | $CH_3$ (R) | $OrnCONH_2$ | 99 (330)<br>5 (3.3) |
| 56 | $CH_3$ (S) | $ArgCONH_2$ | 100 (330)<br>1 (33) |
| 85 | $CH_3$ (R) | $ArgCONH_2$ | 99 (330)<br>31 (33) |
| 91 | 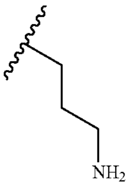 (S) | 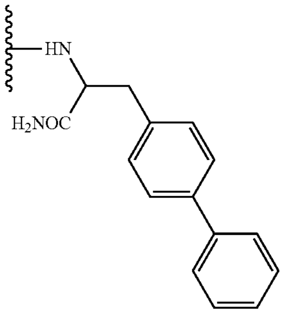 | 100 (330)<br>66 (33)<br>3 (3.3) |
| 86 | 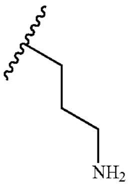 (S) | $AlaCONH_2$ | 100 (330)<br>46 (33)<br>19 (3.3) |
| 87 | 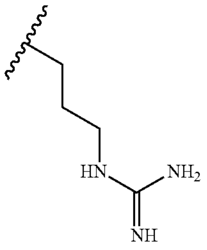 (S) | $AlaCONH_2$ | 100 (330)<br>38 (33)<br>0 (3.3) |

TABLE 5-continued
Dipeptides presented from N3. The percent inhibition of SipA secretion, as determined by Western blot, is shown in the right column. In parentheses are the concentrations in μM at which that percent inhibition was achieved.
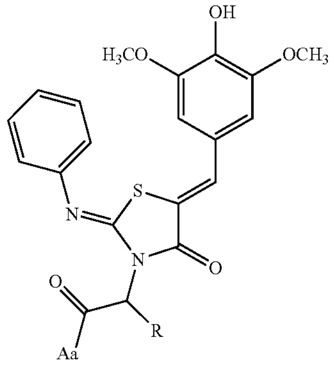
| | R (chirality) | | Aa | % inhibition |
|---|---|---|---|---|
| 88 | 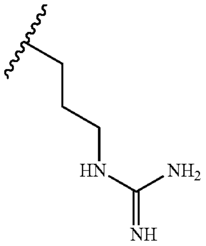 | (R, S) | 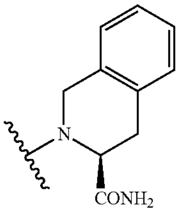 | 100 (330)<br>0 (33) |
| 94 | 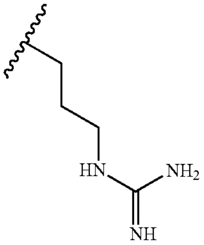 | (S) | 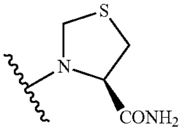 | 89 (330)<br>7 (33)<br>3 (3.3) |
| 89 | 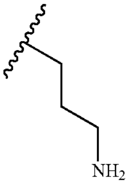 | (S) | 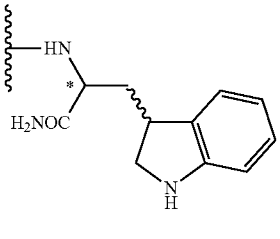 | 100 (330)<br>21 (33)<br>6 (3.3) |
| 90 | 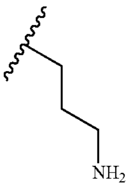 | (S) | 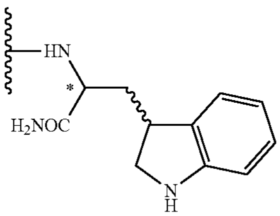 | 100 (330)<br>22 (33)<br>20 (3.3) |

TABLE 5-continued

Dipeptides presented from N3. The percent inhibition of SipA secretion, as determined by Western blot, is shown in the right column. In parentheses are the concentrations in μM at which that percent inhibition was achieved.

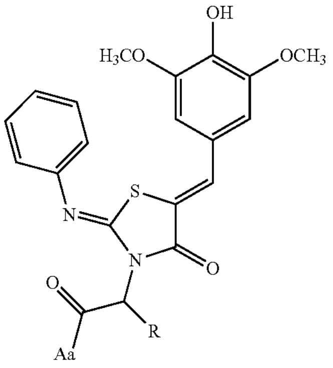

| | R (chirality) | | Aa | % inhibition |
|---|---|---|---|---|
| 98 | 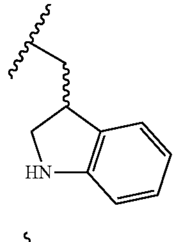 | (R, S) | $ArgCONH_2$ | 100 (330)<br>12 (33)<br>2 (3.3) |
| 95 | 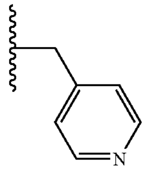 | (R, S) | $ArgCONH_2$ | 89 (330)<br>8 (33) |
| 96 | 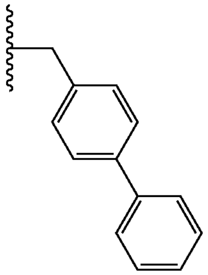 | (R, S) | $ArgCONH_2$ | 100 (330)<br>95 (33)<br>54 (3.3) |

[a]inactive at lower concentrations

Preparation of Representative T3S Inhibitors

The preparation of representative T3S inhibitors using synthetic Schemes I-III above are described below.

Scheme I

General Method A for generation of thioureas is illustrated for the preparation of t-butyl 6-(3-phenylthioureido)hexylcarbamate [004-1-1]. To a stirred solution of phenylisothiocyanate (244 mL, 2 mmol) in 50 mL $CH_2Cl_2$ was added 6-bocaminohexyl amine (448 mL, 2 mmol), and the solution stirred for 3 h until TLC (95:5 $CH_2Cl_2$:MeOH) showed the reaction to be complete. The solvent was removed in vacuo and the white solid collected and washed with hexane/diethyl ether to give 004-1-1 (593 mg, 1.70 mmol) that was used without further purification. $^1$H NMR ($CDCl_3$) d 1.50 (s, 9H); 1.34-1.58 (m, 8 h); 3.10 (dd, J=6.3 Hz, 6.3 Hz, 2H); 3.65 (dd, J=6.3 Hz, 6.3 Hz, 2H); 7.21-7.57 (m, 5H). MS m/z 374 $[M+Na]^+$, 274 $[M-Boc+Na]^+$.

t-Butyl 4-(3-phenylthioureido)benzylcarbamate [004-2-1] was prepared by General Method A on a 2 mmol scale, but allowed to react for 5 days to go to completion. Yield: 6.14 mg, 1.72 mmol. $^1$H NMR (300 MHz, $CDCl_3$, d) 1.47 (s, 9H), 4.32 (d, J=5.9 Hz, 2H); 4.91 (br, 1H), 7.28-7.86 (m, 9H). MS m/z 358 $[M+H]^+$, 380 $[M+Na]^+$324 $[M-tBu+H]^+$, 346 $[M-tBu+Na]^+$.

1-(4-methoxyphenyl)-3-phenylthiourea [SRJ3-83] was prepared by General Method A on a 4 mmol scale, using MeOH in place of $CH_2Cl_2$. Yield: 988 mg, 3.88 mmol. $^1$H NMR (300 MHz, $CDCl_3$, d) 3.82 (s, 3H); 6.95 (d, J=8.7 Hz, 2H); 7.44-7.21 (m, 6H). $^{13}$C NMR (500 MHz, $CDCl_3$, d) 58.52, 117.81, 128.73, 129.41, 130.79, 132.48, 142.87, 162.12, 184.81. MS m/z 259 $[M+H]^+$, 281 $[M+Na]^+$.

General Method B for generation of 2-iminothizolidinones is illustrated for the preparation of (Z)-t-Butyl 6-(4-oxo-2-phenylimino)thiazolidin-3-yl)hexylcarbamate [004-48-2]. To a stirred solution of 004-1-1 (400 mg, 1.14 mmol) in 40 mL $CH_2Cl_2$ were added successively DIEA (397 mL, 2.28 mmol) and methyl bromoacetate (108 mL, 1.14 mmol). The reaction mixture was stirred overnight at ambient temperature, concentrated in vacuo, and the residue purified via silica gel chromatography using a gradient from 1 to 20% MeOH in $CH_2Cl_2$ to give 004-48-2 (471 mg, 1.1 mmol) as a colorless oil. $^1$H NMR (300 MHz, $CDCl_3$, d) 1.51 (s, 9H), 1.38-1.77 (m, 8H), 3.11 (dd, J=6.3 Hz, 6.3 Hz, 2H) 3.81 (s, 2H), 3.86 (dd, J=7.2, 7.2 Hz, 2H), 4.53 (br., 1H), 6.95-7.39 (m, 5H). $^{13}$C NMR (500 MHz, $CDCl_3$, d) 26.38, 26.48, 27.11, 28.45, 29.93, 32.73, 40.47, 43/07, 78.98, 120.98, 124.59, 133.26, 148.26, 154.35, 155.9, 171.81. MS m/z 392 $[M+H]^+$, 414 $[M+Na]^+$, 336 $[M-tBu+H]^+$, 292 $[M-Boc+H]^+$.

(Z)-t-Butyl-4-(4-oxo-3-phenylthizolidin-2-ylideneamino) benzylcarbamate [004-49-1] and (Z)-t-Butyl-4-(4-oxo-2-phenylthizolidin-3-ylideneamino)benzylcarbamate [004-49-2] were prepared by General Method B from 004-2-1 on a 1.22 mmole scale to give, after silica gel chromatography using a gradient from 0 to 20% MeOH in $CH_2Cl_2$, 004-49-1 and 004-49-2 (484 mg, 1.2 mmol) as a mixture of regiomers. $^1$H NMR (300 MHz, $CDCl_3$, d) 1.48 (s, 9H), 3.99 (s, 2H), 4.29 (br d, J=5.1 Hz, 1H), 4.37 (br d, J=5.7, 1H), 4.90 (br, 1H), 6.89-7.57 (m, 9H). MS m/z 398.4 $[M+H]^+$, 420.2 $[M+Na]^+$, 342.4 $[M-tBu+H]^+$, 364.3 $[M-tBu+Na]^+$.

(Z)-3-(4-methoxyphenyl)-2-(phenylimino)thiazolidin-4-one [SRJ3-091] was prepared by General Method B on a 1.64 mmole scale to give, after silica gel chromatography using a gradient from 0 to 5% MeOH in $CH_2Cl_2$, SRJ3-091 (487 mg, 1.63 mmol) as a mixture of regiomers. $^1$H NMR (300 MHz, $CDCl_3$, d) 3.82 (s, 3H, minor isomer), 3.87 (s, 3H, major isomer), 4.0 (s, 2H, major isomer), 4.02 (s, 2H, minor isomer), 6.90-7.16 (m, 4H, major and minor isomers), 7.29-7.57 (m, 5H, major and minor isomers). $^{13}$C NMR (500 MHz, $CDCl_3$, d) 114.32, 114.72, 120.87, 121.94, 124.58, 127.19, 128.94, 129.03, 129.10, 129.34, 148.13, 159.71, 171.62. MS m/z 299 $[M+H]^+$, 321 $[M+Na]^+$.

(S)-N-((S)-1-Amino-3-(4-t-butyoxyphenyl)-1-oxopropan-2-yl)-2-((Z)-4-oxo-2-(phenylimino)thiazolidin-3-yl) propionamide [004-110-1] was prepared by General Method B from 004-104-1 on a 0.20 mmol scale, using THF in place of $CH_2Cl_2$, to give, after silica gel chromatography using a gradient from 1 to 10% MeOH in $CHCl_3$, 116 mg (0.20 mmol) product as a white foam. $^1$H NMR (300 MHz, $CDCl_3$, d) 1.33 (s, 9H) 1.55 (d, J=11.5 Hz, 3H), 3.02-3.26 (m, 2H), 3.73 (s, 2H), 4.71 (dd, J=7.3, 6.6 Hz, 1H), 5.15 (dd, J=7.2, 7.0 Hz, 1H), 5.0-5.5 (br, 1H), 6.05-6.07 (br, 2H), 6.91-7.36 (m, 9H). $^{13}$C NMR (500 MHz, $CDCl_3$, d) 17.51, 32.86, 36.64, 40.33, 56.74, 58.05, 82.54, 125.03, 128.18, 128, 44, 129.01, 132.01, 133.39, 133.51, 133.60, 133.79, 135.22, 51.26, 157.86, 172.47, 175.51, 177.25. MS m/z 483.3 $[M+H]^+$, 505.3 $[M+Na]^+$, 409.5 $[M-tBuOH+H]^+$.

t-Butyl-3-((S(-3-amino-3-oxo-2-((S)-2-((Z)-4-oxo-2-(phenylimino)thiazolidin-3-yl)propamido)proply)-1H-indole-1-carboxylate [004-117-1] was prepared by General Method B from 004-114-2 on a 0.13 mmol scale to give, after silica gel chromatography using a gradient from 1 to 10% MeOH in $CHCl_3$, 39.6 mg (0.07 mmol) product. $^1$H NMR (300 MHz, $CDCl_3$, d)1.57 (d, J=7.0 Hz, 3H), 2.66 (s, 9H), 3.17-3.43 (m, 2), 3.80 (d, J=5.1 Hz, 2H), 4.86, (dd, J=6.3, 7.6 Hz, 1H), 5.18 (q, J=7.0 Hz, 1H), 5.40 (br, 1H), 6.49 (br, 1H), 6.61 (d, J=8.5 Hz, 1H), 6.87 (d, J=12.5, 1H), 7.11-7.37 (m, 5H), 7.50 (s, 1H), 7.65 (d, J=12.5 Hz, 1H), 8.15 (d, J=12.6 Hz, 1H). $^{13}$C NMR (500 MHz, $CDCl_3$, d) 17.49, 30.50, 32.22, 36.66, 56.68, 87.95, 119.18, 119.46, 122.96, 124.97, 126.94, 128.52, 128.88, 129.04, 133.39, 134.28, 139.50, 151.20, 153.54, 157.85, 172.46, 175.41, 176.90. MS m/z 550.3 $[M+H]^+$, 572.3 $[M+Na]^+$, 494.3 $[M-tBu+H]^+$, 516.3 $[M-tBu+Na]^+$.

(S)-N-((S)-1-amino-1-oxopropan-2-yl)-2-((Z)-4-oxo-2-(phenylimino)thiazolidin-3-yl)propanamide [KCB3-006-2] was prepared by General Method B in THF on a 1.49 mmol scale, but allowed to react 3 days to go to completion. The crude solid was purified via silica gel chromatography using a gradient from 1 to 10% MeOH in $CH_2Cl_2$ to give KCB3-006-2 (300.0 mg, 0.90 mmol). $^1$H NMR (500 MHz, $CD_3OD$, d) 1.41 (d, J=7.19 Hz, 3H), 1.67 (d, J=7.01 Hz, 3H), 3.98 (s, 2H), 4.44 (q, J=7.05, 1H), 5.24 (q, J=6.96 Hz, 1H), 6.97 (d, J=7.62, 2H), 7.15 (t, J=7.34 Hz, 1H), 7.36 (t, J=7.66 Hz, 2H). $^{13}$C NMR ($CD_3OD$, d): 16.45, 20.53, 36.45, 53.45, 56.65, 125.48, 129.06, 133.66, 152.77, 159.34, 175.10, 177.36, 181.31. MS m/z 357.3 $[M+Na]^+$.

t-Butyl(S)-5-amino-5-oxo-4-((S)-2-((Z)-4-oxo-2-(phenylimino)thiazolidin-3-yl)propanamido)pentylcarbamate [KCB3-045] was prepared by General Method B in THF on a 1.77 mmol scale to give, after silica gel chromatography using a gradient from 0 to 10% MeOH in $CH_2Cl_2$, 603.8 mg (1.27 mmol) product. $^1$H NMR (300 MHz, $CD_3OD$, d) 1.44 (s, 9H), 1.49-1.78 (m, 3H), 1.66 (d, J=7.03 Hz, 3H), 1.82-2.01 (m, 1H), 2.50-3.10 (m, 2H), 3.97 (s, 2H), 4.33-4.49 (m, 1H), 5.25 (q, J=7.03 Hz, 1H), 6.98 (d, J=7.91 Hz, 2H), 7.14 (t, J=7.42 Hz, 1H), 7.35 (t, J=7.79 Hz, 2H). $^{13}$C NMR ($CDCl_3$, d): 17.71, 30.95, 32.45, 32.78, 36.76, 43.30, 56.53, 56.88, 83.50, 125.08, 128.98, 133.35, 151.30, 157.50, 160.76, 173.02, 175.55, 178.15. MS m/z 478.3 $[M+H]^+$, 500.3 $[M+Na]^+$.

(Z)-t-Butyl 2-(4-oxo-2-(phenylimino)thiazolidin-3-yl)acetate [KCB3-085] was prepared by General Method B in THF on a 1.80 mmol scale to give, after silica gel chromatography using a gradient from 0 to 10% MeOH in $CH_2Cl_2$, 344.4 mg (1.12 mmol) product. $^1$H NMR (300 MHz, $CDCl_3$, d) 1.51 (s, 9H), 3.91 (s, 2H), 4.50 (s, 2H), 6.89-7.02 (m, 2H), 7.07-7.21 (m, 1H), 7.29-7.41 (m, 2H). $^{13}$C NMR ($CDCl_3$, d): 32.23, 37.03, 48.71, 87.14, 125.73, 129.49, 134.03, 152.51, 157.55, 170.89, 176.37. MS m/z 329.2 $[M+Na]^+$.

(Z)-t-Butyl 4-(4-oxo-2-(phenylimino)thiazolidin-3-yl)butanoate [KCB3-101-3] was prepared by General Method B on a 1.53 mmol scale, and the crude material ($^1$H NMR (300 MHz, $CDCl_3$, d) 1.47 (s, 9H), 1.76-1.93 (m, 2H), 1.97-2.15 (m, 2H), 4.96-5.07 (m, 2H), 7.12-7.41 (m, 3H), 7.48 (t, J=7.73 Hz, 2H), 8.01 (br s, 1H), 8.55 (br s, 1H). MS m/z 295.2 $[M+H]^+$, 317.2 $[M+Na]^+$) reacted with methyl bromoacetate by General Method B in THF, but allowed to react 2 days to go to completion. The crude solid was purified via silica gel chromatography using a gradient from 10 to 50% ethyl acetate in hexane to give KCB3-101-3 (246.2 mg, 0.74 mmol). $^1$H NMR (300 MHz, $CDCl_3$, d) 1.47 (s, 9H), 1.64-1.96 (m, 4H), 3.75-3.83 (m, 2H), 4.02 (s, 2H), 7.33 (d, J=7.04 Hz, 2H), 7.39 (d, J=7.21 Hz, 1H), 7.48 (t, J=7.35 Hz, 2H). MS m/z 335.3 $[M+H]^+$, 357.3 $[M+Na]^+$.

t-Butyl(S)-5-amino-5-oxo-4-((R)-2-((Z)-4-oxo-2-(phenylimino)thiazolidin-3-yl)propanamido)pentylcarbamate [KCB3-173] was prepared by General Method B in THF on a 0.63 mmol scale, but allowed to react for 3 days to go to completion. The crude solid was purified via silica gel chromatography using a gradient from 0 to 10% MeOH in $CH_2Cl_2$ to give 277 mg (0.58 mmol) product. $^1$H NMR (300 MHz, $CDCl_3$, d) 1.44 (s, 9H), 1.50-1.71 (m, 3H), 1.73 (d, J=7.07 Hz, 3H), 1.92-2.15 (m, 1H), 3.08-3.41 (m, 2H), 3.89 (d, J=2.58 Hz, 2H), 4.56-4.80 (m, 1H), 5.19 (br s, 1H), 5.28 (q, J=7.07 Hz, 1H), 6.80 (br s, 1H), 6.95 (d, J=7.36 Hz, 2H), 7.17 (t, J=7.37 Hz, 1H), 7.36 (t, J=7.74 Hz, 2H), 7.50 (br s, 2H). MS m/z 478.4 $[M+H]^+$, 500.4 $[M+Na]^+$.

t-Butyl(S)-5-((S)-1-amino-1-oxopropan-2-ylamino)-5-oxo-4-((Z)-4-oxo-2-(phenylimino)thiazolidin-3-yl)pentylcarbamate [KCB3-188] was prepared by General Method B in THF on a 0.38 mmol scale, but allowed to react 4 days to go to completion. The crude solid was purified via silica gel chromatography using a gradient from 1 to 10% MeOH in $CHCl_3$ to give 109.7 mg (0.23 mmol) product. $^1$H NMR (300 MHz, $CD_3OD$, d) 1.39 (d, J=7.22 Hz, 3H), 1.44 (s, 9H), 1.48-1.61 (m, 2H), 2.10-2.28 (m, 1H), 2.28-2.47 (m, 1H), 3.13 (t, J=6.49 Hz, 2H), 4.00 (s, 2H), 4.46 (q, J=7.19 Hz, 1H), 5.10-5.70 (m, 1H), 6.95 (d, J=7.47 Hz, 2H), 7.13 (t, J=7.41 Hz, 1H), 7.34 (t, J=7.78 Hz, 2H). $^{13}$C NMR (500 MHz, $CD_3OD$, d) 20.62, 28.30, 29.62, 31.49, 36.26, 43.36, 53.09, 60.46, 82.59, 124.75, 128.37, 132.92, 151.87, 158.69, 161.19, 173.59, 176.85, 180.20. MS m/z 478.4 $[M+H]^+$, 500.3 $[M+Na]^+$.

(S)-5-amino-N-((S)-1-amino-3-(biphenyl-4-yl)-1-oxopropan-2-yl)-2-(Z)-4-oxo-2-(phenylimino)thiazolidin-3-yl) pentanamide [KCB3-229] was prepared by General Method B in THF on a 0.082 mmol scale, but allowed to react 5 days to go to completion. The crude solid was purified via silica gel chromatography using a gradient from 1 to 10% MeOH in $CH_2Cl_2$ to give 47.5 mg (0.075 mmol) product. $^1$H NMR (300 MHz, $CDCl_3$, d) 1.39-1.64 (m, 11H), 1.96-2.20 (m, 1H), 2.20-2.41 (m, 1H), 3.00-3.36 (m, 4H), 3.77 (d, J=6.14 Hz, 2H), 4.68-4.96 (m, 1H), 5.07-5.29 (m, 1H), 5.81 (br, 1H), 6.55 (br, 1H), 6.89 (d, J=7.89 Hz, 2H), 7.09-7.24 (m, 1H), 7.24-7.74 (m, 11H). $^{13}$C NMR ($CDCl_3$, d) 28.69, 30.77, 32.45, 36.50, 40.92, 43.76, 58.34, 61.15, 83.39, 125.01, 129.04, 130.96, 131.37, 132.07, 132.83, 133.37, 133.73, 139.78, 143.83, 144.48, 151.16, 158.28, 160.16, 172.50, 175.85, 177.27. MS m/z 630.4 $[M+H]^+$, 652.3 $[M+Na]^+$.

General Method C to introduce the 5-arylidene or 5-vinylidene substituent is illustrated by the synthesis of t-Butyl-6-((2Z,5Z)-5-(4-hydroxy-3,4-dimethoxybenzlidene)-4-oxo-2-(phenylimino)thiazolidin-3-yl)hexycarbamate [004-52-1]. A solution of 004-48-2 (471 mg, 1.14 mmol), syringaldehyde (208 mg, 1.14 mmol), and piperidine (152 mL, 1.54 mmol) in 9 mL of EtOH was refluxed for 19 h. The reaction mixture was cooled to ambient temperature and treated with hexane to precipitate the product, which was collected, washed with additional hexane, and dried to give 004-52-1 as an orange solid (548 mg, 0.95 mmol). $^1$H NMR (300 MHz, $CDCl_3$, d)1.42 (s, 9H), 1.46-1.54 (m, 4 H), 1.79 (m, 2 H), 1.98 (m, 2H), 3.03 (dd, J=6.5 Hz, 6.6 Hz, 2H), 3.86 (s, 6H), 3.96 (dd, J=4.2 Hz 4.2 Hz), 5.28 (br, 1H), 6.81 (s, 2H), 7.07 (d, J=7.5 Hz, 2H), 7.23 (t, J=7.4 Hz, 1H), 7.43 (J=7.9 Hz, 2H), 7.66 (s, 1H). $^{13}$C NMR (500 MHz, $CDCl_3$, d) 23.6, 24.4, 26.4, 26.5, 27.4, 28.5, 29.5, 42.9, 45.3, 55.7, 5681.4, 108.0, 121.0, 121.3, 124.5, 129.2, 129.2, 132.6, 148.5, 149.4, 151.0, 67.3. MS m/z 556.5 $[M+H]^+$, 578.4 $[M+Na]^+$, 500.5 $[M-tBu+H]^+$.

t-Butyl-4-((Z)-((Z)-5-(4-hydroxy-3,5-dimethoxybenzylidne)-4-oxo-3-phenylthiazolidin-2-ylidene)amino)benzylcarbamate [004-60-1] and t-butyl-4-((Z)-((Z)-5-(4-hydroxy-3,5-dimethoxybenzylidne)-4-oxo-2-phenylthiazolidin-3-ylidene)amino)benzylcarbamate [004-60-2] were prepared by General Method C from the 004-49-1 and 004-49-2 mixture on a 1.22 mmol scale. Preparative reverse phase HPLC using a gradient of 65 to 85% B in A over 15 min enabled the separation of the two pure compounds as well as an overlap band that was held in reserve for further purification. 004-60-1 (54.2 mg, 0.10 mmol) $^1$H NMR (300 MHz, $d_6$DMSO, d) 1.43 (s, 9H), 3.72 (s, 6 H), 4.15-4.23 m, 2H), 6.89 (s, 2H), 7.0-7.64 (m, 9H), 7.76 (s, 1H), 9.31 (br, 1H). MS m/z 562.5 $[M+H]^+$, 584.4 $[M+Na]^+$.

004-60-2 (48.5 mg, 0.09 mmol) $^1$H NMR (300 MHz, $d_6$DMSO, d) 1.41 (s, 9H), 3.77 (s, 6 H), 4.06-4.14 m, 2H), 6.90 (s, 2H), 6.95-7.59 (m, 9H), 7.75 (s, 1H), 9.32 (br, 1H). MS m/z 562.5 $[M+H]^+$, 584.3 $[M+Na]^+$.

(2Z,5Z)-5-(4-hydroxy-3,5-dimethoxybenzylidene)-2-(4-methoxyphenylimino)-3-phenylthiazolidin-4-one [SRJ3-093C7] was prepared by General Method C from the SRJ3-091 mixture on a 0.15 mmol scale. Preparative reverse phase HPLC using a gradient of 60-80% B in A over 23 min enabled the separation of one of the two compounds as well as an overlap band that was held in reserve for further purification. SRJ3-093C7 (22.9 mg, 0.05 mmol) $^1$H NMR (300 MHz, $CDCl_3$, d)2.31 (s, 3H), 2.33 (s, 6H), 4.03 (s, 2H), 4.18-4.30 (m, 4H), 4.39-4.44 (m, 5H), 4.64 (s, 1H). MS m/z 463.1322 $[M+H]^+$, 485.1142 $[M+Na]^+$.

(2Z,5Z)-5-(3,4-dimethoxybenzylidene)-3-(4-methoxyphenyl)-2-(phenylimino)thiazolidin-4-one [SRJ3-107A6] was prepared by General Method C from the SRJ3-091 mixture on a 0.067 mmol scale. Preparative reverse phase HPLC using a gradient of 60-80% B in A over 23 min enabled the separation of one of the two compounds as well as an overlap band (23.0 mg, 0.052 mmol) that was held in reserve for further purification. SRJ3-107A6 (3.72 mg, 0.0083 mmol). $^1$H NMR (300 MHz, $CDCl_3$, d)3.85 (s, 3H), 3.87 (s, 3H), 3.91 (s, 3H), 6.90-7.19 (m, 8H), 7.33-7.40 (m, 4H), 7.77 (s, 1H). $^{13}$C NMR (500 MHz, $CDCl_3$, d)55.48, 56.00, 111.32, 113.25, 114371, 121.20, 121.26, 123.40, 124.86, 126.69, 127.21, 129.16, 129.20, 129.25, 131.59, 148.23, 149.15, 150.66, 159.73, 166.83. MS m/z 447.1373 $[M+H]^+$, 469.1192 $[M+Na]^+$.

(2Z,5Z)-3-(4-methoxyphenyl)-5-(4-(methylthio)benzylidene)-2-(phenylimino)thiazolidin-4-one [SRJ3-103A7] was prepared by General Method C from the SRJ3-091 mixture on a 0.067 mmol scale. Preparative reverse phase HPLC using a gradient of 60-80% B in A over 23 min enabled the separation of one of the two compounds as well as an overlap band (3.47 mg, 0.0080 mmol) that was held in reserve for further purification. SRJ3-103 A7 (6.24 mg, 0.014 mmol) $^1$H NMR (300 MHz, $CDCl_3$, d)2.50 (s, 3H), 3.85 (s, 3H), 6.91-7.23 (m, 7H), 7.34-7.41 (m, 6H), 7.77 (s, 1H). $^{13}$C NMR (500 MHz, $CDCl_3$, d)14.98, 55.47, 114.68, 121.12, 124.80, 125.88, 129.11, 129.24, 130.36, 130.89. MS m/z 433.1039 $[M+H]^+$, 455.0858 $[M+Na]^+$.

(2Z,5Z)-5-(cyclohexylmethylene)-3-(4-methoxyphenyl)-2-(phenylimino)thiazolidin-4-one [SRJ3-105B6] was prepared by General Method C from the SRJ3-091 mixture on a 0.067 mmol scale. Preparative reverse phase HPLC using a gradient of 80-95% B in A over 25 min enabled the separation of one of the two compounds as well as an overlap band (16.88 mg, 0.043 mmol) that was held in reserve for further purification. SRJ3-105B6 (4.39 mg, 0.011 mmol). $^1$H NMR (300 MHz, $CDCl_3$, d)1.24 (s, 6H), 1.65 (s, 4H), 2.08 (s, 1H), 3.84 (s, 3H), 6.84 (d, J=9.6 Hz, 1H), 6.93 (d, J=7.45 Hz, 2H), 7.03 (d, J=8.7 Hz, 2H), 7.14 (t, J=7.3 Hz, 1H), 7.32-7.34 (m, 4H). $^{13}$C NMR (500 MHz, $CDCl_3$, d) 25.25, 25.56, 31.15, 41.06, 55.14, 114.64, 121.08, 122.74, 124.69, 127.24, 129.06, 129.14, 140.50, 148.62, 159.63. MS m/z $[M+H]^+$ 393.1631, 415.1451 $[M+Na]^+$.

(2Z,5Z)-3-(4-methoxyphenyl)-2-(phenylimino)-5-(pyridin-4-ylmethylene)thiazolidin-4-one [SRJ3-095 B5] was prepared by General Method C from the SRJ3-091 mixture on a 0.067 mmol scale. Preparative reverse phase HPLC using a gradient of 60-80% B in A over 25 min enabled the separation of one of the two compounds as well as an overlap band (9.3 mg, 0.024 mmol, 36%) that was held in reserve for further purification. SRJ3-095 B5 (3.17 mg, 0.0082 mmol). $^1$H NMR (300 MHz, $CDCl_3$, d)3.86 (s, 3H), 6.96 (d, J=7.4 Hz, 2H), 7.07 (d, J=8.9 Hz, 2H), 7.19-7.26 (m, 2H), 7.36-7.41 (m, 4H), 7.53-7.55 (m, 2H), 7.74 (s, 1H), 8.75 (s, 2H). $^{13}$C NMR (500 MHz, $CDCl_3$, d)55.53, 114.81, 120.86, 124.41, 125.46, 125.99, 128.93, 129.45, 147.06, 147.09. MS m/z 388.1108 $[M+H]^+$, 426.0669 $[M+K]^+$.

(2Z,5Z)-5-(4-chlorobenzylidene)-3-(4-methoxyphenyl)-2-(phenylimino)thiazolidin-4-one [SRJ3-097 A15] was prepared by General Method C from the SRJ3-091 mixture on a 0.067 mmol scale. Preparative reverse phase HPLC using a gradient of 60-80% B in A over 25 min enabled the purification of a mixture of the two regioisomers, SRJ3-097 A15 (17.08 mg, 0.041 mmol). $^1$H NMR (300 MHz, $CDCl_3$, d)3.83 (s, 3H, minor), 3.85 (s, 3H, major), 6.92 (s, 1H, major and minor), 6.96-7.07 (m, 3H, major and minor), 7.16-7.26 (m, 1H, major and minor), 7.35-7.58 (m, 7H, major and minor), 7.77 (s, 1H, major and minor). $^{13}$C NMR (500 MHz, $CDCl_3$, d)29.73, 55.46, 55.50, 114.53, 114.66, 114.73, 121.09, 122.18, 124.99, 128.00, 128.04, 128.76, 128.84, 128.86, 128.88, 128.90, 128.91, 128.95, 129.01, 129.11, 129.32, 129.36, 129.48, 129.52, 129.54, 129.57, 129.81, 129.89, 129.94, 131.14, 132.19, 135.85, 148.19, 150.96, 159.79, 166.48. MS m/z 421.0775 $[M+H]^+$, 443.0591 $[M+Na]^+$.

(2Z,5Z)-5-(2,2-dimethylpropylidene)-3-(4-methoxyphenyl)-2-(phenylimino)thiazolidin-4-one [SRJ3-117 A3] was prepared by General Method C from the SRJ3-091 mixture on a 0.067 mmol scale. Preparative reverse phase HPLC using a gradient of 60-95% B in A over 25 min enabled the separation of one of the two compounds as well as an overlap band (2.68 mg, 0.0073 mmol) that was held in reserve for further purification. SRJ3-117 A3 (4.00 mg, 0.011 mmol) $^1$H NMR (300 MHz, $CDCl_3$, d)1.19 (s, 9H), 3.84 (s, 3H), 6.93 (d, J=7.4 Hz, 1H), 7.02-7.03 (m, 2H), 7.13 (t, J=7.4 Hz, 2H), 7.34-7.31 (m, 5H). $^{13}$C NMR (500 MHz, $CDCl_3$, d)29.15, 33.90, 55.46, 114.66, 120.34, 121.11, 124.62, 127.32, 128.05, 129.09, 129.14, 145.39, 148.34, 159.63, 166.73. MS m/z 367.1475 $[M+H]^+$, 389.1294 $[M+Na]^+$.

(2Z,5Z)-5-(cyclohexylmethylene)-3-phenyl-2-(phenylimino)thiazolidin-4-one [SRJ3-121] was prepared by General Method C from TK4-133 on a, 0.089 mmol scale. Silica gel chromatography using a gradient of 0-10% ethyl acetate in hexane yielded SRJ3-121 (9.64 mg, 0.027 mmol) $^1$H NMR (300 MHz, $CDCl_3$, d)1.26 (br, 6H), 1.74-1.57 (m, 4H), 2.09 (br, 1H), 6.85 (d, J=9.6 Hz, 1H), 6.94 (d, J=7.4 Hz, 3H), 7.13-7.16 (m, 2H), 7.33-7.53 (m, 5H). $^{13}$C NMR (500 MHz, $CDCl_3$, d)25.26, 25.33, 25.59, 29.70, 31.16, 41.10, 121.04, 122.75, 124.73, 128.00, 128.85, 129.17, 129.26, 134.71, 140.59, 148.54, 151.52, 165.53. MS m/z 363.1526 $[M+H]^+$, 385.1345 $[M+Na]^+$.

(2Z,5Z)-3-phenyl-2-(phenylimino)-5-(pyridin-4-ylmethylene)thiazolidin-4-one [SRJ3-109] was prepared by General Method C from TK4-133 on a, 0.075 mmol scale. Silica gel chromatography using a gradient of 0-50% ethyl acetate in hexane yielded SRJ3-109 (5.63 mg, 0.016 mmol) $^1$H NMR (300 MHz, $CDCl_3$)7.00 (d, J=7.5 Hz, 2H), 7.23 (t, J=7.4 Hz, 2H), 7.36-7.43 (m, 5H), 7.50-7.61 (m, 5H), 7.75 (s, 2H), 8.72 (br, 2H). $^{13}$C NMR (500 MHz, $CDCl_3$) 29.71, 29.80, 120.91, 123.34, 123.38, 125.24, 126.71, 127.91, 127.96. 129.19, 129.38, 129.41, 134.37. 140.79, 147.79, 150.54. MS m/z 358.1009 $[M+H]^+$, 380.0828 $[M+Na]^+$.

(2Z,5Z)-5-(4-chlorobenzylidene)-3-phenyl-2-(phenylimino)thiazolidin-4-one [SRJ3-111] was prepared by General Method C from TK4-133 on a 0.075 mmol scale. Silica gel chromatography using a gradient of 0-35% ethyl acetate in hexane yielded SRJ3-111 (1.07 mg, 0.0027 mmol) $^1$H NMR (300 MHz, $CDCl_3$) 6.97 (d, J=7.3 Hz, 2H), 7.18 (t, J=7.4 Hz, 1H), 7.35-7.57 (m, 10H), 7.77 (s, 2H). $^{13}$C NMR (500 MHz, $CDCl_3$) 121.03, 125.00, 128.01, 129.03, 129.32, 129.36, 130.00, 131.13. MS m/z 391.0666 $[M+H]^+$, 413.0486 $[M+Na]^+$.

(2Z,5Z)-5-(3,4-dimethoxybenzylidene)-3-phenyl-2-(phenylimino)thiazolidin-4-one [SRJ3-115] was prepared by General Method C from TK4-133 on a 0.075 mmol scale. Silica gel chromatography using a gradient of 0-30% ethyl acetate in hexane yielded SRJ3-115 (11.63 mg, 0.028 mmol) $^1$H NMR (300 MHz, $CDCl_3$) (s, 3H), 3.91 (s, 3H), 6.91 (d, J=8.4 Hz, 1H), 6.98-6.99 (m, 3H), 7.10-7.12 (m, 2H), 7.35 (t, J=7.8 Hz, 2H), 7.44-7.56 (m, 5H), 7.77 (s, 1H). $^{13}$C NMR (500 MHz, $CDCl_3$) 33.76, 60.05, 60.13, 115.37, 117.30, 122.91, 125.17, 127.45, 128.86, 130.74, 132.06, 132.13, 132.94, 133.02, 133.15, 133.26, 133.35, 135.57, 138.84, 152.34, 153.20, 154.70, 155.14, 170.63. MS m/z 417.1267 $[M+H]^+$, 439.1087 $[M+Na]^+$.

(2Z,5Z)-5-(4-(methylthio)benzylidene)-3-phenyl-2-(phenylimino)thiazolidin-4-one [SRJ3-113] was prepared by General Method C from TK4-133 on a 0.075 mmol scale. Silica gel chromatography using a gradient of 0-20% ethyl acetate in hexane yielded SRJ3-113 (14.51 mg, 0.036 mmol). $^1$H NMR (300 MHz, $CDCl_3$) 2.53 (s, 3H), 7.02, (d, J=7.5 Hz, 1H), 7.21 (t, J=7.4 Hz, 2H), 7.28 (d, J=8.33 Hz, 2H), 7.39-7.60 (m, 8H), 7.81 (s, 1H). $^{13}$C NMR (500 MHz, $CDCl_3$) 14.95, 119.898, 121.07, 124.83, 125.85, 128.03, 128.89, 129.25, 129.28, 129.41, 129.97, 130.35, 130.95, 134.71, 142.00, 148.26, 150.92, 166.50. MS m/z 403.0933 $[M+H]^+$, 425.0753 $[M+Na]^+$.

(2Z,5Z)-5-(2,2-dimethylpropylidene)-3-phenyl-2-(phenylimino)thiazolidin-4-one [SRJ3-119] was prepared by General Method C from TK4-133 on a 0.075 mmol scale. Silica gel chromatography using a gradient of 0-20% ethyl acetate in hexane yielded SRJ3-119 (4.74 mg, 0.014 mmol). $^1$H NMR (300 MHz, $CDCl_3$) 1.22 (s, 9H), 6.96-6.98 (m, 2H), 7.07-7.17 (m, 4H), 7.29-7.56 (m, 5H). $^{13}$C NMR (500 MHz, $CDCl_3$) 28.92, 29.01, 29.67, 29.70, 120.98, 121.07, 124.64, 124.76, 127.93, 128.04, 128.69, 128.80, 128.84, 129.08, 129.17, 129.20, 129.27, 129.42, 145.46, 157.60. MS m/z 337.1369 $[M+H]^+$, 359.1189 $[M+Na]^+$.

(S)-N-((S)-1-amino-3-(4-tert-butoxyphenyl)-1-oxopropan-2-yl)-2-((2Z,5Z)-5-(4-hydroxy-3,5-dimethoxybenzylidene)-4-oxo-2-(phenylimino)thiazolidin-3-yl)propanamide [004-112-1] was prepared by General Method C from 004-110-1 on a 0.20 mmol scale to give 34 mg (0.05 mmol) product as a bright orange solid that was carried on to the deprotection step without further purification. $^1$H NMR (300 MHz, $CDCl_3$, d)1.60 (d, J=7.0 Hz, 3 H), 1.35 (s, 9H), 2.89 (br, 2H), 3.07 (dd, J=6.6, 6.7 Hz, 1H), 3.33 (dd, J=6.6, 6.7 Hz, 1H), 3.30 (br, 1H), 3.88 (s, 6H), 4.75 (q, J=7.6, 6.6 Hz, 1H), 5.20 (br, 1H), 5.34 (dd, J=7.0, 7.1 Hz, 1H), 6.36 (d, J=8.4 Hz, 2H), 6.68 (s, 2H), 6.94-7.4 (m, 8H), 7.66 (s, 1H). MS m/z 647.4 $[M+H]^+$, 669.4 $[M+Na]^+$.

t-Butyl-3-((S)-3-amino-2-((S)-2-((2Z,5Z)-5-(4-hydroxy-3,5-dimethoxy-benzylidene)-4-oxo-2-(phenylimino)thiazolidin-3-yl)propanamido)-3-oxopropyl)-1H-indole-1-carboxylate [004-119-2] was prepared by General Method C from 004-117-1 on a 0.07 mmol scale to give, after purification on silica gel using a gradient from 0 to 20% MeOH in $CH_2Cl_2$, 12 mg (0.02 mmol) product as a bright orange solid. $^1$H NMR (300 MHz, $CDCl_3$) 1.57-1.72 (s over m, 12H), 3.24-3.45 (m, 2H), 3.73 (s, 6H), 4.58-4.68 (m, 1H), 5.06-6.10 (m, 1H), 5.80-6.00 (br, 1H), 6.40-7.43 (m, 13H). MS m/z 714.4 $[M+H]^+$, 736.4 $[M+Na]^+$.

(S)-N-((S)-1-amino-1-oxopropan-2-yl)-2-((2Z,5Z)-5-(4-hydroxy-3,5-dimethoxybenzylidene)-4-oxo-2-(phenylimino)thiazolidin-3-yl)propanamide [TZN49]. TZN49 was prepared by General Method C from KCB3-006-2 on a 0.86 mmol scale. Preparative reverse phase HPLC on 20 mg crude material using a gradient of 10 to 60% B in A over 30 min gave TZN49 (3.5 mg, 0.007 mmol). $^1$H NMR (500 MHz, $CD_3OD$, d) 1.42, (d, J=7.21 Hz, 3H), 1.73 (d, J=7.00 Hz, 3H), 3.84 (s, 6H), 4.47 (q, J=7.16 Hz, 1H), 5.42 (q, J=7.02 Hz, 1H), 6.81 (s, 2H), 7.06 (d, J=7.57 Hz, 2H), 7.22 (t, J=7.43 Hz, 1H), 7.42 (t, J=7.73 Hz, 2H), 7.71 (s, 1H). $^{13}$C NMR ($CD_3OD$, d): 16.66, 20.44, 53.21, 56.53, 59.44, 111.62, 121.77, 124.90, 128.46, 128.74, 133.03, 135.80, 142.28, 151.87, 152.20, 153.65, 170.45, 174.00, 180.30. MS m/z 499.4 $[M+H]^+$, 521.3 $[M+Na]^+$ t-Butyl-(S)-5-amino-4-((S)-2-((2Z,5Z)-5-(4-hydroxy-3,5-dimethoxybenzylidene)-4-oxo-2-(phenylimino)thiazolidin-3-yl)propanamido)-5-oxopentylcarbamate [KCB4-021] was prepared by General Method C from KCB4-017 on a 0.44 mmol scale. The crude solid was purified via silica gel chromatography using a gradient from 0 to 10% MeOH in $CH_2Cl_2$ to give 224 mg (0.35 mmol) product. $^1$H NMR (300 MHz, $CD_3OD$, d) 1.41 (s, 9H), 1.47-1.68 (m, 3H), 1.72 (d, J=7.05 Hz, 3H), 1.81-2.02 (m, 1H), 3.03 (t, J=6.53 Hz, 2H), 3.83 (s, 6H), 4.35-4.45 (m, 1H), 5.43 (q, J=7.01 Hz, 1H), 6.81 (s, 2H), 7.07 (d, J=7.39 Hz, 2H), 7.20 (t, J=7.44 Hz, 1H), 7.41 (t, J=7.83 Hz, 2H), 7.71 (s, 1H). $^{13}$C NMR ($CDCl_3$, d) 17.97, 30.82, 32.43, 32.93, 43.32, 56.49, 56.97, 60.44, 83.41, 111.36, 122.30, 125.18, 125.26, 129.05, 129.17, 133.37, 136.29, 141.20, 151.39, 153.30, 160.68, 170.35, 173.15, 178.17. MS m/z 642.4 $[M+H]^+$, 664.5 $[M+Na]^+$.

t-Butyl-2-((2Z,5Z)-5-(4-hydroxy-3,5-dimethoxybenzylidene)-4-oxo-2-(phenylimino)thiazolidin-3-yl)acetate [KCB3-093] was prepared by General Method C from KCB3-085 on a 1.12 mmol scale to give, after silica gel chromatography using a gradient from 10 to 50% ethyl acetate in hexane, 329.8 mg (0.70 mmol) product. $^1$H NMR (300 MHz, $CDCl_3$, d) 1.52 (s, 9H), 3.89 (s, 6H), 4.64 (s, 2H), 6.71 (s, 2H), 7.03 (d, J=7.89 Hz, 2H), 7.15-7.25 (m, 1H), 7.39 (t, J=7.79 Hz, 2H), 7.72 (s, 1H). $^{13}$C NMR ($CDCl_3$, d) 32.06, 48.52, 60.48, 86.62, 111.25, 122.87, 125.20, 128.95, 129.26, 133.31, 136.01, 140.94, 151.29, 151.65, 153.62, 170.01, 170.40. MS m/z 471.4 $[M+H]^+$, 493.4 $[M+Na]^+$.

t-Butyl-4-((2Z,5Z)-5-(4-hydroxy-3,5-dimethoxybenzylidene)-4-oxo-2-(phenylimino)thiazolidin-3-yl)butanoate [TZN60] was prepared by General Method C from KCB3-101-3 on a 0.74 mmol scale to give, after silica gel chromatography using a gradient from 10 to 75% ethyl acetate in hexane, 190 mg (0.48 mmol) product. $^1$H NMR (300 MHz, $CDCl_3$, d) 1.48 (s, 9H), 1.73-2.01 (m, 4H), 3.81-3.93 (m, 2H), 3.99 (s, 6H), 6.84 (s, 2H), 7.36-7.62 (m, 5H), 7.75 (s, 1H). $^{13}$C NMR ($CDCl_3$, d) 14.48, 30.86, 32.08, 60.50, 71.33, 85.47, 111.28, 122.53, 129.48, 132.04, 132.45, 132.93, 135.21, 139.09, 140.83, 151.35, 154.28, 170.41, 174.38. MS m/z 499.5 $[M+H]^+$, 521.4 $[M+Na]^+$.

t-Butyl-(S)-5-((S)-1-amino-1-oxopropan-2-ylamino)-4-((2Z,5Z)-5-(4-hydroxy-3,5-dimethoxybenzylidene)-4-oxo-2-(phenylimino)thiazolidin-3-yl)-5-oxopentylcarbamate [KCB3-197] was prepared by General Method C from KCB3-188 on a 0.23 mmol scale to give, after silica gel chromatography using a gradient from 1 to 10% MeOH in $CHCl_3$, 117 mg (0.18 mmol) product. $^1$H NMR (500 MHz, $CDCl_3$, d) 1.44 (s, 12H), 1.50-1.74 (m, 2H), 2.11-2.31 (m, 1H), 2.38-2.57 (m, 1H), 3.10-3.40 (m, 2H), 3.83 (s, 6H), 4.54-4.73 (m, 1H), 5.26-5.45 (m, 1H), 5.75 (br s, 1H), 6.61 (s, 2H), 6.80 (br s, 1H), 7.01 (d, J=7.34 Hz, 2H), 7.14-7.29 (m, 1H), 7.37 (t, J=7.46 Hz, 2H), 7.60 (s, 1H). $^{13}$C NMR (500 MHz, $CDCl_3$, d) 21.70, 29.16, 30.86, 32.43, 43.81, 53.00, 60.42, 61.21, 83.35, 111.41, 121.83, 125.17, 128.91, 129.22, 133.39, 136.66, 141.32, 151.39, 153.83, 160.24, 170.80, 172.51, 178.70. MS m/z 642.4 $[M+H]^+$.

t-Butyl-(S)-5-((S)-1-amino-3-(biphenyl-4-yl)-1-oxopropan-2-ylamino)-4-((2Z,5Z)-5-(4-hydroxy-3,5-dimethoxybenzylidene)-4-oxo-2-(phenylimino)thiazolidin-3-yl)-5-oxopentylcarbamate [KCB4-008] was prepared by General Method C from KCB3-229 on a 0.075 mmol scale. The crude solid was purified via silica gel chromatography using a gradient from 0 to 5% MeOH in $CH_2Cl_2$ to give 41 mg (0.052 mmol). $^1$H NMR (500 MHz, $CD_3OD$, d) 1.41 (s, 9H), 1.46-1.66 (m, 2H), 2.12-2.29 (m, 1H), 2.34-2.52 (m, 1H), 3.00-3.21 (m, 3H), 3.21-3.32 (m, 1H), 3.71 (s, 6H), 4.62-4.75 (m, 1H), 5.24-5.40 (m, 1H), 6.64 (s, 2H), 6.90 (d, J=7.52 Hz, 2H), 7.13 (t, J=7.37 Hz, 1H), 7.21-7.50 (m, 11H), 7.62 (s, 1H). $^{13}$C NMR ($CD_3OD$, d) 28.35, 30.27, 31.45, 40.66, 43.43, 58.66, 59.39, 60.76, 82.57, 111.62, 121.03, 125.00, 128.27, 128.73, 130.35, 130.74, 130.79, 132.32, 132.93, 133.33, 136.34, 140.12, 142.35, 143.37, 144.42, 151.55, 152.12, 153.72, 161.14, 170.61, 173.42, 178.71. MS m/z 794.5 $[M+H]^+$.

General Method D for deprotection of the amine is illustrated by the preparation of (2Z,5Z)-3-(6-aminohexyl)-5-(4-hydroxy-3,5-dimethoxybenzylidene)-2-(phenylimino)-thiazolidin-4-one [TZN45]. Ice cold TFA (3 mL, 40 mmol) was added to neat 004-52-1 (528 mg, 0.95 mmol) cooled in an ice bath. The reaction was complete by HPLC in 15 min, and the reaction mixture was concentrated in vacuo to a sticky brown oil. Trituration with diethyl ether gave a solid residue that was purified by two successive silica gel chromatographies, the first using a gradient of 0 to 10% MeOH in $CHCl_3$ and the second 1 to 50% MeOH in $CHCl_3$, to give 004-63-1b (456 mg, 0.8 mmol). $^1$H NMR (300 MHz, $CDCl_3$) 1.42-1.45 (m, 4H), 1.64-1.66 (m, 2H), 1.77-1.79 (m, 2H), 2.65 (br, 2H), 2.89 (t, J=7.5 Hz, 2H), 3.84 (s, 6H), 3.97 (t, J=7.5 Hz, 2H), 6.71 (s, 2H), 6.99 (d, J=8.4, 2H), 7.14-7.19 (m, 1H), 7.28-7.38 (m, 2H), 7.63 (s, 1H). $^{13}$C NMR (500 MHz, =$d_7$ DMF d) 30.2, 30.5, 31.3, 43.6, 47.0, 53.0, 60.3, 112.5, 120.6, 122.1, 123.0, 125.5, 129.0, 133.5, 133.6, 135.5, 152.6, 152.8, 154.4, 162.9, 163.1, 163.4, 166.1, 166.4, 166.6, 170.5. MS m/z 456.4 $[M+H]^+$. HRMS calculated for $C_{24}H_{30}N_3O_4S$ 456.1957, found 456.1946.

(2Z,5Z)-2-(4-(aminomethyl)phenylimino)-5-(4-hydroxy-3,5-dimethoxybenzyldene)-3-phenylthiazolidin-4-one [TZN46] was obtained from 004-36-1 (4.0 mg, 0.007 mmol) by General Method D, and purified on reverse phase HPLC (65 to 85% B in A over 12 min) to give TZN46 (3.0 mg, 0.004 mmol) as the TFA salt. $^1$H NMR (500 MHz, $CD_3CN$, d) 3.83 (s, 6H), 4.25 (s, 2H), 6.85 (s, 2H), 7.02 (d J=8.5 Hz, 2H), 7.22 (t J=8.2 Hz, 1H), 7.t2 (t J=8.5 Hz, 2H), 7.60 (d J=8.4 Hz, 2H), 7.67 (d J=8.4 Hz, 2H), 7.74 (s, 1H). MS m/z 462.3 $[M+H]^+$. HRMS calculated for $C_{25}H_{23}N_3O_4S$ 462.1488 found 462.1491.

(2Z,5Z)-3-(4-(aminomethyl)phenylimino)-5-(4-hydroxy-3,5-dimethoxybenzyldene)-2-phenylthiazolidin-4-one [TZN47] was obtained from 004-36-2 (6.9 mg, 0.01 mmol) by General Method D, and purified on reverse phase HPLC (65 to 85% B in A over 12 min) to give TZN46 (5.5 mg, 0.009 mmol) as the TFA salt. $^1$H NMR (500 MHz, $CD_3CN$, d) 3.84 (s, 6H), 4.14 (s, 2H), 6.86 (s, 2H), 7.05 (d J=8.3 Hz, 2H), 7.46-4.62 (m, 7H) 7.75 (s, 1H). MS m/z 462.4 $[M+H]^+$. HRMS calculated for $C_{25}H_{23}N_3O_4S$ 462.1488 found 462.1486.

(S)-N-((S)-1-amino-3-(4-hydroxyphenyl)-1-oxopropan-2-yl)-2-((2Z,5Z)-5-(4-hydroxy-3,5-dimethoxybenzylidene)-4-oxo-2-(phenylimino)thiazolidin-3-yl)propanamide [TZN50] was obtained from 004-112-1 (34 mg, 0.05 mmol) by General Method D and purified on reverse phase HPLC (20 to 95% B in A over 12 min) to give the product (22 mg, 0.036 mmol) as the TFA salt. $^1$H NMR (500 MHz, $(CD_3)_2CO$, d) 1.70(d, J=7.1 Hz, 3H), 2.07 (br, 2H), 2.98 (dd, J=7.7, 7.7

Hz, 1H), 3.09 (dd, J=6.5, 6.5 Hz, 1H), 3.30 (br, 1H), 3.88 (s, 6H), 4.56 (br, 1H), 4.57 (q, J=7.6, 5.8 Hz, 1H), 5.32 (dd, J=7.0, 7.1 Hz, 1H), 6.50 (br, 1H), 6.73 (d, J=8.4 Hz, 2H), 6.89 (s, 2H), 7.02 (d, J=8.2 Hz, 2H), 7.10 (d, J=8.4 Hz, 2H), 7.20 (t, J=7.4 Hz, 1H), 7.41 (m, 2H), 7.67 (s, 1H). MS m/z 591.3 $[M+H]^+$, 411.3 $[M-Tyr+H]^+$. HRMS calculated for $C_{30}H_{31}N_4O_7S$ 591.1913 found 591.1905 $[M+H]^+$, $C_{30}H_{30}N_4O_7NaS$ 613.1733 found 613.1719 $[M+Na]^+$.

N-((S)-1-amino-3-(1H-indol-3-yl)-1-oxopropan-2-yl)-2-((2Z,5Z)-5-(4-hydroxy-3,5-dimethoxybenzylidene)-4-oxo-2-(phenylimino)thiazolidin-3-yl)propanamide [TZN51] and (R)-N-((S)-1-amino-3-(1H-indol-3-yl)-1-oxopropan-2-yl)-2-((2Z,5Z)-5-(4-hydroxy-3,5-dimethoxybenzylidene)-4-oxo-2-(phenylimino)thiazolidin-3-yl)propanamide [TZN52] were obtained from 004-149-1 (30 mg, 0.04 mmol) by General Method D and purified on reverse phase HPLC (20 to 95% B in A over 12 min) to give the products, as the TFA salts, from the earlier-eluting D,L-Ala LTrp diastereomaric mix TZN51 (2.7 mg, 0.004 mmol) $^1H$ NMR (500 MHz, $CD_3OD$, d) 1.62 (dd, J=6.6 6.3 Hz, 3H), 3.25-3.32 (m, 2H), 3.83 (s, 6H), 4.60-4.65 (m, 1H), 5.25-5.38 (m, 1H), 6.75-8.10 (m, 13H). MS m/z 614.2 $[M+H]^+$, 636.3 $[M+Na]^+$, 411.4 411.3 $[M-Trp+H]^+$; HRMS calculated for $C_{32}H_{31}N_5O_6S$ 614.2073 found 614.2072 $[M+H]^+$, $C_{32}H_{31}N_5O_6NaS$ 636.1893, found 636.1881 $[M+Na]^+$, and the later-eluting pure D-Ala-L-Trp diastereomer TZN52 (1.3 mg, 0.002 mmol) $^1H$ NMR ($CD_3OD$) d 1.60 (d, J=7.0 Hz, 3H), 3.30-3.34 (m, 2H), 3.85 (s, 6H), 4.62-4.64 (m, 1H), 5.28 (dd, J=7.0, 7.1 Hz, 1H), 6.68-7.67 (m, 13H); MS m/z 614.2 $[M+H]^+$, 636.3 $[M+Na]^+$, 411.4 411.3 $[M-Trp+H]^+$; HRMS calculated for $C_{32}H_{31}N_5O_6S$ 614.2073 found 614.2074 $[M+H]^+$, $C_{32}H_{31}N_5O_6NaS$ 636.1893, found 636.1887 $[M+Na]^+$, $C_{32}H_{31}N_5O_6KS$ 652.1632, found 652.1631 $[M+K]^+$.

(S)-5-amino-N-((S)-1-amino-3-(indolin-3-yl)-1-oxopropan-2-yl)-2-((5Z)-5-(4-hydroxy-3,5-dimethoxybenzylidene)-4-oxo-2-(phenylimino)thiazolidin-3-yl)pentanamide [SRJ3-151B] was obtained from SRJ3-145 (12.0 mg, 0.017 mmol) by General Method D and purified on reverse phase HPLC (10 to 60% B in A over 25 min) to give SRJ3-151B [TZN90] (1.66 mg, 0.0025 mmol) as the TFA salt. $^1H$ NMR (500 MHz, $CD_3OD$, d) 1.19 (m, 2H), 1.64-1.80 (m, 2H), 1.95-2.18 (m, 2H), 2.33 (m, 2H), 2.88-2.98 (m, 2H), 3.53 (m, 2H), 3.71 (s, 6H), 3.86 (m, 1H), 4.58 (dd, J=3, 11 Hz, 1H), 5.40 (m, 1H), 6.65 (s, 2H), 6.95-7.30 (m, 9H), 7.59 (s, 1H). MS m/z 330.3 $[M+2H]^{+2}$, 659.3 $[M+H]^+$. HRMS calculated for $C_{34}H_{39}N_6O_6S$ 659.2652 found 659.2646 $[M+H]^+$, $C_{34}H_{38}N_6NaO_6S$ 681.2471 found 681.2466 $[M+Na]^+$.

(S)-N-((S)-1-amino-3-(1-carbamimidoylindolin-3-yl)-1-oxopropan-2-yl)-5-(diaminomethyleneamino)-2-((5Z)-5-(4-hydroxy-3,5-dimethoxybenzylidene)-4-oxo-2-(phenylimino)thiazolidin-3-yl)pentanamide [SRJ3-157A] was obtained from SRJ3-151 (20 mg, 0.023 mmol) by General Method D and purified on reverse phase HPLC (0 to 60% B in A over 25 min) to give SRJ3-157A [TZN92] (2.75 mg, 0.0037 mmol) as the TFA salt. $^1H$ NMR (500 MHz, $D_2O$, d) 1.30-1.36 (m, 1H), 1.54-1.64 (m, 2H), 2.08 (t, J=12 Hz, 1H), 2.36-2.55 (m, 3H), 2.87 (s, 1H), 3.27 (q, J=6.5 Hz, 2H), 3.49 (s, 6H), 3.61-3.85 (m, 3H), 4.65 (d, J=12.5 Hz, 1H), 5.49 (q, J=4.8 Hz, 1H), 6.13 (br, 2H), 7.01 (d, J=6.6 Hz, 3H), 7.19 (d, J=6.3 Hz, 1H), 7.28-7.41 (m, 5H). MS m/z 372.3 $[M+2H]^{+2}$, 743.4 $[M+H]^+$. HRMS calculated for $C_{36}H_{43}N_{10}O_6S$ 743.3088 found 743.3082 $[M+H]^+$.

(S)-5-amino-2-((S)-2-((2Z,5Z)-5-(4-hydroxy-3,5-dimethoxybenzylidene)-4-oxo-2-(phenylimino)thiazolidin-3-yl)propanamido)pentanamide [TZN54] was obtained from KCB3-047 (102 mg, 0.16 mmol) by General Method D and purified on reverse phase HPLC (10 to 95% B in A over 25 min) to give TZN54 (5.1 mg, 0.008 mmol) as the TFA salt. $^1H$ NMR (300 MHz, $CD_3OD$, d) 1.75 (d, J=7.07 Hz, 3H), 1.79-1.92 (m, 3H), 1.96-2.18 (m, 1H), 2.85-3.05 (m, 2H), 3.83 (s, 6H), 4.44-4.57 (m, 1H), 5.46 (q, J=7.05 Hz, 1H), 6.80 (s, 2H), 7.07 (d, J=7.29 Hz, 2H), 7.22 (t, J=7.44 Hz, 1H), 7.42 (t, J=7.81 Hz, 2H), 7.71 (s, 1H). $^{13}C$ NMR ($CD_3OD$, d) 16.68, 27.73, 31.88, 42.70, 56.37, 56.63, 59.46, 111.69, 121.53, 124.96, 128.35, 128.88, 133.10, 136.01, 142.45, 151.75, 152.23, 153.94, 170.54, 174.39, 178.73. MS m/z 542.3 $[M+H]^+$, 564.3 $[M+Na]^+$. HRMS calculated for $C_{26}H_{32}N_5O_6S$ 542.2073 found 542.2070 $[M+H]^+$, $C_{26}H_{31}N_5O_6NaS$ 564.1893 found 564.1890 $[M+Na]^+$.

2-((2Z,5Z)-5-(4-hydroxy-3,5-dimethoxybenzylidene)-4-oxo-2-(phenylimino)thiazolidin-3-yl)acetic acid [TZN57] was obtained from KCB3-093 (329 mg, 0.70 mmol) by General Method D and purified by silica gel chromatography using a gradient from 0 to 10% MeOH in $CH_2Cl_2$ to give TZN57 (235.7 mg, 0.57 mmol). $^1H$ NMR (300 MHz, DMF-d7, d) 3.70 (br s, 1H), 4.02 (s, 6H), 4.85 (s, 2H), 7.11 (s, 2H), 7.25 (d, J=7.42 Hz, 2H), 7.39 (t, J=7.41 Hz, 1H), 7.62 (t, J=7.80 Hz, 2H), 7.95 (s, 1H), 9.62 (br s, 1H). $^{13}C$ NMR (DMF-d7, d): 53.08, 60.29, 112.39, 112.57, 121.97, 125.50, 128.25, 129.11, 133.61, 133.66, 135.97, 143.49, 152.19, 152.81, 154.10, 170.22. MS m/z 415.4 $[M+H]^+$, 437.4 $[M+Na]^+$. HRMS calculated for $C_{20}H_{18}N_2O_6NaS$ 437.0783 found 437.0787 $[M+Na]^+$.

4-((2Z,5Z)-5-(4-hydroxy-3,5-dimethoxybenzylidene)-4-oxo-2-(phenylimino)thiazolidin-3-yl)butanoic acid [TZN61] was obtained from TZN60 (190 mg, 0.38 mmol) by General Method D and purified by silica gel chromatography using a gradient from 0 to 10% MeOH in $CHCl_3$ to give TZN61 (89 mg, 0.20 mmol). $^1H$ NMR (300 MHz, $CDCl_3$, d) 1.86-2.14 (m, 4H), 2.62 (br s, 1H), 4.00 (s, 6H), 4.07-4.22 (m, 2H), 6.83 (s, 2H), 7.34 (d, J=6.92 Hz, 2H), 7.47-7.64 (m, 3H), 7.84 (s, 1H). $^{13}C$ NMR ($CDCl_3$, d) 13.82, 30.34, 60.59, 68.89, 111.59, 119.77, 128.51, 131.77, 133.89, 133.97, 134.78, 136.46, 137.69, 139.15, 141.96, 151.56, 176.51. MS m/z 443.4 $[M+H]^+$, 465.3 $[M+Na]^+$. HRMS calculated for $C_{22}H_{22}N_2O_6NaS$ 465.1096 found 465.1106 $[M+Na]^+$.

(S)-5-amino-2-((R)-2-((2Z,5Z)-5-(4-hydroxy-3,5-dimethoxybenzylidene)-4-oxo-2-(phenylimino)thiazolidin-3-yl)propanamido)pentanamide [TZN84]. KCB3-180 was prepared by General Method C from KCB3-173 on a 0.58 mmol scale and purified via silica gel chromatography using a gradient from 1 to 10% MeOH in $CH_2Cl_2$. Fractions containing product ($^1H$ NMR (300 MHz, $CDCl_3$, d) 1.35 (s, 9H), 1.50-1.74 (m, 2H), 1.76 (d, J=6.99 Hz, 3H), 1.97-2.15 (m, 1H), 3.00-3.39 (m, 2H), 3.85 (s, 3H), 3.98 (s, 3H), 4.70-5.10 (m, 1H), 5.34 (br s, 1H), 5.44 (q, J=6.86 Hz, 1H), 6.64 (s, 2H), 6.93 (br s, 1H), 7.00 (d, J=7.54 Hz, 2H), 7.19 (t, J=7.03 Hz, 2H), 7.37 (t, J=7.69 Hz, 2H), 7.65 (s, 1H). MS m/z 642.4 $[M+H]^+$, 664.4 $[M+Na]^+$) were treated with neat TFA for 45 min to give, after silica gel chromatography using a gradient from 1 to 10% MeOH in $CH_2Cl_2$, TZN84 (224 mg, 0.34 mmol) as the TFA salt. $^1H$ NMR (300 MHz, $CD_3OD$, d): 1.74 (d, J=7.04 Hz, 3H), 1.77-1.91 (m, 3H), 1.93-2.13 (m, 1H), 2.93 (t, J=6.89 Hz, 2H), 3.79 (s, 6H), 4.44-4.62 (m, 1H), 5.45 (q, J=7.00 Hz, 1H), 6.73 (s, 2H), 7.06 (d, J=7.40 Hz, 2H), 7.20 (t, J=7.41 Hz, 1H), 7.40 (t, J=7.78 Hz, 2H), 7.68 (s, 1H). $^{13}C$ NMR ($CD_3OD$, d): 16.84, 27.72, 32.08, 42.75, 56.41, 56.55, 59.43, 111.67, 121.50, 124.94, 128.37, 128.82, 133.07, 136.10, 142.29, 151.81, 152.14, 153.85, 170.83, 174.34, 178.02. MS m/z 542.4 $[M+H]^+$. HRMS calculated for $C_{26}H_{32}N_5O_6S$ 542.2068 found 542.2064 $[M+H]^+$, $C_{26}H_{31}N_5O_6NaS$ 564.1887 found 564.1882 $[M+Na]^+$.

(S)-5-amino-N-((S)-1-amino-1-oxopropan-2-yl)-2-(2Z,5Z)-5-(4-hydroxy-3,5-dimethoxybenzylidene)-4-oxo-2-

(phenylimino)thiazolidin-3-yl)pentanamide [TZN86]. TZN86 was obtained from KCB3-197 (117 mg, 0.18 mmol) by General Method D and purified on reverse phase HPLC (10 to 75% B in A over 30 min) to give TZN86 (24.2 mg, 0.037 mmol) as the TFA salt. $^1$H NMR (300 MHz, $CD_3OD$, d) 1.39 (d, J=7.20 Hz, 3H), 1.62-1.94 (m, 2H), 2.38 (q, J=8.00 Hz, 2H), 2.94-3.11 (m, 2H), 3.84 (s, 6H), 4.44 (q, J=7.18 Hz, 1H), 5.37 (t, J=7.41 Hz, 1H), 6.82 (s, 2H), 7.05 (d, J=7.38 Hz, 2H), 7.22 (t, J=7.41 Hz, 1H), 7.42 (t, J=7.81 Hz, 2H), 7.74 (s, 1H). $^{13}$C NMR ($CD_3OD$, d) 20.70, 28.17, 28.77, 42.99, 53.25, 59.46, 59.99, 111.67, 121.37, 124.84, 128.36, 128.89, 133.07, 136.18, 151.65, 152.21, 153.65, 170.80, 173.07, 180.34. MS m/z 542.2 $[M+H]^+$. HRMS calculated for $C_{26}H_{32}N_5O_6S$ 542.2068 found 542.2071 $[M+H]^+$, $C_{26}H_{31}N_5O_6NaS$ 564.1887 found 564.1888 $[M+Na]^+$.

(S)-5-amino-N-((S)-1-amino-3-(biphenyl-4-yl)-1-oxopropan-2-yl)-2-(2Z,5Z)-5-(4-hydroxy-3,5-dimethoxybenzylidene)-4-oxo-2-(phenylimino)thiazolidin-3-yl)pentanamide [TZN91]. TZN91 was obtained from KCB4-008 (41 mg, 0.052 mmol) by General Method D and purified on reverse phase HPLC (10 to 75% B in A over 30 min) to give TZN91 (6.0 mg, 0.007 mmol) as the TFA salt. $^1$H NMR (300 MHz, $CD_3OD$, d) 1.60-1.87 (m, 2H), 2.35 (q, J=7.57 Hz, 2H), 2.94-3.13 (m, 3H), 3.16-3.28 (m, 1H), 3.77 (s, 6H), 4.56-4.71 (m, 1H), 5.35 (t, J=7.45 Hz, 1H), 6.72 (s, 2H), 6.91 (d, J=7.50 Hz, 2H), 7.17 (t, J=7.39 Hz, 1H), 7.21-7.37 (m, 8H), 7.40 (d, J=8.05 Hz, 2H), 7.67 (d, J=7.08 Hz, 1H), 7.69 (s, 1H). $^{13}$C NMR ($CD_3OD$, d) 28.07, 28.23, 40.68, 42.96, 58.62, 59.40, 59.90, 111.62, 120.88, 124.93, 128.22, 128.86, 130.27, 130.75, 130.80, 132.29, 132.95, 133.21, 136.48, 139.92, 142.50, 143.45, 144.37, 151.31, 152.22, 153.48, 170.36, 172.94, 178.77. MS m/z 694.6 $[M+H]^+$. HRMS calculated for $C_{38}H_{40}N_5O_6S$ 694.2694 found 694.2687 $[M+H]^+$, $C_{38}H_{39}N_5O_6NaS$ 716.2523 found 716.2513 $[M+Na]^+$.

Scheme II

General Method E for amidation is illustrated by the preparation of (S)-benzyl-1-amino-3-(4-t-butoxyphenyl)-1-oxopropan-2-ylcarbamate [004-85-2]. 004-85-2. To a suspension of (S) Cbz tyrosine t-butyl ether DCHA salt (552 mg, 1 mmol) in 2:5 THF: dimethoxyethane was added N-methyl morpholine (250 mL, 2.2 mmol). The reaction mixture was cooled on an ice bath, and isobutyl chloroformate (160 mL, 1.2 mmol) was added. After 1 h of stirring on ice, concentrated $NH_4OH$ (300 mL, 5 mmol) was added, and the reaction mixture stirred an additional 30 min. The reaction mixture was partitioned between 4:1 $CHCl_3$:isopropanol and saturated aqueous sodium carbonate. The organic phase was separated, washed with saturated brine, dried over $Na_2SO_4$, and concentrated in vacuo. The crude product was purified on silica gel using a gradient from 0 to 10% MeOH in $CH_2Cl_2$ to give 004-85-2 (393 mg, 1 mmol). $^1$H NMR (300 MHz, $CDCl_3$, d).1.36 (s, 9 H), 3.02(d, J=6.0 Hz, 2H), 4.43 (m, 1H), 5.08 (s, 2H), 6.92 (d, J=7.5 Hz, 2H) 7.10 (d, J=7.5 Hz, 2H), 7.28-7.37 (m, 5H). $^{13}$C NMR (500 MHz, $CDCl_3$, ḑ ) 32.88, 41.86, 59.96, 70.98, 82.45, 128.28, 131.95, 132.18, 132.56, 133.83, 135.43, 140.24, 158.27, 160.24, 178.19. MS m/z 371.3 $[M+H]^+$, 393.3$[M+Na]^+$.

(S)-t-Butyl-3-(3-amino-2-(benzyloxycarbonylamino)-3-oxopropyl)-1H-indole-1-carboxylate [004-75-3] was prepared on a 1.6 mmol scale according to General Method E to yield, after silica gel chromatography, 382 mg (0.87 mmol) product. $^1$H NMR (300 MHz, $CDCl_3$, d).1.67(s, 9H), 3.19-3.20 (m, 2H), 4.64-4.65 (m, 1H), 5.06 (s, 1H), 6.21(br, 2H), 7.19-7.63 (m, 5H), 8.13 (br, 1H) s. MS m/z 438.4 $[M+H]^+$, 460.3$[M+Na]^+$, 476.2$[M+K]^+$,420.3 $[M-tBu+H]^+$, 404.4 $[M-tBu+Na]^+$, 338.3 $[M-Boc+H]^+$, 338.3 $[M-Boc+Na]^+$.

t-Butyl-3-((S)-2,3-diamino-3-oxopropyl)indoline-1-carboxylate [SRJ3-129] was prepared on a 0.64 mmol scale from (S) Fmoc±Dihydrotryptophane(Boc) according to General Method E followed by N-a deprotection in 20% piperidine in DMF to yield, after silica gel chromatography, 102.89 mg (0.34 mmol) product. $^1$H NMR (300 MHz, $CDCl_3$, ḑ ) 1.24 (s, 9H), 1.53 (s, 9H), 1.78 (m, 1H), 2.01 (m, 2H), 2.22 (m, 1H), 2.61 (br, 2H), 3.52-3.67 (m, 6H), 4.12 (br, 2H), 6.89-6.92 (m, 4H), 7.13-7.16 (m, 4H); $^{13}$C NMR (500 MHz, $CDCl_3$, d).28.33, 29.64, 36.46, 40.70, 52.99, 53.87, 114.70, 114.80, 122.32, 124.14, 127.92. MS m/z 306.2 $[M+H]^+$.

(S)-2-amino-3-(biphenyl-4-yl)propanamide [SRJ3-127] was prepared on a 0.66 mmol scale according to General Method E followed by deprotection in 20% piperidine in DMF to yield, after silica gel chromatography, 121 mg (0.50 mmol, 76%) product. $^1$H NMR (300 MHz, $CDCl_3$, d).2.78 (dd, J=9.5, 13.7 Hz, 2H), 3.31 (dd, J=3.9, 13.7 Hz, 2H), 3.64-3.67 (m, 2H), 5.67 (br, 1H), 7.3-7.36 (m, 2H), 7.42-7.45 (m, 2H), 7.55-7.59 (m, 5H); $^{13}$C NMR (500 MHz, $CDCl_3$, d).29.68, 40.53, 56.40, 126.96, 127.27, 127.44, 128.77, 129.70, 136.80, 139.82, 140.16. MS m/z 241.1 $[M+H]^+$.

(S)-Benzyl-1-amino-5-t-butoxycarbonylamino-1-oxopentan-2-ylcarbamate [KCB3-015] was prepared on a 2.0 mmol scale according to General Method E to yield, after silica gel chromatography using a gradient from 0 to 25% MeOH in $CH_2Cl_2$, 670.2 mg (1.84 mmol) product. $^1$H NMR (500 MHz, $CD_3OD$, d) 1.46 (s, 9H), 1.51-1.72 (m, 3H), 1.72-1.88 (m, 1H), 2.99-3.16 (m, 2H), 4.07-4.18 (m, 1H), 5.05-5.22 (m, 2H), 7.26-7.46 (m, 5H). $^{13}$C NMR ($CD_3OD$, d): 30.08, 31.38, 33.31, 43.37, 58.45, 70.31, 82.55, 131.48, 131.63, 132.08, 140.78, 161.08, 180.17. MS m/z 366.3 $[M+H]^+$, 388.3 $[M+Na]^+$.

(S)-Benzyl 1-amino-1-oxopropan-2-ylcarbamate [KCB3-160] was prepared on a 2.0 mmol scale according to General Method E to yield, with no further purification, 411 mg (1.85 mmol) product. $^1$H NMR (300 MHz, $CD_3OD$, d) 1.36 (d, J=7.16 Hz, 3H), 4.15 (q, J=7.20 Hz, 1H), 5.11 (s, 2H), 7.11-7.56 (m, 5H). MS m/z 245.1 $[M+Na]^+$.

General Method F for hydrogenolysis, coupling, and subsequent deprotection to the free a-amino dipeptide amide is illustrated by the synthesis of (S)-2-amino-N-((S)-1-amino-3-(4-t-butoxyphenyl)-1-oxopropan-2-yl)propanamide [004-101-1]. N-Protected 004-85-2 (341 mg, 0.92 mmol) was hydrogenated over 10% palladium on carbon (40 mg) in 40 mL EtOH for 3 h. The catalyst was filtered off and the filtrate concentrated in vacuo to give 004-91-1 (173 mg, 0.73 mmol) which was used without further purification. $^1$H NMR (500 MHz, $CD_3OD$, ḑ 1.40 (s, 9H), 2.88 (dd, J=7.7, 5.9 Hz, 1 H), 3.10 (dd, J=7.9, 5.9 Hz, 1 H),3.70 (dd, J=6.8, 5.6 Hz, 1H), 7.02 (dd, J=7.7, 1.5 2H), 7.24 (dd, J=6.8, 1.5 2H). MS m/z 237.1 [M+H]. Tetrahydrofuran (1 mL) was added to a dry mixture of Cbz L-alanine (164 mg, 0.73 mmol) and carbonyldiimidazole (143 mg, 0.88 mmol), and the reaction mixture allowed to stir for 2 h. To this was added amine 004-91-1, along with triethylamine (112 mL, 0.81 mmol), and the reaction mixture stirred for 2 days until determined complete by TLC (95:5 $CHCl_3$:MeOH). The volatiles were removed in vacuo, and a 4% aqueous solution of $NaHCO_3$ (3 mL) was added to precipitate the product. The crude solid was collected and purified on silica gel using a gradient from 1 to 50% MeOH in $CHCl_3$ to give 004-98-2 (182 mg, 0.41 mmol). $^1$H NMR (300 MHz, $(CD_3)_2CO$, d) 1.29 (d, J=7.2 Hz, 3H), 1.34 (s, 9H), 2.91 (dd, J=8.3, 5.5 Hz, 1H), 3.13 (dd, J=8.8, 5.1 Hz, 1 H), 4.11-4.16 (m, 1 Hz), 4.58-4.65 (m, 1H), 5.07 (d, J=5.8 Hz, 2H), 6.42 (br, 1H), 6.58 (br, 1H), 6.90 (dd, J=7.7, 1.5 Hz, 2H), 7.14 (dd, J=7.7, 1.5 Hz, 2H), 7.36-7.89 (m, 5H). MS m/z 442.4$[M+H]^+$, 425.3 $[M-NH_2+H]^+$, 386.3[M−tBu+

H]$^+$369.3[M $NH_2$−tBu+H]$^+$. Hydrogenolysis of the Cbz group over 10% palladium on carbon (20 mg) in 15 mL EtOH for 20 h gave 004-101-1 (109 mg, 0.36 mmol). $^1$H NMR (300 MHz, $CD_3OD$, d) 1.15 (d, J=7.0 Hz, 3H), 1.32 (s, 9H), 2.93 (dd, J=8.9, 5.7 Hz, 1 H), 3.17 (dd, J=8.1, 5.7 Hz, 1H), 3.40 (m, 1 Hz), 4.61 (dd, J=5.7, 3.2 Hz, 1H), 6.42 (br, 1H), 6.58 (br, 1H), 6.92 (dd, J=6.5, 2.0 Hz, 2H), 7.18 (d, J=8.4 Hz, 2H), 7.36-7.89 (m, 5H). MS m/z 308.2 [M+H]$^+$, 330.2 [M+Na]$^+$, 291 [M−$NH_2$+H]$^+$263.3 [M−C($CH_3$)$NH_2$+H]$^+$.

t-Butyl-3-((S)-3-amino-2-((S)-2-aminopropanamido)-3-oxopropyl)-1H-indole-1-carboxylate [004-143-1] was prepared by General Method F on a 0.83 mmol scale via the deprotection of 004-75-3 to free amine 004-137-1 (220 mg, 0.73 mmol) $^1$H NMR (300 MHz, $CD_3OD$, δ) 1.40 (s, 9H), 2.87-2.90 (m, 1H), 3.50-3.52 (m, 1H), 3.76(m, 1H), 6.99-7.05 (m, 2H), 7.34 (s, 1H), 7.44-7.46 (m, 1H), 7.83-7.85 (m, 1H). MS m/z 304.1 [M+H]$^+$, [M+Na]$^+$, followed by reaction to the protected dipeptide 004-138-2 (153 mg, 0.30 mmol) ($^1$H NMR (300 MHz, $(CD_3)_2O$, δ) 1.33 (d, J=7.1 Hz, 3H), 1.67 (s, 9H), 3.10 (dd, J=7.8, 9.7 Hz, 1H), 3.28 (dd, J=5.1, 9.7 Hz, 1H), 4.15-4.20 (m, 1H), 4.74 (dt, J=5.5, 8.0, 5.5 Hz, 1H), 5.05 (d, J=7.1 Hz, 2H), 6.49 (br, 2H), 7.03 (br, 1H), 7.25-7.72 (m, 10H), 8.14 (m, 1H). MS m/z 509.5 [M+H]$^+$, 531.6 [M+Na]$^+$, 475.4 [M−tBu+Na]$^+$), and finally hydrogenolysis to the a-amino dipeptide amide (90.0 mg, 0.24 mmol) $^1$H NMR (300 MHz, $CD_3OD$, d) 1.41 (d, J=6.9 Hz, 3H), 1.44 (s, 9H), 2.86-3.07 (m, 2H), 3.36 (q, 6.4 Hz, 1H), 4.50 (dd, J=6.1 6.0 Hz, 1H), 7.07-7.09 (m, 2H), 7.29 (s, 1H), 7.44-7.46 (m, 1H), 7.84-7.86 (m, 1H). $^{13}$C NMR (500 MHz, $CD_3OD$, d) 20.97, 29.78, 49.69, 52.16, 55.50, 86.03, 117.26, 118.51, 121.35, 124.84, 126.46, 126.64, 131.39, 132.86, 137.89, 152.11, 176.48, 177.05. MS m/z 375.3[M+H]$^+$, 397.4[M+Na]$^+$.

t-Butyl-(S)-4-amino-5-((S)-1-amino-3-(biphenyl-4-yl)-1-oxopropan-2-ylamino)-5-oxopentylcarbamate [SRJ3-131] was prepared by adding tetrahydrofuran (3 mL) to a dry mixture of Cbz L-Ornithine Boc (27.6 mg, 0.075 mmol) and carbonyldiimidazole (15 mg, 0.093 mmol) and the reaction mixture was allowed to stir for 1 h. To this was added amine SRJ3-123, along with diisopropylethylamine (20 mL, 0.11 mmol), and the reaction mixture stirred for 18 hours until determined complete by TLC (85:15 $CHCl_3$: MeOH). A saturated solution of $NaHCO_3$ (5 mL), water (15 mL), and chloroform (10 mL) were added and the layers were separated. The resulting organic layer was rinsed with a saturated solution of NaCl (10 mL), concentrated in vacuo, and purified on silica gel using a gradient from 0 to 10% MeOH in $CHCl_3$ to give SRJ3-131 (13.26 mg, 0.022 mmol) $^1$H NMR (300 MHz, $CD_3OD$, d) 0.29 (s, 9H), 0.43 (m, 2H), 0.57 (m, 2H), 1.86-1.94 (m, 4H), 2.59 (s, 2H), 2.92-2.95 (m, 1H), 3.07-3.09 (m, 1H), 3.54-3.57 (m, 1H), 3.92-3.98 (m, 2H), 6.18-6.29 (m, 9H), 6.38-6.44 (m, 5H). MS m/z 589.4 [M+H]$^+$.

t-Butyl-3-((S)-3-amino-2-(S)-2-amino-5-(t-butoxycarbonylamino)pentamido)-3-oxopropyl)indoline-1-carboxylate [SRJ3-133a] was prepared by adding tetrahydrofuran (3 mL) to a dry mixture of Cbz L-Ornithine Boc (25.7 mg, 0.070 mmol) and carbonyldiimidazole (14 mg, 0.086 mmol) and the reaction mixture was allowed to stir for 1 h. To this was added amine SRJ3-125, along with diisopropylethylamine (20 mL, 0.11 mmol), and the reaction mixture stirred for 18 hours until determined complete by TLC (85:15 $CHCl_3$:MeOH). A saturated solution of $NaHCO_3$ (5 mL), water (15 mL), and chloroform (10 mL) were added and the layers were separated. The resulting organic layer was rinsed with a saturated solution of NaCl (10 mL), concentrated in vacuo, and purified on silica gel using a gradient from 0 to 10% MeOH in $CHCl_3$ to give SRJ3-133a (17.68, 0.026 mmol). $^1$H NMR (300 MHz, $CD_3OD$, d) 0.28 (s, 9H), 0.43 (s, 9H), 0.69-0.80 (m, 2H), 0.94-1.05 (m, 2H), 1.93 (t, J=6.5, 2H), 2.22 (s, 2H), 2.55 (m, 2H) 3.40 (m, 2H), 3.89-3.96 (m, 2H), 5.81-5.83 (m, 2H), 6.02-6.17 (m, 7H), 6.51 (br, 1H). MS m/z 654.3 [M+H].

(S)-2-amino-N-((S)-1-amino-1-oxopropan-2-yl)propanamide [KCB3-002]. TK-004-106-1 (891 mg, 3.0 mmol) was hydrogenated over 10% palladium on carbon (420 mg) in 1:1 EtOH:DMF (55 mL) for 3 h. The catalyst was filtered off and the filtrate concentrated in vacuo to give KCB3-002 (414 mg, 2.71 mmol). $^1$H NMR (300 MHz, $CD_3OD$, d) 1.29 (d, J=6.90, 3H), 1.39 (d, J=6.90 Hz, 3H), 3.44 (q, J=6.91 Hz, 1H), 4.35 (q, J=6.66 Hz, 1H). MS m/z 160.2 [M+H]$^+$, 182.1 [M+Na]$^+$.

t-Butyl-(S)-5-amino-4-((S)-2-aminopropanamido)-5-oxopentylcarbamate (KCB3-027). KCB3-027 was prepared by General Method F on a 1.82 mmol scale via free amine KCB3-019 ($^1$H NMR (300 MHz, $CD_3OD$, d) 1.45 (s, 9H), 1.51-1.65 (m, 3H), 1.65-1.84 (m, 1H), 3.07 (t, J=6.19 Hz, 2H), 3.09-3.24 (m, 1H). $^{13}$C NMR ($CD_3OD$, d) 29.79, 31.38, 36.25, 43.59, 57.99, 82.49, 158.63, 180.28. MS m/z 232.1 [M+H]$^+$, 254.1 [M+Na]$^+$) to the protected dipeptide KCB3-021b (226.1 mg, 0.52 mmol) $^1$H NMR (300 MHz, $CD_3OD$, d) 1.36 (d, J=7.17 Hz, 3H), 1.44 (s, 9H), 1.48-1.74 (m, 3H), 1.76-1.94 (m, 1H), 2.97-3.12 (m, 2H), 4.15 (q, J=7.10 Hz, 1H), 4.27-4.41 (m, 1H), 5.13 (s, 2H), 7.26-7.43 (m, 5H). MS m/z 437.5 [M+H]$^+$, 459.4 [M+Na]$^+$ to the a-amino dipeptide amide KCB3-027 (147.8 mg, 0.49 mmol) $^1$H NMR (300 MHz, $CD_3OD$, d) 1.30 (d, J=6.94 Hz, 3H), 1.45 (s, 9H), 1.50-1.75 (m, 3H), 1.77-1.89 (m, 1H), 3.08 (td, J=6.57, 1.69 Hz, 2H), 3.48 (q, J=6.92 Hz, 1H), 4.30-4.49 (m, 1H). MS m/z 303.3 [M+H]$^+$.

t-Butyl-(S)-5-amino-4-((R)-2-aminopropanamido)-5-oxopentylcarbamate [KCB3-162] was prepared by General Method F on a 1.82 mmol scale via free amine KCB3-148 (MS m/z 232.2 [M+H]$^+$, 254.2 [M+Na]$^+$); taken on crude to the protected dipeptide KCB3-154 (545.2 mg, 1.25 mmol) $^1$H NMR (300 MHz, $CDCl_3$, d) 1.42 (d, J=7.06 Hz, 3H), 1.45 (s, 9H), 1.50-1.58 (m, 3H), 1.83-1.99 (m, 1H), 3.01-3.22 (m, 1H), 3.27-3.51 (m, 1H), 4.19-4.37 (m, 1H), 4.52-4.71 (m, 1H), 4.77 (br s, 1H), 5.12 (d, J=2.38 Hz, 2H), 5.39 (br s, 2H), 6.76 (br s, 1H), 7.05 (br s, 1H), 7.32-7.50 (m, 5H). MS m/z 437.4 [M+H]$^+$, 459.3 [M+Na]$^+$ to the dipeptide amide KCB3-162 (281.3 mg, 0.93 mmol) $^1$H NMR (300 MHz, $CD_3OD$, d) 1.29 (d, J=6.90, 3H), 1.45 (s, 9H), 1.49-1.76 (m, 3H), 1.78-1.95 (m, 1H), 3.08 (t, J=6.24 Hz, 2H), 3.48 (q, J=6.95 Hz, 1H), 4.29-4.44 (m, 1H). MS m/z 303.2 [M+H]$^+$, 325.2 [M+Na]$^+$.

t-Butyl-(S)-4-amino-5-((S)-1-amino-1-oxopropan-2-ylamino)-5-oxopentylcarbamate [KCB3-178] was prepared by General Method F on a 1.85 mmol scale via free amine KCB3-169 (76.6 mg, 0.87 mmol) ($^1$H NMR (300 MHz, $CD_3OD$, d) 1.30 (d, J=6.94 Hz, 3H), 3.44 (q, J=6.93 Hz, 1H); MS m/z 89.2 [M+H]$^+$) to the protected dipeptide KCB3-171 (222.5 mg, 0.51 mmol) ($^1$H NMR (300 MHz, $CDCl_3$, d) 1.41 (d, J=6.87 Hz, 3H), 1.46 (s, 9H), 1.64-2.02 (m, 4H), 3.01-3.20 (m, 1H), 3.26-3.47 (m, 1H), 4.47 (t, J=7.12 Hz, 1H), 4.66-4.81 (m, 1H), 5.13 (s, 2H), 5.27 (br s, 1H), 5.59 (br s, 1H), 6.26 (br s, 1H), 6.87 (br s, 1H), 7.32-7.66 (m, 5H); MS m/z 459.4 [M+Na]$^+$) to the a-amino dipeptide amide KCB3-178 (122.4 mg, 0.41 mmol) ($^1$H NMR (300 MHz, $CD_3OD$, d) 1.39 (d, J=7.16 Hz, 3H), 1.44 (s, 9H), 1.50-1.63 (m, 3H), 1.63-1.80 (m, 1H), 3.06 (t, J=6.45 Hz, 2H), 3.25-3.54 (br, solvent envelope over CH), 4.38 (q, J=7.21 Hz, 1H); MS m/z 303.2 [M+H]$^+$, 325.2 [M+Na]$^+$).

General Method G for the formation of N-phenyl-N'-amidodipeptidyl thioureas is illustrated by the preparation of 004-104-1. To a solution of 004-101-1 (109 mg, 0.36 mmol) in 1 mL MeOH was added phenylisothiocyanate (85 mL, 0.71 mmol) and the reaction mixture stirred overnight, during which time the product precipitated. The volatiles were removed in vacuo, diethylether was added, and the suspension cooled at 4° C. for 1 h. The crude thiourea was collected and washed with diethyl ether to give 004-104-1 (90 mg, 0.20 mmol) which could be used without further purification. $^1$H NMR (300 MHz, $(CD_3)_2CO$, d 1.39 (s, 9H), 1.43 (d, J=7.1 Hz, 3H), 2.07 (br, 1), 2.91 (dd, J=9.2, 4.7 Hz 1H), 3.19 (dd, J=9.0, 5.0 Hz, 1H), 4.61-4.63 (m, 1H), (H), 4.86-4.87 (m, 1H), 6.83 (br, 1H), 6.87-6.89 (m, 2H), 7.15-7.69 (m, 7H), 9.42 (br, 2H). $^{13}$C NMR (500 MHz, $(CD_3)_2CO$, d 21.60, 32.24, 40.71, 57.83, 58.30, 81.67, 127.56, 127.83, 128.89, 132.80, 133.81, 16.53, 158.07, 176.53, 177.64, 184.95. MS m/z 352.3 [M−PhNH+H]$^+$, 443.2 [M+H]$^+$, 465.4 [M+Na]$^+$, 481.3 [M+K]$^+$.

t-Butyl-3-((S)-3-amino-3-oxo-2-((S)-2-(3-phenylthioureido)propanamido)-propyl)-1H-indole-1-carboxylate [004-114-2] was prepared by General Method G on a 0.19 mmol scale to give, after silica gel purification using a gradient of 0 to 10% MeOH in $CHCl_3$ 004-114-1 (67 mg, 0.13 mmol) $^1$H NMR ($(CD_3)_2CO$) d 1.26 (d, J=7.0 Hz, 3 Hz, 1.65 (s, 9H), 3.12 (dd, J=8.3, 6.5 Hz, 1 H), 3.34 (dd, J=9.3, 5.4 Hz, 1 H), 4.78-4.79 (m, 1H), 4.79 (m, 1H), 6.6-6.7 (br, 1H), 7.16-8.14 (m, 10H), 9.14 (br 1H). MS m/z 510.3 [M+H]$^+$, 532.3[M+Na]$^+$.

(S)-N-((S)-1-amino-1-oxopropan-2-yl)-2-(3-phenylthioureido)propanamide [KCB3-004]. KCB3-004 was prepared by General Method G on a 1.86 mmol scale to yield 448.9 mg (1.53 mmol) product. $^1$H NMR (300 MHz, $CD_3OD$, d): 1.38 (d, J=6.90 Hz, 3H), 1.43 (d, J=6.90 Hz, 3H), 3.34-3.44 (m, 1H), 4.27-4.47 (m, 1H), 7.12-7.56 (m, 5H). $^{13}$C NMR ($CD_3OD$, d): 20.81, 21.19, 53.05, 58.17, 128.56, 129.99, 133.51, 134.29, 178.78, 181.27, 186.08. MS m/z 317.1 [M+Na]$^+$.

t-Butyl-(S)-5-amino-5-oxo-4-((S)-2-(3-phenylthioureido) propanamido)pentyl-carbamate [KCB3-031] was prepared by General Method G on a 0.48 mmol scale to yield 204.1 mg, (0.47 mmol) product. $^1$H NMR (500 MHz, $CD_3OD$, d) 1.45 (s, 9H), 1.46 (d, J=7.39 Hz, 3H), 1.51-1.65 (m, 2H), 1.65-1.76 (m, 1H), 1.85-1.94 (m, 1H), 2.98-3.17 (m, 2H), 4.32-4.44 (m, 1H), 4.97 (q, J=7.02 Hz, 1H), 7.22 (t, J=7.30 Hz, 1H), 7.39 (t, J=7.85 Hz, 2H), 7.45 (d, J=7.89 Hz, 2H). MS m/z 438.3 [M+H]$^+$, 460.3 [M+Na]$^+$.

t-Butyl-2-(3-phenylthioureido)acetate [KCB3-083] was prepared by General Method G on a 1.19 mmol scale, but allowed to react for five hours to go to completion. Yield: 285 mg, 1.07 mmol. $^1$H NMR (300 MHz, $CD_3OD$, d) 1.50 (s, 9H), 4.25 (s, 2H), 7.12-7.45 (m, 5H). MS m/z 289.1 [M+Na]$^+$.

t-Butyl-(S)-5-amino-5-oxo-4-((R)-2-(3-phenylthioureido)propanamido)pentyl-carbamate [KCB3-165] was prepared by General Method G on a 0.93 mmol scale, but allowed to react for 2 days to go to completion to give 274 mg (0.63 mmol) product. $^1$H NMR (300 MHz, $CD_3OD$, d) 1.45 (s, 9H); 1.45 (d, J=6.85 Hz, 3H), 1.51-1.80 (m, 3H), 1.85-2.20 (m, 1H), 3.08 (t, J=6.64 Hz, 2H), 4.26-4.40 (m, 1H), 4.94 (q, J=7.10 Hz, 1H), 7.14-7.25 (m, 1H), 7.32-7.58 (m, 4H). MS m/z 438.4 [M+H]$^+$, 460.3 [M+Na]$^+$.

t-Butyl-(S)-5-((S)-1-amino-1-oxopropan-2-ylamino)-5-oxo-4-(3-phenylthioureido)pentylcarbamate [KCB3-184] was prepared by General Method G on a 0.40 mmol scale to yield 164.5 mg (0.38 mmol) product. $^1$H NMR (300 MHz, $CDCl_3$, d) 1.46 (s, 9H), 1.48-1.83 (m, 6H), 1.86-2.04 (m, 1H), 3.04-3.20 (m, 1H), 3.33-3.62 (m, 1H), 4.39-4.57 (m, 1H), 4.80 (br s, 1H), 5.03-5.28 (m, 1H), 5.32 (br s, 1H), 6.31 (br s, 1H), 6.93 (br s, 1H), 7.12 (br s, 1H), 7.30-7.42 (m, 3H), 7.47 (t, J=7.34 Hz, 2H). MS m/z 438.4 [M+H]$^+$, 460.3 [M+Na]$^+$.

t-Butyl-(S)-5-(S)-1-amino-3-(biphenyl-4-yl)-1-oxopropan-2-ylamino)-5-oxo-4-(3-phenylthioureido)pentylcarbamate [KCB3-224]. SRJ3-139 (127 mg, 0.22 mmol) was hydrogenated over 10% palladium on carbon (130 mg) in a mixture of 10 mL EtOH and 1.5 mL DMF for 4 h. The catalyst was filtered off and the filtrate concentrated in vacuo to give KCB3-218 (MS m/z 455.3 [M+H]$^+$) which was reacted crude with phenylisothiocyanate by General Method G to yield, after silica gel purification using a gradient of 1 to 10% MeOH in $CH_2Cl_2$, 48 mg (0.08 mmol) product. $^1$H NMR (500 MHz, $CDCl_3$, d) 1.48 (s, 9H), 1.64-1.80 (m, 2H), 1.80-1.98 (m, 2H), 2.74-3.36 (m, 4H), 4.58-4.82 (m, 1H), 4.91 (br s, 1H), 5.03-5.34 (m, 1H), 5.92 (br s, 1H), 6.63 (br s, 1H), 7.03-7.72 (m, 14H), 8.37 (br s, 1H). MS m/z 590.3 [M+H]$^+$, 612.3 [M+Na]$^+$.

(S)-5-Guanidino-2-((S)-2-((2Z,5Z)-5-(4-hydroxy-3,5-dimethoxybenzylidene)-4-oxo-2-(phenylimino)thiazolidin-3-yl)propanamido)pentanamide [TZN56]. General Method H for addition of bis-Boc-guanidine and subsequent deprotection to the free guanidine is illustrated by the synthesis of TZN56. 1,3-bis-(Boc)-2-methyl-2-thiopseudourea (80 mg, 0.28 mmol), triethylamine (114 μL, 0.82 mmol), and $HgCl_2$ (90 mg, 0.33 mmol) were added to a solution of TZN54 (150 mg, 0.23 mmol) in 2.8 mL DMF at 0° C. The reaction mixture stirred for one hour at 0° C. then at room temperature overnight. The reaction mixture was diluted with ethyl acetate, filtered over celite, and the filtrate concentrated in vacuo. The crude solid was purified via silica gel chromatography using a gradient from 0 to 50% MeOH in $CH_2Cl_2$ to give TZN55 (80.7 mg, 0.10 mmol). $^1$H NMR (300 MHz, $(CD_3)_2CO$, d): 1.45 (s, 9H), 1.50 (s, 9H), 1.60-1.72 (m, 3H), 1.75 (d, J=7.05 Hz, 3H), 1.83-1.96 (m, 1H), 3.24-3.51 (m, 2H), 3.83 (s, 6H), 4.48-4.62 (m, 1H), 5.40 (q, J=7.00 Hz, 1H), 6.47 (br s, 1H), 6.86 (s, 2H), 7.01 (br s, 1H), 7.08 (d, J=7.29 Hz, 2H), 7.19 (t, J=7.43 Hz, 1H), 7.41 (t, J=7.80 Hz, 2H), 7.67 (s, 1H), 7.69-7.77 (m, 1H), 8.32 (br s, 1H); $^{13}$C NMR ($(CD_3)_2CO$, d): 17.26, 29.69, 31.26, 31.60, 31.65, 44.05, 56.82, 59.91, 60.01, 82.21, 86.75, 112.08, 122.37, 125.27, 128.55, 128.80, 133.29, 135.41, 142.65, 151.95, 152.21, 153.30, 160.23, 167.67, 169.58, 169.88, 172.26, 177.41; MS m/z 784.5 [M+H]$^+$, 806.4 [M+Na]$^+$. TZN55 was taken up in 50:50 $CH_2Cl_2$:TFA (3 mL) and stirred at room temperature for one hour, then concentrated in vacuo. The crude solid was purified by preparative reverse phase HPLC using a gradient from 10 to 50% B in A over 30 min to give TZN56 (2 mg, 0.003 mmol) as the TFA salt. $^1$H NMR (300 MHz, $CD_3OD$, d): 1.57-1.73 (m, 3H), 1.74 (d, J=7.02 Hz, 3H), 1.93-2.12 (m, 1H), 3.07-3.28 (m, 2H), 3.82 (s, 6H), 4.43-4.55 (m, 1H), 5.45 (q, J=6.91 Hz, 1H), 6.78 (s, 2H), 7.06 (d, J=7.55 Hz, 2H), 7.21 (t, J=7.37 Hz, 1H), 7.41 (t, J=7.68 Hz, 2H), 7.68 (s, 1H); $^{13}$C NMR ($CD_3OD$, d): 16.80, 29.04, 32.35, 44.53, 56.66, 56.98, 59.44, 111.61, 121.54, 125.00, 128.43, 128.85, 133.07, 135.98, 142.17, 151.70, 152.12, 153.66, 161.22, 170.49, 174.53, 179.20; MS m/z 584.5 [M+H]$^+$. HRMS calculated for $C_{27}H_{34}N_7O_6S$ 584.2286 found 584.2306 [M+H]$^+$.

(S)-5-guanidino-2-((R)-2-((2Z,5Z)-5-(4-hydroxy-3,5-dimethoxybenzylidene)-4-oxo-2-(phenylimino)thiazolidin-3-yl)propanamido)pentanamide (TZN85) was prepared by General Method H via the free amine TZN84 (200 mg, 0.37 mmol), purified via silica gel chromatography using a gradient from 1 to 20% MeOH in $CH_2Cl_2$ to give the bis-Boc guanidine KCB3-195 (226 mg, 0.29 mmol). $^1$H NMR (300 MHz, $CD_3OD$, d) 1.47 (s, 9H), 1.52 (s, 9H), 1.61-1.85 (m, 3H), 1.76 (d, J=6.91 Hz, 3H), 1.88-2.07 (m, 1H), 3.22-3.46 (br, solvent envelope over $CH_2$), 3.82 (s, 6H), 4.45-4.56 (m, 1H), 5.37-5.55 (m, 1H), 6.79 (s, 2H), 7.04 (d, J=7.69 Hz, 2H), 7.19 (t, J=7.20 Hz, 1H), 7.39 (t, J=7.05 Hz, 2H), 7.71 (s, 1H). $^{13}$C NMR ($CD_3OD$, d) 16.87, 29.54, 30.85, 30.94, 31.20, 43.90, 56.60, 57.23, 59.45, 82.99, 87.02, 110.59, 111.67, 121.77, 124.92, 128.45, 128.69, 133.00, 135.93, 151.86, 152.18, 156.57, 156.72, 160.26, 167.17, 170.69, 174.19, 179.28. MS m/z 784.6 $[M+H]^+$; 806.3.6 $[M+Na]^+$ to the free guanidine, purified on reverse phase HPLC (10 to 75% B in A over 30 min), TZN85 (2.0 mg, 0.003 mmol) as the TFA salt. $^1$H NMR (300 MHz, $CD_3OD$, d) 1.57-1.73 (m, 3H), 1.75 (d, J=7.04 Hz, 3H), 1.90-2.10 (m, 1H), 3.10 (t, J=6.30 Hz, 2H), 3.83 (s, 6H), 4.42-4.58 (m, 1H), 5.45 (q, J=7.04 Hz, 1H), 6.80 (s, 2H), 7.06 (d, J=7.40 Hz, 2H), 7.21 (t, J=7.45 Hz, 1H), 7.41 (t, J=7.80 Hz, 2H), 7.72 (s, 1H). $^{13}$C NMR ($CD_3OD$, d) 16.83, 28.98, 32.38, 44.52, 56.56, 56.82, 59.45, 111.68, 119.54, 121.85, 124.92, 128.80, 133.05, 136.04, 151.83, 152.25, 153.93, 161.23, 165.72, 166.00, 174.40, 179.09. MS m/z 584.4 $[M+H]^+$. HRMS calculated for $C_{27}H_{34}N_7O_6S$ 584.2286 found 584.2279 $[M+H]^+$, $C_{27}H_{33}N_7O_6NaS$ 606.2105 found 606.2115 $[M+Na]^+$.

(S)-N-((S)-1-amino-1-oxopropan-2-yl)-5-guanidino-2-((2Z,5Z)-5-(4-hydroxy-3,5-dimethoxybenzylidene)-4-oxo-2-(phenylimino)thiazolidin-3-yl)pentanamide [TZN87]. TZN87 was prepared by General Method H via the free amine TZN86 (22 mg, 0.04 mmol) to give the bis-Boc-guanidine KCB3-211, which was carried on crude to the free guanidine, purified on reverse phase HPLC (10 to 75% B in A over 30 min), TZN87 (7.1 mg, 0.01 mmol) as the TFA salt. $^1$H NMR (500 MHz, $CD_3OD$, d): 1.35 (d, J=7.18 Hz, 3H), 1.55-1.81 (m, 2H), 2.20-2.50 (m, 2H), 3.12-3.32 (m, 2H), 3.84 (s, 6H), 4.34-4.55 (m, 1H), 5.38 (t, J=7.48 Hz, 1H), 6.82 (s, 2H), 7.05 (d, J=7.46 Hz, 2H), 7.23 (t, J=7.32 Hz, 1H), 7.42 (t, J=7.79 Hz, 2H), 7.74 (s, 1H). $^{13}$C NMR ($CD_3OD$, d) 20.70, 28.81, 29.40, 44.62, 53.20, 59.47, 60.22, 111.70, 121.45, 124.80, 128.37, 128.86, 133.07, 136.17, 142.44, 151.71, 152.24, 153.67, 161.24, 170.88, 173.25, 180.33. MS m/z 584.3 $[M+H]^+$. HRMS calculated for $C_{27}H_{34}N_7O_6S$ 584.2286 found 584.2288 $[M+H]^+$.

Scheme III

General Method I for the solid phase synthesis is illustrated by the preparation of TZN49. TentaGel S Ram (Advanced ChemTech, 500 mg, 0.25 mmol/g, 0.125 mmol) was swollen in 15 mL $CH_2Cl_2$ for 30 min, then deprotected by two 10 min cycles of 20% piperidine/DMF(10 mL) with two DMF washes in between. The resin was washed successively with 10 mL each $CH_2Cl_2$ (3×), DMF (3×), MeOH (2×), and $CH_2Cl_2$ (3×). A solution of Fmoc L-alanine (117 mg, 0.375 mmol) in 5 mL $CH_2Cl_2$ was treated successively with hydroxyazobenztriazole (HOAt, 51 mg, 0.375 mmol), diisopropylcarbodiimide (DIC, 58 mL, 0.375 mmol), and diisopropylethylamine (109 mL, 0.525 mmol), and the reaction mixture stirred for 5 minutes, then added to the deprotected, washed resin, rinsing with an additional 10 mL $CH_2Cl_2$. The resin was shaken overnight, drained, and subjected to above standard washing protocol. A sample of the beads gave a negative Kaiser test. After deprotection as above, the sample of beads gave a positive Kaiser test, and the second Fmoc L-alanine was added by the identical procedure. Overnight shaking gave a resin showing, after washing, a negative Kaiser test. The resin was deprotected, washed, checked, and treated with 30 mL (0.25 mmol) phenylisothiocyanate in 10 mL $CH_2Cl_2$. Kaiser test showed the reaction to be incomplete after overnight shaking, and two additional 150 mL (1.25 mmol) phenylisothiocyanate in 10 mL were added over two days to complete the reaction. After washing, a sample of beads were removed, cleaved with 95:5 TFA:$CH_2Cl_2$ for 90 min, and the filtrate analyzed by mass spectrometry to show predominant peaks for the N-amidoAlaAla-N'-phenylthiourea at m/z $[M+Na]^+$317.2, $[M+H]^+$295.1. The resin was treated with methyl bromoacetate (115 mL, 1.25 mmol) and DIEA (436 mL, 2.5 mmol) in 10 mL $CH_2Cl_2$, washed, and an aliquot cleaved and examined by mass spectrometry as above to show a predominant $[M+H]^+$ molecular ion of 335.2. To the resin was added a solution of syringaldehyde (229 mg, 1.25 mmol) and piperidine (173 mL, 1.75 mmol) in 10 mL EtOH, and the suspension refluxed for 9 h. After draining and washing, a cleaved aliquot showed the presence of unreacted starting material, and the charge and reflux were repeated. The drained, washed resin was then cleaved by a 90 min treatment with 95:5:5 TFA:$H_2O$:triisopropylsilane (10 mL). After filtering the resin, and two washings with 10 mL MeOH each, the filtrate was concentrated in vacuo to give 39 mg of a crude product that was purified on RP-HPLC (20 to 95% B in A over 18 min) to provide 9.84 mg (0.02 mmol) TZN49 that was identical to the TZN49 obtained by solution chemistry under Scheme II. $^1$H NMR (500 MHz, $CD_3CN$, d) 1.35 (d, J=5.8 Hz, 3H), 1.67 (d, J=7.1 Hz, 1H), 3.83 (s, 6H), 4.35 (dq, J=7.2, 7.2 Hz, 1H), 5.32 (q, J=7.2, 7.2 Hz, 1H), 5.7 (br, 1H), 7.01 (s, 2H), 7.05-7.46 (m, 5H), 7.70 (s, 1H). MS m/z 499.3 $[M+H]^+$, 521.3 $[M+Na]^+$411.4 $[M-Ala+H]^+$. HRMS calculated for $C_{24}H_{26}N_4NaO_6S$ 521.1465, found 521.1467.

An earlier-eluting minor peak was identified as the D-Ala-L-Ala$NH_2$ diastereomer MS m/z 499.3 $[M+H]^+$, 521.3 $[M+Na]^+$411.4 [M−Ala+H], 428.4 $[M-C(CH_3)CONH_2+H]^+$.

N-((S)-1-amino-3-(4-hydroxyphenyl)-1-oxopropan-2-yl)-2-((2Z,5Z)-5-(4-hydroxy-3,5-dimethoxybenzylidene)-4-oxo-2-(phenylimino)thiazolidin-3-yl)-3-methylbutanamide [TZN68 (isomer A)]:

$^1$H NMR (500 MHz, $CD_3CN$, d) 0.48 (d, J=6.7 Hz, 3H), 0.81 (d, J=7.1 Hz, 3H), 2.0-0-2.10 (m, 1H), 2.90-3.10 (m, 2H), 3.61 (s, 6H), 3.73 (d, J=4.2 Hz, 1H). 4.30-4.39 (m, 1H), 5.8 (br, 1H), 6.3 (br, 1H), 6.58 (d, J=10.5 Hz, 2H) 6.78 (d, J=9.0 Hz, 2H), 6.92 (s, 2H), 7.43-7.62 (m, 5H), 7.69 (s, 1H). MS m/z 619.4 $[M+H]^+$, 641.4 $[M+Na]^+$. HRMS calculated for $C_{32}H_{35}N_4O_7S$ 619.2221, found 619.2216, $C_{32}H_{34}N_4NaO_7S$ 641.2040, found 641.2033.

N-((S)-1-amino-3-(4-hydroxyphenyl)-1-oxopropan-2-yl)-2-((2Z,5Z)-5-(4-hydroxy-3,5-dimethoxybenzylidene)-4-oxo-2-(phenylimino)thiazolidin-3-yl)-3-methylbutanamide [TZN69 (isomer B)]:

$^1$H NMR (500 MHz, $CD_3CN$, d) 0.0.86 (d, J=6.6 Hz, 3H), $^1$H NMR ($CD_3CN$) d 1.00 (d, J=6.5 Hz, 3H), 2.1-2.4 (m, 1H), 2.89-3.02 (m, 2H), 3.82 (s, 6H), 4.74 (ddd, J=3.1, 4.7, 7.8 Hz, 1H), 4.74 (d, J=10.9 Hz, 1H), 5.89-5.90 (br, 1H), 6.4-6.5 (br, 1H), 6.63 (d, J=8.7 Hz, 2H), 6.82 (s, 2H), 6.99 (d, J=8.5 Hz, 2H), 7.02-7/45 (m, 5H), 7.69 (s, 1H). MS m/z 619.4 $[M+H]^+$. HRMS calculated for $C_{32}H_{35}N_4O_7S$ 619.2221, found 619.2213, $C_{32}H_{34}N_4NaO_7S$ 641.2040, found 641.2031.

(S)-2-(5-guanidino-2-((2Z,5Z)-5-(4-hydroxy-3,5-dimethoxybenzylidene)-4-oxo-2-(phenylimino)thiazolidin-3-yl)pentanoyl)-1,2,3,4-tetrahydroisoquinoline-3-carboxamide [TZN88]:

$^1$H NMR (500 MHz, $CD_3CN$, d) 1.40-1.80 (m, 2H), 1.85-2.00 (m, 1H), 2.00-2.50 (m, 1H), 2.80-3.40 (m, 2H), 3.40-3.95 (m) over 3.66 (s, 8H total), 4.20-4.45 (m, 1H), 4.60-4.80 (m, 2H), 6.40-7.80 (m, 12H). MS m/z 672.4 $[M+H]^+$. HRMS calculated for $C_{34}H_{38}N_7O_6S$ 672.2599, found 672.2590.

(R)-3-(5-guanidino-2-((2Z,5Z)-5-(4-hydroxy-3,5-dimethoxybenzylidene)-4-oxo-2-(phenylimino)thiazolidin-3-yl)pentanoyl)thiazolidine-4-carboxamide [TZN94]:

$^1$H NMR (500 MHz, $CD_3CN$, d) 1.71-1.85 (m, 2H), 1.96-1.97 (m, 2H), 2.76-2.77 (m, 1H), 3.22 (br, 1H), 3.30-3.31 (m, 1H), 3.62 (s, 3H), 3.83 (s, 2H), 3.94 (s, 1H), 4.47-4.54 (m, 1H), 4.61-4.66 (m, 1H), 4.83-4.90 (m, 1H), 4.96-5.09 (m, 1H), 5.44-5.58 (m, 2H), 5.91-6.02 (m, 1H), 6.82 (s, 1H) 6.92

(s, 1H), 7.09-7.58 (m, 5H), 7.69 (s, 1H). MS m/z 628.4 $[M+H]^+$. HRMS calculated for $C_{28}H_{34}N_7O_6S_2$ 628.2006, found 628.2018.

(S)-5-guanidino-2-(2-((2Z,5Z)-5-(4-hydroxy-3,5-dimethoxybenzylidene)-4-oxo-2-(phenylimino)thiazolidin-3-yl)-3-(pyridin-4-yl)propanamido)pentanamide [TZN95]:

$^1$H NMR (500 MHz, $CD_3CN$, d) 1.61-1.75 (m, 2H), 2.76-2.77 (m, 1H), 3.55-3.72 (m, 2H), 3.82 (s, 2H), 3.92 (s, 1H), 4.33-4.52 (m, 1H), 5.65-5.67 (m, 1H), 5.82 (br, 1H), 6.77 (s, 2H), 6.80-7.69 (m, 10H), 7.73 (s, 1H), 8.22-8.46 (br, 1H), 8.47-8.51 (br, 2H). MS m/z 661.4 $[M+H]^+$. HRMS calculated for $C_{32}H_{37}N_8O_6S$ 661.2551, found 661.2576.

(S)-2-(S)-3-(biphenyl-4-yl)-2-(2Z,5Z)-5-(4-hydroxy-3,5-dimethoxybenzylidene)-4-oxo-2-(phenylimino)thiazolidin-3-yl)propanamido)-5-guanidinopentanamide [TZN96]:

$^1$H NMR (500 MHz, $CD_3CN$, d) 1.65-1.70 (m, 2H), 3.12-3.20 (m, 2H), 3.61 (s, 2H), 3.80 (s, 6H), 4.29-4.33 (m, 1H), 5.64 (dd, J=6.8 Hz. 1H), 5.86 (br, 1H), 6.75 (s, 2H), 6.85 (d, J=7.8 Hz, 2H), 7.19-7.62 (m, 13H), 7.87 (br, 1H). MS m/z 736.4 $[M+H]^+$. HRMS calculated for $C_{39}H_{42}N_7O_6S$ 736.2912, found 736.2888.

(2S)-5-guanidino-2-((2S)-2-(2Z,5Z)-5-(4-hydroxy-3,5-dimethoxybenzylidene)-4-oxo-2-(phenylimino)thiazolidin-3-yl)-3-(indolin-3-yl)propanamido)pentanamide [TZN97 (isomer A) and TZN98 (isomer B)]:

$^1$H NMR (500 MHz, $CD_3CN$, d) 1.60-1.85 (m, 2H), 2.54-2.94 (m, 3H), 3.09-3.16 (m, 3H), 3.50-3.68 (m, 3H), 3.84 (s, 6H), 4.38-4.47 (m, 1H), 5.47-5.60 (m, 1H), 5.82 (br, 1H), 6.83 (s, 2H) over 6.70-7.44 (m, 9H), 7.72 (s, 1H), 7.91 (br, 1H). MS m/z 701.6 $[M+H]^+$. HRMS calculated for $C_{35}H_{41}N_8O_6S$ 701.2864, found 701.2875.

2-((2Z,5Z)-5-(4-hydroxy-3,5-dimethoxybenzylidene)-4-oxo-2-(phenylimino)thiazolidin-3-yl)-N-(6-((2Z,5Z)-5-(4-hydroxy-3,5-dimethoxybenzylidene)-4-oxo-2-(phenylimino)thiazolidin-3-yl)hexyl)acetamide [TZN58]. General Method I for the formation of dimers is illustrated by the preparation of TZN58. To a solution of TZN45 (24 mg, 0.053 mmol) in 0.5 mL DMF at 0° C. was added TZN57 (25 mg, 0.061 mmol), DIEA (9.2 μL, 0.053 mmol), HOAT (7 mg, 0.053 mmol), and after 5 min, EDCI (16 mg, 0.053 mmol). The reaction mixture was allowed to warm to room temperature and stirred overnight. The crude reaction mixture was suspended in $CHCl_3$ and washed with $H_2O$, 1 mM citric acid, and $NaHCO_3$. The organic layer was dried over $Na_2SO_4$ and concentrated in vacuo. The crude solid was purified via silica gel chromatography using a gradient from 0 to 10% MeOH in $CHCl_3$ to give TZN58 (5.3 mg, 0.006 mmol). $^1$H NMR (300 MHz, DMSO-d6, d): 1.28-1.40 (m, 4H), 1.40-1.53 (m, 2H), 1.60-1.76 (m, 2H), 3.06-3.19 (m, 2H), 3.74 (s, 12H), 3.87 (t, J=7.50 Hz, 2H), 4.47 (s, 2H), 6.83 (s, 2H), 6.84 (s, 2H), 6.98 (d, J=7.46 Hz, 2H), 7.03 (d, J=7.49 Hz, 2H), 7.11-7.23 (m, 2H), 7.32-7.46 (m, 4H), 7.68 (s, 1H), 7.70 (s, 1H), 8.20 (t, J=5.31 Hz, 1H), 9.25 (s, 1H), 9.27 (s, 1H); $^{13}$C NMR (DMSO-d6, d): 30.36, 30.48, 31.26, 33.44, 43.04, 47.03, 49.43, 60.62, 112.61, 121.91, 121.99, 125.51, 125.57, 128.07, 128.12, 129.28, 133.87, 135.72, 135.93, 142.90, 142.97, 151.90, 152.27, 152.64, 154.14, 154.25, 169.76, 170.27, 170.37; MS m/z 874.3 $[M+Na]^+$; HRMS calculated for $C_{44}H_{45}N_5O_9NaS_2$ 874.2556 found 874.2550 $[M+Na]^+$.

4-((2Z,5Z)-5-(4-hydroxy-3,5-dimethoxybenzylidene)-4-oxo-2-(phenylimino)thiazolidin-3-yl)-N-(6-((2Z,5Z)-5-(4-hydroxy-3,5-dimethoxybenzylidene)-4-oxo-2-(phenylimino)thiazolidin-3-yl)hexyl)butanamide [TZN62]. TZN62 was prepared by General Method I on a 0.05 mmol scale via the free amine TZN45 and the free acid TZN61 to yield 13.8 mg (0.016 mmol) product. $^1$H NMR (300 MHz, $CD_3OD$, d): 1.25-1.57 (m, 8H), 1.64-1.98 (m, 4H), 3.01-3.14 (m, 2H), 3.79 (s, 6H), 3.85 (s, 6H), 3.81-3.99 (m, 4H), 6.67 (s, 2H), 6.76 (s, 2H), 6.98 (d, J=7.46 Hz, 2H), 7.17 (t, J=7.49 Hz, 1H), 7.38 (t, J=7.76 Hz, 2H), 7.42-7.68 (m, 7H); $^{13}$C NMR ($CD_3OD$, d): 13.03, 29.18, 29.49, 30.51, 31.08, 32.20, 42.11, 46.27, 59.36, 59.41, 71.23, 111.51, 111.65, 125.00, 128.12, 128.47, 128.57, 132.21, 132.99, 135.45, 136.30, 139.43, 152.08, 152.16, 170.53, 170.77, 176.77; MS m/z 880.7 $[M+H]^+$, 902.5 $[M+Na]^+$; HRMS calculated for $C_{46}H_{49}N_5O_9NaS_2$ 902.2864 found 902.2838 [M+Na].

5-(4-hydroxy-3,5-dimethoxybenzyl)-3-phenyl-2-(phenylimino)thiazolidin-4-one [TZN59]. TTSS29 (25 mg, 0.058 mmol) was hydrogenated over 10% palladium on carbon (53 mg) in a mixture of 11 mL EtOH and 3 mL DMF for 2.5 h. The catalyst was filtered off and the filtrate concentrated in vacuo. Preparative reverse phase HPLC using a gradient from 10 to 95% B in A over 20 min gave TZN59 (7.8 mg, 0.018 mmol). $^1$H NMR (300 MHz, $CDCl_3$, δ): 3.13-3.46 (m, 2H), 3.85 (s, 6H), 4.40-4.66 (m, 1H), 6.48 (s, 2H), 6.85 (d, J=7.49 Hz, 2H), 7.12 (t, J=7.36 Hz, 1H), 7.20 (d, J=7.23 Hz, 2H), 7.29-7.62 (m, 5H); $^{13}$C NMR ($CDCl_3$, δ): 43.28, 54.10, 60.32, 110.41, 124.91, 128.65, 130.26, 131.98, 133.02, 133.08, 133.33, 138.15, 138.63, 150.94, 152.17, 177.58; MS m/z 435.4 $[M+H]^+$, 457.3 [M+Na]; HRMS calculated for $C_{24}H_{22}N_2O_4NaS$ 457.1198 found 457.1179 $[M+Na]^+$.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for inhibiting Gram-negative bacterial pathogenesis associated with Type II and Type III secretion systems, comprising administering an effective amount of a compound to a subject in need thereof, wherein the compound has the formula:

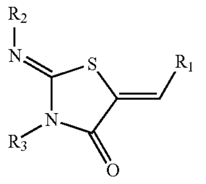

wherein, $R_1$ is selected from the group consisting of:

(a) substituted and unsubstituted aryl, (b) substituted and unsubstituted heteroaryl, (c) substituted and unsubstituted alkyl, and (d) substituted and unsubstituted cycloalkyl;

$R_2$ is substituted or unsubstituted aryl; and $R_3$ is —CH($R_4$)-Q-CH($R_5$)—Y, and Q is —C(═O)NH—, and Y is —C(═O)$NH_2$, wherein $R_4$ and $R_5$ are independently selected from the group consisting of natural and non-natural amino acid side chains.

2. The method of claim 1, wherein $R_1$ is selected from the group consisting of phenyl and substituted phenyl.

3. The method of claim 1, wherein $R_1$ is phenyl substituted at one or more of positions 3, 4, and 5 positions with one or more of —$OR_{11}$, —$NR_{11}R_{12}$, —$SR_{11}$, and halogen, wherein $R_{11}$ and $R_{12}$ are independently selected from the group of consisting of:

(a) hydrogen, (b) substituted and unsubstituted alkyl, (c) substituted and unsubstituted cycloalkyl, (d) substituted and unsubstituted aryl, (e) substituted and unsubstituted heteroaryl, and (f) —C(═O)$R_{13}$, wherein $R_{13}$ is selected from the group consisting of hydrogen, substituted and unsubstituted alkyl, and substituted and unsubstituted aryl.

4. The method of claim 1, wherein $R_1$ is 4-hydroxy-3,5-dimethoxyphenyl.

5. The method of claim 1, wherein $R_1$ is morpholinocarbamoylphenyl.

6. The method of claim 1, wherein $R_2$ is selected from the group consisting of phenyl and substituted phenyl.

7. A method for inhibiting Gram-negative bacterial pathogenesis associated with Type II and Type III secretion systems, comprising administering an effective amount of a compound to a subject in need thereof, wherein the compound has the formula:

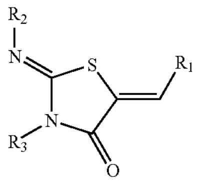

wherein, $R_1$ is selected from the group consisting of:

(a) 4-hydroxy-3,5-dimethoxyphenyl, and (b) morpholinocarbamoylphenyl;

$R_2$ is substituted or unsubstituted aryl; and $R_3$ is selected from the group consisting of:

(a) hydrogen, (b) substituted or unsubstituted alkyl, (c) substituted or unsubstituted cycloalkyl, (d) substituted or unsubstituted aryl, (e) substituted or unsubstituted heteroaryl, (f) —$CH(R_4)$—W—Y, wherein W is selected from the group consisting of:

(i) Q-$CH(R_5)$, wherein $R_4$ and $R_5$ are independently selected from the group consisting of natural and non-natural amino acid side chains, and Q is selected from the group consisting of —C(═O)NH—, —C(═O)O—, —$SO_2NH$—, and —P(O)($OR_8$)NH—, wherein $R_8$ is selected from the group consisting of hydrogen and substituted or unsubstituted alkyl, and (ii) C(═O)$NR_6CH(R_7)$, wherein $R_6$ and $R_7$ taken together with the carbon and the nitrogen atoms to which they are attached form a 5- to 7-membered ring that optionally includes one or more heteroatoms, and wherein Y is selected from the group consisting of —C(═O)$NH_2$, —C(═O)OH, —$SO_2NH_2$,and —P(O)($OR_8$)$NH_2$, wherein $R_8$ is selected from the group consisting of hydrogen and substituted or unsubstituted alkyl, and (g) —$(CH_2)_nN(R_9)X(CH_2)_mR_{10}$, wherein n is an integer from 1 to 8, m is an integer from 1 to 8, X is selected from the group consisting of C(═O), N(C═O)OH, N(C═NH)NH, and $CH_2$, $R_9$ is hydrogen or substituted or unsubstituted alkyl, and $R_{10}$ is heterocyclyl.

* * * * *

SEQUENCE LISTING

<160> NUMBER OF SEQ ID NOS: 4

<210> SEQ ID NO 1
<211> LENGTH: 685
<212> TYPE: PRT
<213> ORGANISM: Salmonella typhimurium

<400> SEQUENCE: 1

Met Val Thr Ser Val Arg Thr Gln Pro Pro Val Ile Met Pro Gly Met
1 5 10 15

Gln Thr Glu Ile Lys Thr Gln Ala Thr Asn Leu Ala Ala Asn Leu Ser
20 25 30

Ala Val Arg Glu Ser Ala Thr Ala Thr Leu Ser Gly Glu Ile Lys Gly
35 40 45

```
Pro Gln Leu Glu Asp Phe Pro Ala Leu Ile Lys Gln Ala Ser Leu Asp
    50                  55                  60

Ala Leu Phe Lys Cys Gly Lys Asp Ala Glu Ala Leu Lys Glu Val Phe
65                  70                  75                  80

Thr Asn Ser Asn Asn Val Ala Gly Lys Lys Ala Ile Met Glu Phe Ala
                85                  90                  95

Gly Leu Phe Arg Ser Ala Leu Asn Ala Thr Ser Asp Ser Pro Glu Ala
            100                 105                 110

Lys Thr Leu Leu Met Lys Val Gly Ala Glu Tyr Thr Ala Gln Ile Ile
        115                 120                 125

Lys Asp Gly Leu Lys Glu Lys Ser Ala Phe Gly Pro Trp Leu Pro Glu
    130                 135                 140

Thr Lys Lys Ala Glu Ala Lys Leu Glu Asn Leu Glu Lys Gln Leu Leu
145                 150                 155                 160

Asp Ile Ile Lys Asn Asn Thr Gly Gly Glu Leu Ser Lys Leu Ser Thr
                165                 170                 175

Asn Leu Val Met Gln Glu Val Met Pro Tyr Ile Ala Ser Cys Ile Glu
            180                 185                 190

His Asn Phe Gly Cys Thr Leu Asp Pro Leu Thr Arg Ser Asn Leu Thr
        195                 200                 205

His Leu Val Asp Lys Ala Ala Ala Lys Ala Val Glu Ala Leu Asp Met
    210                 215                 220

Cys His Gln Lys Leu Thr Gln Glu Gln Gly Thr Ser Val Gly Arg Glu
225                 230                 235                 240

Ala Arg His Leu Glu Met Gln Thr Leu Ile Pro Leu Leu Leu Arg Asn
                245                 250                 255

Val Phe Ala Gln Ile Pro Ala Asp Lys Leu Pro Asp Pro Lys Ile Pro
            260                 265                 270

Glu Pro Ala Ala Gly Pro Val Pro Asp Gly Gly Lys Lys Ala Glu Pro
        275                 280                 285

Thr Gly Ile Asn Ile Asn Ile Asn Ile Asp Ser Ser Asn His Ser Val
    290                 295                 300

Asp Asn Ser Lys His Ile Asn Asn Ser Arg Ser His Val Asp Asn Ser
305                 310                 315                 320

Gln Arg His Ile Asp Asn Ser Asn His Asp Asn Ser Arg Lys Thr Ile
                325                 330                 335

Asp Asn Ser Arg Thr Phe Ile Asp Asn Ser Gln Arg Asn Gly Glu Ser
            340                 345                 350

His His Ser Thr Asn Ser Ser Asn Val Ser His Ser His Ser Arg Val
        355                 360                 365

Asp Ser Thr Thr His Gln Thr Glu Thr Ala His Ser Ala Ser Thr Gly
    370                 375                 380

Ala Ile Asp His Gly Ile Ala Gly Lys Ile Asp Val Thr Ala His Ala
385                 390                 395                 400

Thr Ala Glu Ala Val Thr Asn Ala Ser Ser Glu Ser Lys Asp Gly Lys
                405                 410                 415

Val Val Thr Ser Glu Lys Gly Thr Thr Gly Glu Thr Thr Ser Phe Asp
            420                 425                 430

Glu Val Asp Gly Val Thr Ser Lys Ser Ile Ile Gly Lys Pro Val Gln
        435                 440                 445

Ala Thr Val His Gly Val Asp Asp Asn Lys Gln Gln Ser Gln Thr Ala
    450                 455                 460

Glu Ile Val Asn Val Lys Pro Leu Ala Ser Gln Leu Ala Gly Val Glu
```

-continued 465 470 475 480

Asn Val Lys Thr Asp Thr Leu Gln Ser Asp Thr Thr Val Ile Thr Gly
485 490 495

Asn Lys Ala Gly Thr Thr Asp Asn Asp Asn Ser Gln Thr Asp Lys Thr
500 505 510

Gly Pro Phe Ser Gly Leu Lys Phe Lys Gln Asn Ser Phe Leu Ser Thr
515 520 525

Val Pro Ser Val Thr Asn Met His Ser Met His Phe Asp Ala Arg Glu
530 535 540

Thr Phe Leu Gly Val Ile Arg Lys Ala Leu Glu Pro Asp Thr Ser Thr
545 550 555 560

Pro Phe Pro Val Arg Arg Ala Phe Asp Gly Leu Arg Ala Glu Ile Leu
565 570 575

Pro Asn Asp Thr Ile Lys Ser Ala Ala Leu Lys Ala Gln Cys Ser Asp
580 585 590

Ile Asp Lys His Pro Glu Leu Lys Ala Lys Met Glu Thr Leu Lys Glu
595 600 605

Val Ile Thr His His Pro Gln Lys Glu Lys Leu Ala Glu Ile Ala Leu
610 615 620

Gln Phe Ala Arg Glu Ala Gly Leu Thr Arg Leu Lys Gly Glu Thr Asp
625 630 635 640

Tyr Val Leu Ser Asn Val Leu Asp Gly Leu Ile Gly Asp Gly Ser Trp
645 650 655

Arg Ala Gly Pro Ala Tyr Glu Ser Tyr Leu Asn Lys Pro Gly Val Asp
660 665 670

Arg Val Ile Thr Thr Val Asp Gly Leu His Met Gln Arg
675 680 685

<210> SEQ ID NO 2
<211> LENGTH: 2055
<212> TYPE: DNA
<213> ORGANISM: Salmonella typhimurium

<400> SEQUENCE: 2
atggttacaa gtgtaaggac tcagcccccc gtcataatgc caggtatgca gaccgagatc 60
aaaacgcagg ccacgaatct tgcggcgaat ctttccgcag tcagagaaag tgccacagcg 120
acgctgtcag gggaaattaa aggcccgcaa ctggaagatt ttcccgcgct gatcaaacag 180
gcgagtctgg atgcattgtt taaatgcggg aaagacgctg aggcgttaaa agaagttttt 240
accaattcaa ataatgtcgc cggtaagaaa gcgataatgg agtttgccgg gctctttcgt 300
tcagcgctca acgccaccag tgattctcct gaggcgaaga cgctactgat gaaggtgggg 360
gcagagtata ccgcgcaaat cataaaagat ggcctgaaag aaaagtcagc ttttgggcca 420
tggctgccag aaacaaagaa agcggaagcg aagctggaaa acctggaaaa gcagctgtta 480
gatattatca aaaataacac tggcggtgaa ttaagtaaat tatcgacgaa tcttgttatg 540
caggaggtga tgccctatat tgccagctgc attgaacata actttggctg tacgttagat 600
ccgttaaccc gcagcaatct tacgcacctt gttgacaaag cggcggcgaa ggctgttgag 660
gcgcttgata tgtgccacca aaaattaacg caagagcagg gtaccagcgt aggacgggaa 720
gcccggcacc ttgaaatgca aacgttgata cccctgctgc tacgtaatgt ttttgcacaa 780
attcctgcag ataaactgcc tgaccctaaa attccggagc ctgcggctgg accagtacct 840
gatggtggga aaaaagcaga acctacgggt attaatatca atattaatat tgatagcagt 900
aaccatagcg tggataacag taagcatatt aacaatagcc gaagccatgt cgataatagc 960

-continued

```
cagcgccata tcgataatag caaccatgat aatagccgga agacgattga taatagccga   1020
acatttattg ataacagcca acgcaatggc gagtcacacc attcgactaa cagcagcaac   1080
gtaagtcata gtcattcgcg tgtggattcg actacgcatc aaacggagac ggcacacagc   1140
gccagcacag gggcaattga ccatggcatc gcgggtaaaa ttgacgtcac ggctcatgcg   1200
acggcagagg ctgtgaccaa cgcttcatcc gaaagtaaag atggaaaggt ggtcacgtca   1260
gaaaagggca ctacgggtga aacaacctct tttgatgaag tcgatggcgt aaccagcaag   1320
agcattatcg gcaagccggt acaggccacg gtgcacggcg ttgatgataa taaacagcaa   1380
agccagacgg cagagattgt gaatgtgaag ccgcttgcca gtcaactggc tggcgtcgag   1440
aatgttaaaa ccgatacctt acaatcagac acgacggtaa ttacaggtaa taaagccggt   1500
acgaccgata atgataatag tcagacagat aagactggcc cattttctgg tttgaagttt   1560
aagcaaaata gtttcctctc aacagtaccg agcgttacga atatgcattc aatgcatttc   1620
gacgcccgtg agacgttttt gggtgtgata cgtaaagccc tggagccaga tacctccaca   1680
ccgttccctg tacgcagagc gtttgacggc ttgcgtgcgg aaatattacc caatgacacg   1740
ataaagagtg cagcgttgaa agcgcaatgt agcgatattg acaagcaccc agaattgaaa   1800
gcgaaaatgg agactctcaa agaggtcatt actcatcatc cacaaaaaga aaaactggct   1860
gagattgcac tgcagtttgc cagagaggcg gggctgacca ggctaaaagg ggaaactgac   1920
tatgtgttaa gtaatgtgct ggacggcctt atcggagacg gtagctggcg agctggcccg   1980
gcttacgagt catacctgaa taaacctggc gtggatcggg ttattactac cgttgatggc   2040
ttgcacatgc agcgt                                                    2055
```

<210> SEQ ID NO 3
<211> LENGTH: 265
<212> TYPE: PRT
<213> ORGANISM: Yersinia enterocolitica

<400> SEQUENCE: 3

```
Met Leu Ala Ser Leu Gly Ile Ser Arg Gly Glu Arg Val Leu Ala Ala
1               5                   10                  15

Ser Asp Asn Val Pro Ile Ser Ser Gly Gln Gly Ser Gln Gln Ala Asp
            20                  25                  30

Tyr Ser Leu Ala Leu Leu Ala Lys Asp Val Tyr Ala Pro Ala Ala Arg
        35                  40                  45

Ser Ile Gly Gly Phe Thr Arg Leu Gly Asp Ala Ala Leu Leu Ser Ala
    50                  55                  60

Gly Ile Asp Pro Ala Ser Leu Ser Asp Thr Ala Ser Gly Phe Gln Ala
65                  70                  75                  80

Gly Ile Tyr Ser Asp Asn Gln Gln Tyr Val Leu Ser Phe Ala Gly Thr
                85                  90                  95

Asn Asp Ile Gln Asp Trp Leu Ser Asn Ile Arg Gln Ala Thr Gly Tyr
            100                 105                 110

Glu Asp Val Gln Tyr Asn Gln Ala Val Ala Leu Gly Lys Thr Ala Lys
        115                 120                 125

Met Ala Phe Gly Asp Ala Leu Val Ile Thr Gly His Ser Leu Gly Gly
    130                 135                 140

Gly Leu Ala Ala Thr Ala Ala Leu Ala Ser Gly Thr Phe Ala Val Thr
145                 150                 155                 160

Phe Asn Ala Ala Gly Val Ser Asp His Thr Leu Asn Arg Leu Gly Met
                165                 170                 175
```

-continued

Asn Pro Ala Gln Ala Arg Gln Ser Ala Glu Gly Gly Gly Ile Arg Arg
180 185 190

Tyr Ser Glu Gln His Asp Leu Leu Thr Asp Thr Gln Glu Ser Thr Ser
195 200 205

Leu Ile Pro Asp Ala Ile Gly His Lys Ile Thr Leu Ala Asn Ser Asp
210 215 220

Lys Leu Ala Gly Val Asn Asp Trp Leu Pro His Lys His Leu Glu Arg
225 230 235 240

Ser Leu Ala Ala His Gly Ile Asp Lys Val Leu Ser Ser Met Asn Glu
245 250 255

Gln Gln Pro Trp Glu Arg Gln Tyr Ala
260 265

<210> SEQ ID NO 4
<211> LENGTH: 798
<212> TYPE: DNA
<213> ORGANISM: Yersinia enterocolitica

<400> SEQUENCE: 4
atgctggcta gccttggaat atcacgtggt gaacgtgttt tagctgccag cgacaatgta 60
ccgatatcaa gtggacaagg atcacagcaa gcggactatt cattagcatt actcgcgaaa 120
gatgtttacg ctcctgctgc gagaagcatc ggcggattta cacggttggg tgatgccgcg 180
ttgctttcgg cggggataga tccggcgagc ctatctgata cagcttcagg gtttcaggct 240
gggatttaca gtgataatca acagtatgtc ctctctttcg cgggtaccaa tgatattcag 300
gattggttaa gtaatatccg gcaagcaaca ggttatgagg atgttcaata taatcaggct 360
gttgcgctgg ggaaaaccgc taaaatggca tttggtgatg cactggtcat taccggccat 420
tcattaggcg gtgggctggc agccacggct gcattagcca gcgggacttt tgctgtaaca 480
tttaatgccg ccggtgtttc tgatcacaca ttaaatcgtt tgggcatgaa ccctgctcag 540
gcgcggcagt cggcsgaggg gggtggcata cgacgttata gtgagcaaca tgacttattg 600
acggatactc aagagtcaac ctcactcatt cctgatgcaa ttggccataa gatcacattg 660
gctaatagcg ataaactggc gggggtaaat gactggctgc cacacaaaca cctcgaacgt 720
agccttgcgg cgcatggtat tgataaagtg ctcagttcca tgaatgaaca acaaccttgg 780
gagcggcagt atgcctga 798